United States Patent
Bosmans et al.

(10) Patent No.: US 7,638,535 B2
(45) Date of Patent: *Dec. 29, 2009

(54) 4-(AMINOMETHYL)-PIPERIDINE BENZAMIDES AS $5HT_4$-ANTAGONISTS

(75) Inventors: Jean-Paul René Marie André Bosmans, Rijkevorsel (BE); Henricus Jacobus Maria Gijsen, Breda (NL); Laurence Anne Mevellec, Louviers (FR)

(73) Assignee: Janssen Pharmaceutica N.V., Beerse (BE)

( * ) Notice: Subject to any disclaimer, the term of this patent is extended or adjusted under 35 U.S.C. 154(b) by 499 days.

This patent is subject to a terminal disclaimer.

(21) Appl. No.: 10/560,479

(22) PCT Filed: Jun. 10, 2004

(86) PCT No.: PCT/EP2004/006285

§ 371 (c)(1),
(2), (4) Date: Dec. 12, 2005

(87) PCT Pub. No.: WO2005/000838

PCT Pub. Date: Jan. 6, 2005

(65) Prior Publication Data

US 2006/0281753 A1 Dec. 14, 2006

(30) Foreign Application Priority Data

Jun. 19, 2003 (WO) .................. PCT/EP03/50236

(51) Int. Cl.
*A61K 31/445* (2006.01)
(52) U.S. Cl. ...................................... 514/320; 546/197

(58) Field of Classification Search ................. 514/320; 546/197

See application file for complete search history.

(56) References Cited

U.S. PATENT DOCUMENTS 4,186,135 A * 1/1980 Thominet et al. ........... 548/526
6,544,997 B1 * 4/2003 Bosmans et al. ........ 514/255.05
6,635,643 B2 * 10/2003 Bosmans et al. ............ 514/248

FOREIGN PATENT DOCUMENTS

WO    WO 00/37461 A    6/2000

OTHER PUBLICATIONS

Search report for International Application No. PCT/EP/2004/006285.

* cited by examiner

*Primary Examiner*—Celia Chang
(74) *Attorney, Agent, or Firm*—Woodcock Washburn LLP

(57) ABSTRACT

The present invention is concerned with novel compounds of formula (I) having $5HT_4$-antagonistic properties. The invention further relates to methods for preparing such novel compounds, pharmaceutical compositions comprising said novel compounds as well as the use as a medicine of said compounds.

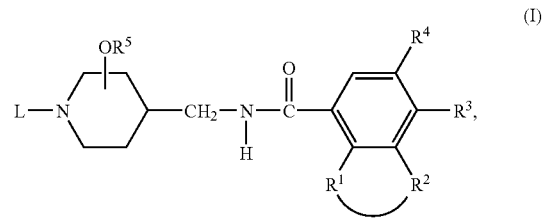

9 Claims, No Drawings

4-(AMINOMETHYL)-PIPERIDINE BENZAMIDES AS 5HT$_4$-ANTAGONISTS

CROSS REFERENCE TO RELATED APPLICATIONS

This application is the national stage of Application No. PCT/EP2004/006285, filed Jun. 10, 2004, which application claims priority from Appl. No. PCT/EP03/50236, filed Jun. 19, 2003.

The present invention is concerned with novel compounds of formula (I) having 5HT$_4$-antagonistic properties. The invention further relates to methods for preparing such novel compounds, pharmaceutical compositions comprising said novel compounds as well as the use as a medicine of said compounds.

WO-00/37461 discloses bicyclic benzamides of 3- or 4-substituted 4-(aminomethyl)-piperidine derivatives having 5HT$_4$-antagonistic properties.

The compounds of the present invention differ from the cited art-known compounds structurally, by the presence of a functional group on the 4-position of the benzamide moiety which is other than a hydrogen or halo group.

Unexpectedly, the present compounds of formula (I) have improved metabolic stability properties compared with the compounds disclosed in WO-00/37461.

The present invention concerns compounds of formula (I)

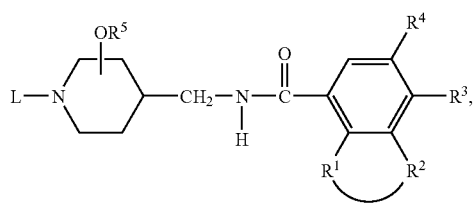

a stereochemically isomeric form thereof, an N-oxide form thereof, or a pharmaceutically acceptable acid or base addition salt thereof, wherein
—R$^1$-R$^2$— is a bivalent radical of formula

| | |
|---|---|
| —O—CH$_2$—O— | (a-1), |
| —O—CH$_2$—CH$_2$— | (a-2), |
| —O—CH$_2$—CH$_2$—O— | (a-3), |
| —O—CH$_2$—CH$_2$—CH$_2$— | (a-4), |
| —O—CH$_2$—CH$_2$—CH$_2$—O— | (a-5), |
| —O—CH$_2$—CH$_2$—CH$_2$—CH$_2$— | (a-6), |
| —O—CH$_2$—CH$_2$—CH$_2$—CH$_2$—O— | (a-7), |
| —O—CH$_2$—CH$_2$—CH$_2$—CH$_2$—CH$_2$— | (a-8), | wherein in said bivalent radicals optionally one or two hydrogen atoms on the same or a different carbon atom may be replaced by C$_{1-6}$alkyl or hydroxy,
R$^3$ is hydrogen, halo, C$_{1-4}$alkyl;
R$^4$ is C$_{1-6}$alkyl; C$_{1-6}$alkyl substituted with cyano, or C$_{1-6}$alkyloxy; C$_{1-6}$alkyloxy; cyano; amino or mono or di(C$_{1-6}$alkyl)amino;
R$^5$ is hydrogen or C$_{1-6}$alkyl, and the —OR$^5$ radical is situated at the 3- or 4-position of the piperidine moiety;
L is hydrogen, or L is a radical of formula

| | |
|---|---|
| -Alk-R$^6$ | (b-1), |
| -Alk-X—R$^7$ | (b-2), |
| -Alk-Y—C(=O)—R$^9$ | (b-3), or |
| -Alk-Z-C(=O)—NR$^{11}$R$^{12}$ | (b-4), | wherein each Alk is C$_{1-12}$alkanediyl; and
R$^6$ is hydrogen; hydroxy; cyano; C$_{3-6}$cycloalkyl; C$_{1-6}$alkylsulfonylamino; aryl or Het;
R$^7$ is C$_{1-6}$alkyl; C$_{1-6}$alkyl substituted with hydroxy; C$_{3-6}$cycloalkyl; aryl or Het;
X is O, S, SO$_2$ or NR$^8$; said R$^8$ being hydrogen or C$_{1-6}$alkyl;
R$^9$ is hydrogen, C$_{1-6}$alkyl, C$_{3-6}$cycloalkyl, hydroxy or aryl;
Y is a direct bond, or NR$^{10}$ wherein R$^{10}$ is hydrogen or C$_{1-6}$alkyl;
Z is a direct bond, O, S, or NR$^{10}$ wherein R$^{10}$ is hydrogen or C$_{1-6}$alkyl;
R$^{11}$ and R$^{12}$ each independently are hydrogen, C$_{1-6}$alkyl, C$_{3-6}$cycloalkyl, or R$^{11}$ and R$^{12}$ combined with the nitrogen atom bearing R$^{11}$ and R$^{12}$ may form a pyrrolidinyl, piperidinyl, piperazinyl or 4-morpholinyl ring both being optionally substituted with C$_{1-6}$alkyl;
aryl represents unsubstituted phenyl or phenyl substituted with 1, 2 or 3 substituents each independently selected from halo, hydroxy, C$_{1-6}$alkyl, C$_{1-6}$alkyloxy, C$_{1-6}$alkylcarbonyl, nitro, trifluoromethyl, amino, aminocarbonyl, and aminosulfonyl; and
Het is furanyl; furanyl substituted with C$_{1-6}$alkyl or halo;
  tetrahydrofuranyl; tetrahydrofuranyl substituted with C$_{1-6}$alkyl;
  dioxolanyl; dioxolanyl substituted with C$_{1-6}$alkyl;
  dioxanyl; dioxanyl substituted with C$_{1-6}$alkyl;
  tetrahydropyranyl; tetrahydropyranyl substituted with C$_{1-6}$alkyl;
  2,3-dihydro-2-oxo-1H-imidazolyl; 2,3-dihydro-2-oxo-1H-imidazolyl substituted with one or two substituents each independently selected from halo, or C$_{1-6}$alkyl;
  pyrrolidinyl; pyrrolidinyl substituted with one or two substituents each independently selected from halo, hydroxy, or C$_{1-6}$alkyl;
  pyridinyl; pyridinyl substituted with one or two substituents each independently selected from halo, hydroxy, or C$_{1-6}$alkyl;
  pyrimidinyl; pyrimidinyl substituted with one or two substituents each independently selected from halo, hydroxy, or C$_{1-6}$alkyl;
  pyridazinyl; pyridazinyl substituted with one or two substituents each independently selected from hydroxy, C$_{1-6}$alkyloxy, C$_{1-6}$alkyl or halo;
  pyrazinyl; pyrazinyl substituted with one or two substituents each independently selected from hydroxy, C$_{1-6}$alkyloxy, C$_{1-6}$alkyl or halo.

As used in the foregoing definitions halo is generic to fluoro, chloro, bromo and iodo; C$_{1-4}$alkyl defines straight and branched chain saturated hydrocarbon radicals having from 1 to 4 carbon atoms such as, for example, methyl, ethyl, propyl, butyl, 1-methyl-ethyl, 2-methylpropyl and the like; C$_1$alkyl is meant to include C$_{1-4}$alkyl and the higher homologues thereof having 5 or 6 carbon atoms, such as, for example, 2-methylbutyl, pentyl, hexyl and the like; C$_{3-6}$cycloalkyl is generic to cyclopropyl, cyclobutyl, cyclopentyl and cyclohexyl; C$_{1-12}$alkanediyl defines bivalent straight or branched chain hydrocarbon radicals containing from 1 to 12 carbon atoms such as, for example, methanediyl, 1,2-ethanediyl, 1,3-propanediyl, 1,4-butanediyl, 1,5-pentanediyl, 1,6-hexanediyl, 1,7-heptanediyl, 1,8-octanediyl, 1,9-nonanediyl, 1,10-decanediyl, 1,11-undecanediyl, 1,12-dodecanediyl and the branched isomers thereof. $C_{1-4}$alkanediyl defines bivalent straight or branched chain hydrocarbon radicals containing from 1 to 4 carbon atoms such as, for example, methanediyl, 1,2-ethanediyl, 1,3-propanediyl, and 1,4-butanediyl.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of formula (I) are obviously intended to be embraced within the scope of this invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

Some of the compounds of formula (I) may also exist in their tautomeric form. Such forms although not explicitly indicated in the above formula are intended to be included within the scope of the present invention. For instance, when an aromatic heterocyclic ring is substituted with hydroxy the keto-form may be the mainly populated tautomer.

The N-oxide forms of the compounds of formula (I), which may be prepared in art-known manners, are meant to comprise those compounds of formula (I) wherein one or several nitrogen atoms are oxidized to the N-oxide. Particularly those N-oxides are envisaged wherein the piperidine-nitrogen is N-oxidized.

A group of interesting compounds consists of those compounds of formula (I) wherein one or more of the following restrictions apply:

a) —$R^1$-$R^2$— is a radical of formula (a-3); and/or
b) —$R^1$-$R^2$— is a radical of formula (a-5); and/or
c) $R^3$ is hydrogen or halo; and/or
d) $R^4$ is methyl, methoxy, methoxymethyl, cyano, cyanomethylamino, amino or $C_{1-6}$alkylamino; and/or
e) $R^5$ is hydrogen, or methyl, and the —$OR^5$ radical is situated at the 3- or 4-position of the piperidine ring; and/or
f) $R^5$ is hydrogen, and the —$OR^5$ radical is situated at the 3-position of the piperidine ring; and/or
g) $R^5$ is hydrogen, and the —$OR^5$ radical is situated at the 4-position of the piperidine ring; and/or
h) the —$OR^5$ radical is situated at the 3-position of the piperidine ring and is in the trans position in relation to the methylene on the 4-position of the piperidine moiety; and/or
i) the —$OR^5$ radical is situated at the 3-position of the piperidine ring and is in the trans position in relation to the methylene on the 4-position of the piperidine moiety and the absolute configuration of said piperidine moiety is (3S, 4S); and/or
j) L is hydrogen;
k) L is a radical of formula (b-1), (b-2), (b-3), or (b-4); or
l) L is a radical of formula (b-1) wherein Alk is $C_{1-4}$alkanediyl, and $R^6$ is hydrogen, hydroxy, cyano, $C_{3-6}$cycloalkyl, $C_{1-6}$alkylsulfonylamino, aryl representing phenyl substituted with halo or hydroxy; or Het representing tetrahydrofuranyl, dioxolanyl, dioxolanyl substituted with $C_{1-4}$alkyl, or pyridinyl; or L is a radical (b-2) wherein Alk is $C_{1-4}$alkanediyl, and X represents O and $R^7$ is $C_{3-6}$cycloalkyl, $C_{1-6}$alkyl, $C_{1-6}$alkyl substituted with hydroxy, or aryl representing phenyl substituted with aminosulfonyl; or L is a radical (b-2) wherein Alk is $C_{1-4}$alkanediyl, and X represents $NR^8$ wherein $R^8$ is hydrogen and $R^7$ is $C_{1-6}$alkyl, or Het representing pyrimidinyl or pyrazinyl substituted with $C_{1-6}$alkyl; or L is a radical (b-2) wherein Alk is $C_{1-4}$alkanediyl, and X represents $SO_2$ and $R^7$ is $C_{1-6}$alkyl; or L is a radical (b-3) wherein Alk is $C_{1-4}$alkanediyl, and Y is a direct bond and $R^9$ is $C_{1-6}$alkyl or hydroxy; or L is a radical of formula (b-4) wherein Alk is $C_{1-4}$alkanediyl, and Z is a direct bond, and $R^{11}$ and $R^{12}$ represent both hydrogen, or $R^{11}$ and $R^{12}$ combined with the nitrogen atom bearing $R^{11}$ and $R^{12}$ form pyrrolidinyl or piperazinyl substituted with $C_{1-6}$alkyl; or L is a radical of formula (b-4) wherein Alk is $C_{1-4}$alkanediyl, and Z is O, and $R^{11}$ and $R^{12}$ combined with the nitrogen atom bearing $R^{11}$ and $R^{12}$ form pyrrolidinyl.

Other interesting compounds are those compounds of formula (I) wherein

—$R^1$-$R^2$— is a bivalent radical of formula $$-O-CH_2-CH_2-O- \qquad (a\text{-}3),$$

$$-O-CH_2-CH_2-CH_2-O- \qquad (a\text{-}5),$$

$R^3$ is hydrogen, halo, $C_{1-4}$alkyl;

$R^4$ is $C_{1-6}$alkyl; $C_{1-6}$alkyl substituted with cyano, or $C_{1-6}$alkyloxy; $C_{1-6}$alkyloxy; cyano; amino or mono or di($C_{1-6}$alkyl)amino;

$R^5$ is hydrogen or $C_{1-6}$alkyl, and the —$OR^5$ radical is situated at the 3- or 4-position of the piperidine moiety;

L is hydrogen, or L is a radical of formula

-Alk-$R^6$ (b-1),

-Alk-X—$R^7$ (b-2),

-Alk-Y—C(=O)—$R^9$ (b-3), or

-Alk-Z-C(=O)—$NR^{11}R^{12}$ (b-4), wherein each Alk is $C_{1-12}$alkanediyl; and
$R^6$ is hydrogen; hydroxy; cyano; $C_{3-6}$cycloalkyl; $C_{1-6}$alkylsulfonylamino; aryl or Het;
$R^7$ is $C_{1-6}$alkyl; $C_{1-6}$alkyl substituted with hydroxy; $C_{3-6}$cycloalkyl; aryl or Het;
X is O, S, $SO_2$ or $NR^8$; said $R^8$ being hydrogen or $C_{1-6}$alkyl;
$R^9$ is $C_{1-6}$alkyl or hydroxy;
Y is a direct bond;
Z is a direct bond or O;
$R^{11}$ and $R^{12}$ each independently are hydrogen, or $C_{1-6}$alkyl, or $R^{11}$ and $R^{12}$ combined with the nitrogen atom bearing $R^{11}$ and $R^{12}$ may form a pyrrolidinyl, or piperazinyl substituted with $C_{1-6}$alkyl;
aryl represents unsubstituted phenyl or phenyl substituted with 1, 2 or 3 substituents each independently selected from halo, hydroxy, $C_{1-6}$alkyl, $C_{1-6}$alkyloxy, and aminosulfonyl; and
Het is tetrahydrofuranyl; tetrahydrofuranyl substituted with $C_{1-6}$alkyl;
dioxolanyl; dioxolanyl substituted with $C_{1-6}$alkyl;
pyridinyl; pyridinyl substituted with one or two substituents each independently selected from halo, hydroxy, $C_{1-6}$alkyl;
pyrimidinyl; pyrimidinyl substituted with one or two substituents each independently selected from halo, hydroxy, or $C_{1-6}$alkyl;
pyridazinyl; pyridazinyl substituted with one or two substituents each independently selected from hydroxy, $C_{1-6}$alkyloxy, $C_{1-6}$alkyl or halo;
pyrazinyl; pyrazinyl substituted with one or two substituents each independently selected from hydroxy, $C_{1-6}$alkyloxy, $C_{1-6}$alkyl or halo.

Particular compounds are those compounds of formula (I) wherein the —$OR^5$ radical, preferably representing hydroxy or methoxy, is situated at the 3-position of the piperidine moiety having the trans configuration, i.e. the —$OR^5$ radical is in the trans position in relation to the methylene on the piperidine moiety.

More particular compounds are those compounds of formula (I) wherein the bivalent radical —$R^1$-$R^2$— is a radical of formula (a-3) or (a-5), the —$OR^5$ radical represents hydroxy and is situated at the 3-position of the piperidine moiety having the (3S-trans) configuration which corresponds to absolute (3S,4S) configuration of said piperidine moiety.

Preferred compounds are those more particular compounds wherein —$R^1$-$R^2$— is a radical of formula (a-5); $R^3$ is hydrogen; $R^4$ is methyl; and $R^5$ is hydrogen.

More preferred compounds are those preferred compounds wherein L is a radical of formula (b-2) wherein X is O, Alk is $C_{1-4}$alkanediyl and $R^7$ is $C_{1-6}$alkyl, preferably methyl.

Most preferred compounds are the compounds (87), (125), (158), (159), (162), (163), (165), (168), (177), (183), (184), (185), (186), (187), (200), (202), (211), (225), (228), (229), (246), and (247).

The compounds of formula (I) can be prepared by reacting an intermediate of formula (II) with an carboxylic acid derivative of formula (M) or, optionally a reactive functional derivative thereof, such as, e.g. carbonyl imidazole derivatives, acyl halides or mixed anhydrides. Said amide-bond formation may be performed by stirring the reactants in an appropriate solvent, optionally in the presence of a base, such as triethylamine.

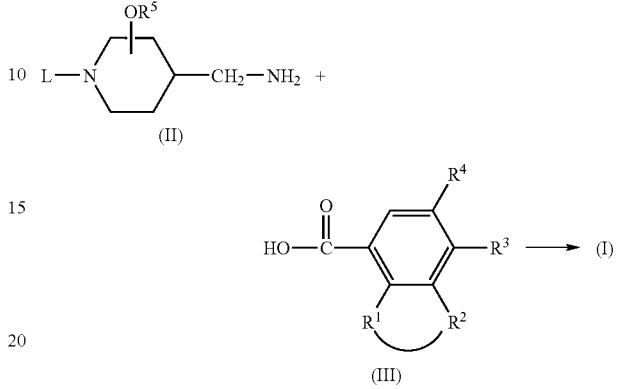

Compounds of formula (I-b), defined as compounds of formula (I) wherein L is other than hydrogen, can generally be prepared by N-alkylating an intermediate of formula (I-a) with an intermediate of formula (IV), wherein W is an appropriate leaving group such as, for example, halo, e.g. fluoro, chloro, bromo, iodo, or in some instances W may also be a sulfonyloxy group, e.g. methanesulfonyloxy, benzenesulfonyloxy, trifluoromethanesulfonyloxy and the like reactive leaving groups. The compounds of formula (I-a) are defined as compounds of formula (I) wherein L represents hydrogen. The reaction can be performed in a reaction-inert solvent such as, for example, acetonitrile, 2-pentanol, isobutanol, dimethyl acetamide or DMF, and optionally in the presence of a suitable base such as, for example, sodium carbonate, potassium carbonate, N-methylpyrrolidone or triethylamine. Stirring may enhance the rate of the reaction. The reaction may conveniently be carried out at a temperature ranging between room temperature and the reflux temperature of the reaction mixture.

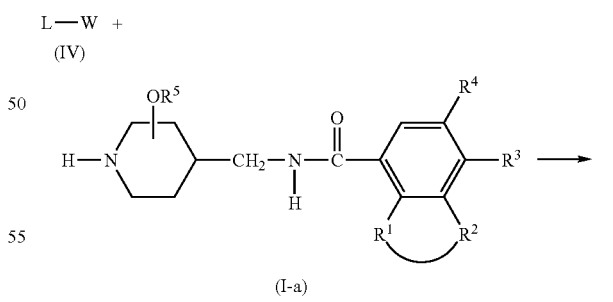

Alternatively, compounds of formula (I-b) can also be prepared by reductively N-alkylating a compound of formula (I-a) with an intermediate of formula L'=O (V), wherein L'=O represents a derivative of formula L-H wherein two geminal hydrogen atoms are replaced by oxygen, following art-known reductive N-alkylation procedures.

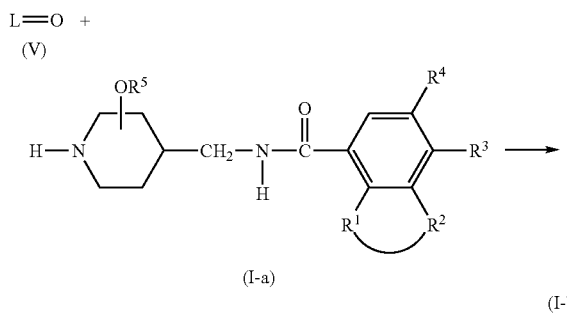

(I-a)  (I-b)

Said reductive N-alkylation can be performed in a reaction-inert solvent such as, for example, dichloromethane, ethanol, toluene or a mixture thereof, and in the presence of a reducing agent such as, for example, a borohydride, e.g. sodium borohydride, sodium cyanoborohydride or triacetoxy borohydride. It may also be convenient to use hydrogen as a reducing agent in combination with a suitable catalyst such as, for example, palladium-on-charcoal or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g., thiophene or quinoline-sulphur. To enhance the rate of the reaction, the temperature may be elevated in a range between room temperature and the reflux temperature of the reaction mixture and optionally the pressure of the hydrogen gas may be raised.

Compounds of formula (I-a) can be prepared by reacting an intermediate of formula (VI), wherein PG represents an appropriate art-known protective group, such as for example a tert-butoxycarbonyl or a benzyl group or a photoremovable group, with an acid of formula (III), or an appropriate reactive functional derivative thereof, such as for example carbonyl imidazole derivatives, and subsequent deprotection of the thus formed intermediate, i.e. removal of PG by art-known methods.

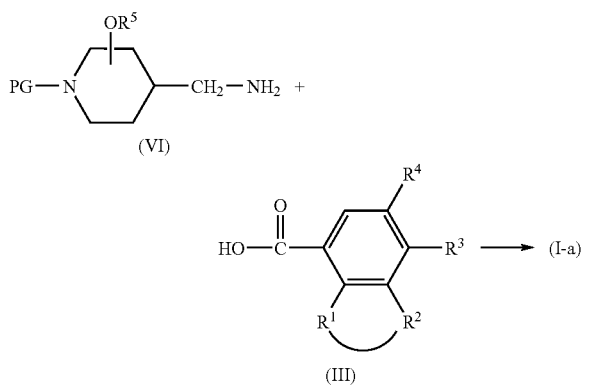

Compounds of formula (I-c), defined as compounds of formula (I) wherein $R^3$ is hydrogen and $R^4$ is amino, can generally be prepared N-alkylating an intermediate of formula (II) with an carboxylic acid derivative of formula (III-a). Said N-alkylation reaction may be performed by stirring the reactants in an appropriate solvent, optionally in the presence of a base, such as potassium carbonate or triethylamine. The N-alkylation reaction is then followed by a hydrogenation procedures using a suitable catalyst such as palladium-on-carbon.

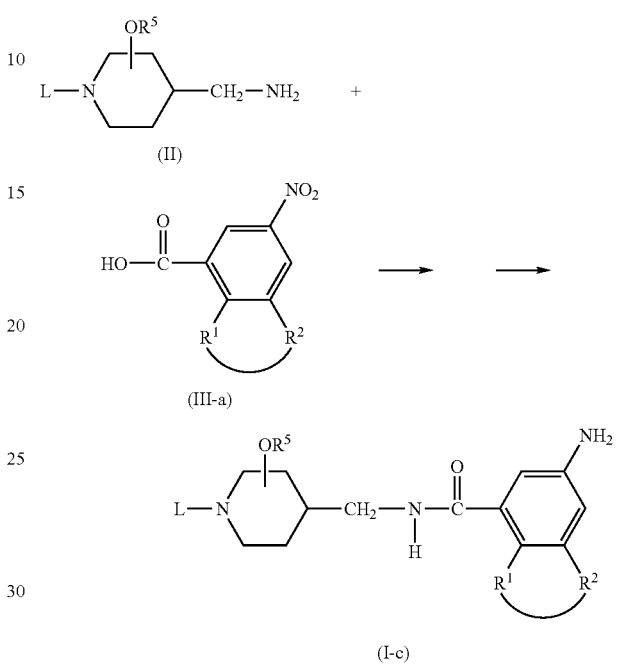

Compounds of formula (I-d), defined as compounds of formula (I) wherein $R^4$ is methylamino, can generally be prepared N-alkylating an intermediate of formula (II) with an carboxylic acid derivative of formula (III-b), wherein the PG-group is a protecting group that can be removed under acidic conditions such as e.g. tert-butyloxy-carbonyl. Said N-alkylation reaction may be performed by stirring the reactants in an appropriate solvent, optionally in the presence of a base, such as potassium carbonate or triethylamine. The N-alkylation reaction is then followed by a hydrolysis reaction under acidic conditions in order to remove the protecting group PG.

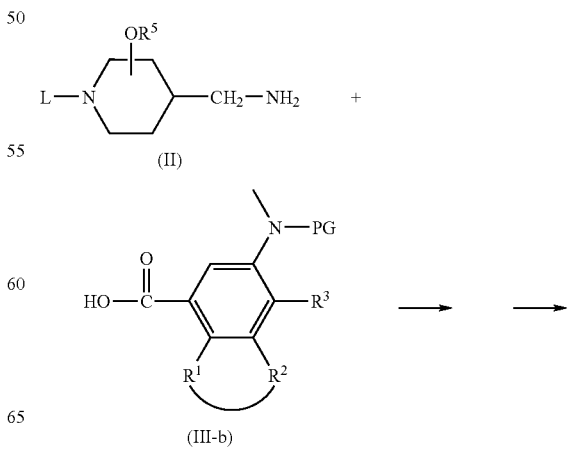

-continued

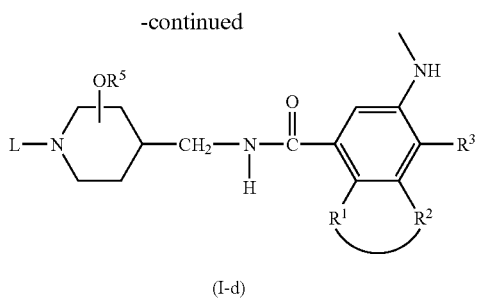

(I-d)

The compounds of formula (I) may further be prepared by converting compounds of formula (I) into each other according to art-known group transformation reactions.

The starting materials and some of the intermediates are known compounds and are commercially available or may be prepared according to conventional reaction procedures generally known in the art. For example, intermediates of formula (II) can be prepared according to the methodologies described in WO-99/02156 or WO-00/37461.

Intermediates of formula (VI) can be prepared according to the general methodology described in WO-99/02156 or WO-00/37461 for the therein described intermediates of formula (VIII).

The compounds of formula (I) as prepared in the hereinabove described processes may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the N-oxide forms, the pharmaceutically acceptable acid or base addition salts and stereoisomeric forms thereof possess 5HT$_4$-antagonistic properties as described in Example C.1.

Furthermore the compounds of formula (I) have shown improved metabolic stability over the structurally related compounds of WO-00/37461 as described in Example C.2. These advantegous metabolic stability properties result in a reduced risk of drug-drug interaction on the level of cytochrome P450 enzymes such as e.g. CYP1A2, CYP3A4, CYP2D6, CYP2C9 and CYP2C19 and therefore the present compounds have an improved drug safety profile. Furthermore these advantageous metabolic stability properties may allow for a once daily administration of the compounds of formula (I) instead of the usual administration of the active ingredient on a regimen of between two or four intakes per day thereby giving more patient compliance.

In view of the 5HT$_4$-antagonistic properties of the compounds of the present invention, the subject compounds may generally be used in the treatment or prophylaxis of gastrointestinal conditions such as hypermotility, irritable bowel syndrome (IBS), constipation- or diarrhea-predominant IBS, pain- and non-pain-predominant IBS, bowel hypersensitivity, and the reduction of pain associated with gastrointestinal hypersensitivity and/or hyperactivity.

It is also believed that the compounds of formula (I) are useful in the prevention or prophylaxis of a disturbed, hampered or impaired gastric accommodation such as dyspepsia. Dyspeptic symptoms are for example epigastric pressure, a lack of appetite, feeling of fullness, early satiety, nausea, vomiting, bloating and gaseous eructation.

The compounds of formula (I) may also be of use in the treatment of other 5HT$_4$-related disorders such as boulimia and hyperphagia.

In view of the utility of the compounds of formula (I), it follows that the present invention also provides a method of treating warm-blooded animals, including humans, (generally called herein patients) suffering from gastrointestinal conditions such as irritable bowel syndrome (IBS). Consequently a method of treatment is provided for relieving patients suffering from conditions such as hypermotility, irritable bowel syndrome (IBS), constipation- or diarrhea-predominant IBS, pain- and non-pain-predominant IBS, bowel hypersensitivity, and the reduction of pain associated with gastrointestinal hypersensitivity and/or hyperactivity.

The compounds of formula (I) may also be of potential use in other gastrointestinal disorders, such as those associated with upper gut motility. In particular, they are of potential use in the treatment of gastric symptoms of gastro-oesophageal reflux disease, such as heartburn (including episodic heartburn, nocturnal heartburn, and meal-induced heartburn).

Furthermore, the 5HT$_4$-antagonistic compounds of formula (I) may also be of potential use in the treatment or prophylaxis of bladder hypersensitivity, overactive bladder, lower urinary tract symptoms, benign prostatic hypertrophy (BPH), prostatis, detrusor hyperreflexia, outlet obstruction, urinary frequency, nocturia, urinary urgency, pelvic hypersensitivity, urge incontinence, urethritis, prostatodynia, cystitis, idiophatic bladder hypersensitivity, urinary incontinence or urinary incontinence associated with irritable bowel syndrome. In this respect, it may be advantegeous to combine the 5HT$_4$-antagonistic compounds of formula (I) with an alpha-adrenoceptor antagonist such as alfuzosin, indoramin, tamsulosin, doxazosin, terazosin, abanoquil, or prazosin in order to obtain pharmaceutical compositions comprising such an alpha-adrenoceptor antagonist, and a 5-HT$_4$-receptor antagonist of formula (I).

Hence, the present invention provides compounds of formula (I) for use as a medicine, and in particular the use of compounds of formula (I) for the manufacture of a medicine for treating gastrointestinal conditions such as hypermotility, IBS, constipation- or diarrhea-predominant IBS, pain- and non-pain predominant IBS, bowel hypersensitivity, and the reduction of pain associated with gastrointestinal hypersensitivity and/or hyperactivity. Both prophylactic and therapeutic treatment are envisaged.

In view of the 5HT$_4$-antagonistic properties of the compounds of the present invention, the subject compounds may also be of use in treating or preventing 5HT$_4$-related CNS disorders in a human. In particular, the compounds of formula (I) can be used to treat a variety of CNS disorders including but not limited to drug substance abuse, cognitive disorders such as Alzheimer's disease, senile dementia; behavioral disorders such as schizophrenia, mania, obsessive-compulsive disorder and psychoactive substance use disorders; mood disorders such as depression, bipolar affective disorder, anxiety and panic disorder; disorders of control of autonomic function such as hypertension and sleep disorders; obsessive/compulsive disorders including anorexia and bulimia, and neuropsychiatric disorders, such as Gilles de la Tourette's syndrome, and Huntington's disease.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions may take the form of solid dose forms, for example, tablets (both swallowable-only and chewable forms), capsules or gelcaps, prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants e.g. magnesium stearate, talc or silica); disintegrants (e.g. potato starch or sodium starch glycollate); or wetting agents (e.g. sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means, optionally with pharmaceutically acceptable additives such as suspending agents (e.g. sorbitol syrup, methylcellulose, hydroxypropyl methylcellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

Pharmaceutically acceptable sweeteners comprise preferably at least one intense sweetener such as saccharin, sodium or calcium saccharin, aspartame, acesulfame potassium, sodium cyclamate, alitame, a dihydrochalcone sweetener, monellin, stevioside or sucralose (4,1',6'-trichloro-4,1',6'-trideoxygalactosucrose), preferably saccharin, sodium or calcium saccharin, and optionally a bulk sweetener such as sorbitol, mannitol, fructose, sucrose, maltose, isomalt, glucose, hydrogenated glucose syrup, xylitol, caramel or honey.

Intense sweeteners are conveniently employed in low concentrations. For example, in the case of sodium saccharin, the concentration may range from 0.04% to 0.1% (w/v) based on the total volume of the final formulation, and preferably is about 0.06% in the low-dosage formulations and about 0.08% in the high-dosage ones. The bulk sweetener can effectively be used in larger quantities ranging from about 10% to about 35%, preferably from about 10% to 15% (w/v).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations stronger flavours may be required such as Caramel Chocolate flavour, Mint Cool flavour, Fantasy flavour and the like pharmaceutically acceptable strong flavours. Each flavour may be present in the final composition in a concentration ranging from 0.05% to 1% (w/v). Combinations of said strong flavours are advantageously used. Preferably a flavour is used that does not undergo any change or loss of taste and colour under the acidic conditions of the formulation.

The formulations of the present invention may optionally include an anti-flatulent, such as simethicone, alpha-D-galactosidase and the like.

The compounds of the invention may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example as a sparingly soluble salt.

The compounds of the invention may be formulated for parenteral administration by injection, conveniently intravenous, intramuscular or subcutaneous injection, for example by bolus injection or continuous intravenous infusion. Formulations for injection may be presented in unit dosage form e.g. in ampoules or in multidose containers, with an added preservative. The compositions may take such forms as suspensions, solutions or emulsions in oily or aqueous vehicles, and may contain formulatory agents such as isotonizing, suspending, stabilising and/or dispersing agents. Alternatively, the active ingredient may be in powder form for constitution with a suitable vehicle, e.g. sterile pyrogen-free water before use.

The compounds of the invention may also be formulated in rectal compositions such as suppositories or retention enemas, e.g. containing conventional suppository bases such as cocoa butter or other glycerides.

For intranasal administration the compounds of the invention may be used, for example, as a liquid spray, as a powder or in the form of drops.

In general it is contemplated that a therapeutically effective amount would be from about 0.0001 mg/kg to about 1 mg/kg body weight, preferably from about 0.001 mg/kg to about 0.5 mg/kg body weight.

EXPERIMENTAL PART

In the procedures described hereinafter the following abbreviations were used: "ACN" stands for acetonitrile; "THF", which stands for tetrahydrofuran; "DCM" stands for dichloromethane; "DIPE" stands for diisopropylether; "EtOAc" stands for ethyl acetate; "NH₄OAc" stands for ammonium acetate; "HOAc" stands for acetic acid; "MIK" stands for methyl isobutyl ketone, "DMF" stands for dimethylformamide and "DMA" stands for dimethylacetamide.

For some chemicals the chemical formula was used, e.g. NaOH for sodium hydroxide, $Na_2CO_3$ for sodium carbonate, $K_2CO_3$ for potassium carbonate, $H_2$ for hydrogen gas, $N_2$ for nitrogen gas, $CH_2Cl_2$ for dichloromethane, $CH_3OH$ for methanol, $NH_3$ for ammonia, HCl for hydrochloric acid, NaH for sodium hydride, $CaCO_3$ for calcium carbonate, and KOH for potassium hydroxide.

A. Preparation of the Intermediates

Example A.1 a) Preparation of

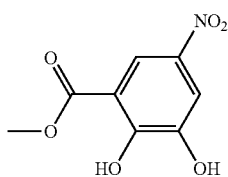

intermediate (1)

A mixture of 5-amino-2,3-dihydroxy benzoic acid (0.62 mol) in sulfuric acid (110 ml) and methanol (1100 ml) was stirred and refluxed for 24 hours. The reaction mixture stood overnight at room temperature. Then the mixture was concentrated and the residue was partitioned between DCM and water. The separated aqueous layer was washed with DCM and the separated organic layers were collected, dried, filtered and concentrated. The product was dried, yielding 120 g of intermediate (1).

b) Preparation of

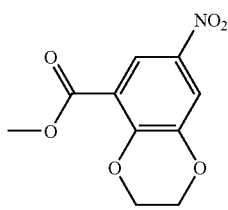

intermediate (2)

A mixture of intermediate (1) (0.35 mol), $K_2CO_3$ (0.77 mol) and tetrabutylammonium bromide (5 g) in 1,2-dibromoethane (42 ml), DMA (680 ml) and 2-propanone (1000 ml) was stirred and refluxed (70° C.) for 20 hours. Extra DMA (250 ml), tetrabutylammonium bromide (5 g) and 1-bromo-2-chloroethane (29 ml) was added. The reaction mixture was stirred and refluxed for 44 hours. Then the reaction mixture was allowed to cool to room temperature over weekend. The suspension was filtered and the filtrate was concentrated. The concentrate was partitioned between water and toluene. The separated aqueous layer was washed several times with DCM. The separated organic layers were combined, dried, filtered and concentrated. The residue was crystallized from DIPE and ACN, yielding 26 g of intermediate (2) (mp. 140° C.).

c) Preparation of

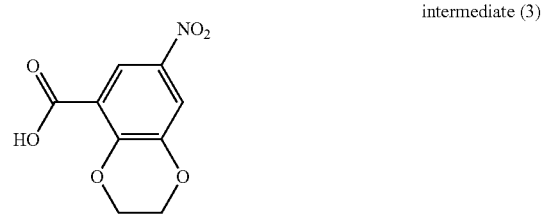

intermediate (3)

A mixture of intermediate (2) (0.063 mol) in NaOH 1N (100 ml) was stirred and refluxed for 4 hours. The reaction mixture was cooled on an ice-bath. A HCl-solution 1N (100 ml) was added to the formed precipitate. This reaction mixture was allowed to warm to room temperature and the formed precipitate was filtered and dried, yielding 14.5 g of intermediate (3) (mp. 234° C.).

Example A.2 a) Preparation of

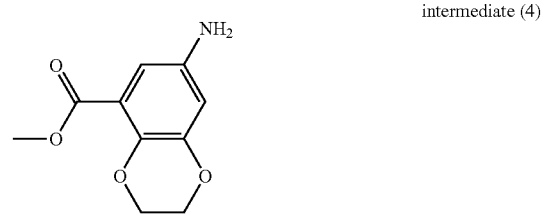

intermediate (4)

A mixture of intermediate (2) (0.089 mol) in methanol (500 ml) was hydrogenated at 50° C. with palladium-on-carbon (10%; 3 g) as a catalyst in the presence of thiophene solution (1 ml). After uptake of hydrogen (3 equivalents), the catalyst was filtered off over dicalite and the filtrate was evaporated, yielding 20.9 g of intermediate (4).

b) Preparation of

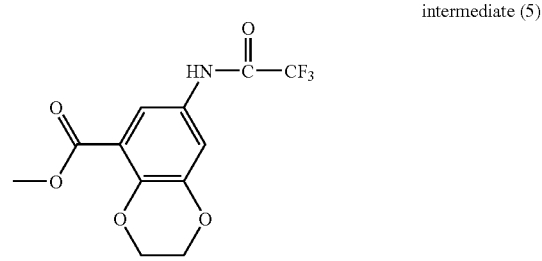

intermediate (5)

To a mixture of intermediate (4) (0.1 mol) in trichloromethane (130 ml), trifluoroacetic acid anhydride (0.11 mol) was added. The reaction mixture was stirred for 1 hour and the mixture was concentrated. The residue was purified over silica gel on a glas filter (eluent: $CH_2Cl_2/CH_3OH$ 90/10). The product fractions were collected and the filtrate was concentrated. The residue was purified by column chromatography over silica gel (eluent: $CH_2Cl_2/CH_3OH$ 98/2). The pure fractions were collected and the solvent was evaporated, yield 11.0 g of intermediate (5).

c) Preparation of

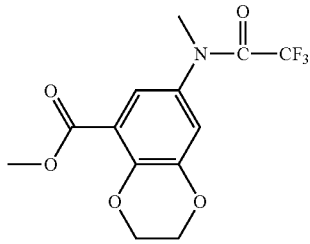

intermediate (6)

Intermediate (5) (0.036 mol) in DMF (100 ml) was stirred at room temperature under nitrogen flow. Sodium hydride 60% in paraffine (0.0432 mol) was added portionwise under nitrogen flow. This reaction mixture was warmed to 50° C. Then iodomethane (0.0432 mol) was added dropwise at 50° C. under nitrogen flow. This reaction mixture was stirred at 50° C. overnight, then the mixture was allowed to cool to room temperature and was poured out in water (680 ml), then extracted with toluene. The separated organic layer was dried, filtered and concentrated, yielding 10.8 g of intermediate (6).

d) Preparation of

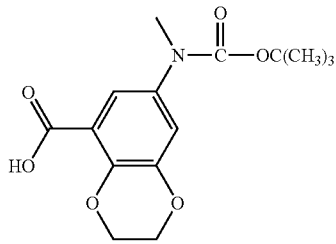

intermediate (7)

A mixture of intermediate (6) (0.0338 mol) in NaOH 1N (0.07 mol) and water (60 ml) was stirred and refluxed for 1 hour. The reaction mixture was allowed to cool to room temperature, then tert-butyl dicarbonate (0.041 mol) was added and the reaction mixture was stirred overnight at room temperature. Then HCl 1N (0.07 mol) was added and the residue was extracted with DCM. The separated organic layer was dried, filtered and concentrated, yielding 10.0 g of intermediate (7).

Example A.3 a) Preparation of

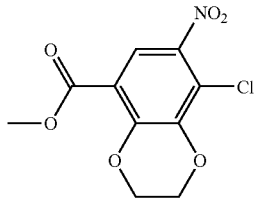

intermediate (8)

Methyl 8-cloro-2,3-dihydro-1,4-benzodioxin-5-carboxylic acid ester (0.44 mol) was dissolved in sulfuric acid (850 ml). This solution was cooled to below 0° C. Nitric acid (fuming, 0.44 mol) in sulfuric acid (200 ml) was added dropwise in 2 hours. The reaction mixture was stirred for 45 minutes at −10° C., then poured out into ice-water. Extraction with DCM yielded intermediate (8).

b) Preparation of

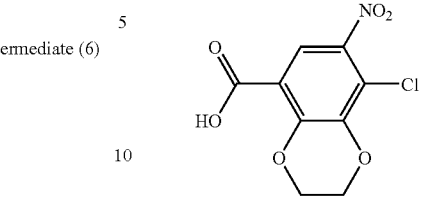

intermediate (9)

A mixture of intermediate (8) (0.20 mol) in THF (1000 ml) and NaOH (2N, 1000 ml) was stirred at room temperature for 5 hours. THF (700 ml) was removed by evaporation at 35° C. The aqueous layer was extracted with ethyl acetate (2×750 ml). The separated aqueous layer was cooled on an ice bath and acidified with concentrated HCl. The precipitate was filtered off, washed with water and dried, yielding 52 g of intermediate (9).

Example A.4 a) Preparation of

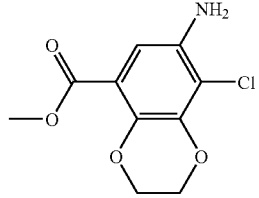

intermediate (10)

A mixture of intermediate (8) (0.095 mol) in THF (250 ml) was hydrogenated at 50° C. with platinum-on-carbon 5% (3 g) as a catalyst in the presence of thiophene solution (2 ml). After uptake of hydrogen (3 equivalents), the reaction mixture was filtered over celite and the filtrate was evaporated, yielding intermediate (10).

b) Preparation of

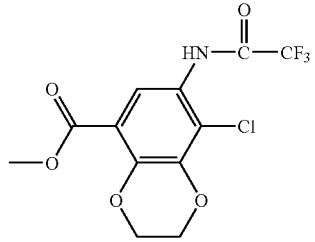

intermediate (11)

A solution of intermediate (10) (0.095 mol) in chloroform (200 ml) was cooled on a water bath, then trifluoroacetic acid anhydride (0.125 mol) was added dropwise in a period of 20 to 30 minutes, and the reaction mixture was stirred for 2 hours at room temperature. The solvent was evaporated, toluene (150 ml) was added and the mixture was concentrate until approximately 100 ml, then DIPE (300 ml) was added. The resulting precipitate was filtered off, washed with DIPE and dried, yielding 28.8 g of intermediate (11).

c) Preparation of

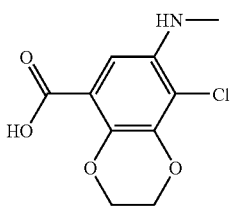

intermediate (12)

NaH (0.09 mol) was added portionwise at a temperature below 25° C. to a solution of intermediate (11) (0.084 mol) in N,N-dimethylformamide (150 ml) and the reaction mixture was stirred for 90 minutes at room temperature. Iodomethane (0.09 mol) was added dropwise and the mixture was stirred at room temperature for 20 minutes. The reaction mixture was poured out into HCl (400 ml, 5% aqueous solution, cold) and the mixture was extracted with DCM (2 times 350 ml). The organic layer was separated, washed with water, dried and the solvent was evaporated. The residue was dissolved in NaOH (200 ml, 2N) and THF (150 ml) and the reaction mixture was stirred and refluxed for 90 min. The organic solvent was evaporated and the aqueous, alkaline concentrate was cooled on ice and acidified with concentrated HCl. The precipitate was filtered off and dried, yielding 19.75 g intermediate (12).

Example A.5 a) Preparation of

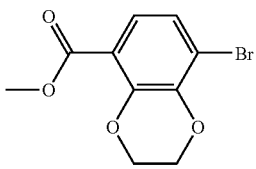

intermediate (13)

A mixture of methyl 8-amino-2,3-dihydro-1,4-benzodioxin-5-carboxylic acid ester (0.1 mol) in water (100 ml) was stirred at room temperature. Sulfuric acid (96%) (11 ml) was added dropwise at room temperature. A mixture of NaNO₂ (0.1 mol) in water (100 ml) was added dropwise at room temperature. The mixture was stirred at room temperature for 30 minutes to give mixture 1. A mixture of Cu(I)Br (0.15 mol) in an aqueous HBr (48%) solution (100 ml) and water (300 ml) was stirred at room temperature. Mixture 1 was added dropwise at room temperature. The mixture was stirred at room temperature for 30 minutes and then diluted with water (300 ml). The precipitate was filtered off, washed with water and diluted with CH₂Cl₂/CH₃OH/H₂O (300 ml/100 ml/300 ml). The solution was filtered over dicalite. The organic layer was separated, dried, filtered and the solvent was evaporated. The residue was suspended in DIPE/petroleumbenzin. The precipitate was filtered off and dried, yielding 23.2 g of methyl 8-bromo-2,3-dihydro-1,4-benzodioxin-5-carboxylate (intermediate 13).

b) Preparation of

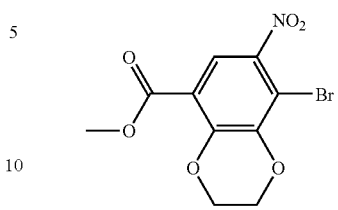

intermediate (14)

A solution of intermediate (13) (0.12 mol) in sulfuric acid (175 ml) was cooled to 0° C. A solution of nitric acid (0.12 mol) in sulfuric acid (175 ml) was added dropwise. The mixture was stirred at −10° C. for 10 minutes and poured out into ice water. The precipitate was filtered, washed with water and taken up in DCM. Water was added. The mixture was extracted with DCM. The organic layer was washed with water, dried, filtered and the solvent was evaporated, yielding 36 g of intermediate (14).

c) Preparation of

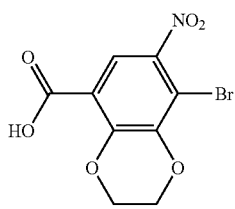

intermediate (15)

A mixture of intermediate (14) (0.055 mol) in NaOH (300 ml) and THF (300 ml) was stirred at room temperature overnight. NaOH was evaporated. Ethyl acetate was added. The mixture was extracted with ethyl acetate. The mixture was acidified with HCl. The precipitate was stirred, then filtered, washed with water (the minimum) and dried, yielding 14.3 g of intermediate (15).

Example A.6 a) Preparation of

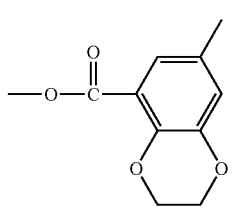

intermediate (16)

A mixture of methyl 2,3-dihydroxy-5-methylbenzoate (0.27 mol) and K₂CO₃ (0.6 mol) in 1,2-dibromoethane (0.4 mol) and acetone (1000 ml) was stirred and refluxed for 24 hours. The reaction mixture was cooled, filtered and the solvent was evaporated. The residue was taken up in DCM, washed with water and an aqueous 2N NaOH solution. The organic layer was dried, filtered and the solvent was evaporated, yielding 30.5 g of intermediate (16).

b) Preparation of

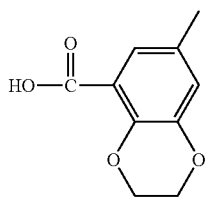
intermediate (17)

A solution of intermediate (16) (0.146 mol) in NaOH (2N) (400 ml) and THF (400 ml) was stirred and refluxed for 18 hours. The reaction mixture was cooled and THF was removed by evaporation. The residue was acidified with concentrated HCl. The resulting solid was filtered off, washed and dried, yielding 26.5 g of intermediate (17).

Example A.7 a) Preparation of

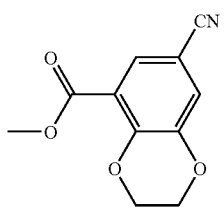
intermediate (18)

A solution of NaNO$_2$ (0.1314 mol) in H$_2$O (29.3 ml) was added dropwise at 0° C. to a mixture of intermediate (4) (0.1195 mol) in HCL 1.5N (190 ml). The mixture was stirred at 10° C. for 15 minutes and added dropwise at 5° C. to a mixture of CuCN (0.1673 mol) and KCN (0.2749 mol) in H$_2$O (293 ml). The mixture was stirred at 5° C. for 1 hour, then at 60° C. for 1 hour and 30 minutes, then cooled and filtered. The filtrate was extracted with diethyl ether. The organic layer was separated, dried, filtered, and the solvent was evaporated till dryness. The residue was washed with CH$_2$Cl$_2$/CH$_3$OH, dried, filtered, and the solvent was evaporated till dryness. The residue purified by column chromatography over silica gel (eluent: CH$_2$Cl$_2$/ethyl acetate 98/2). The pure fractions were collected and the solvent was evaporated till dryness, yielding 10.4 g of intermediate (18).

b) Preparation of

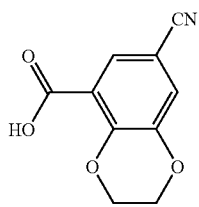
intermediate (19)

A mixture of intermediate (18) (0.0446 mol) and lithium-hydroxide monohydrate (0.0891 mol) in THF (300 ml) and water (300 ml) was stirred at room temperature for 20 hours. THF was partly evaporated. The mixture was acidified with HCl 3N and extracted with ethyl acetate. The organic layer was separated, dried, filtered, and the solvent was evaporated till dryness, yielding 9.4 g of intermediate (19).

Example A.8

Preparation of

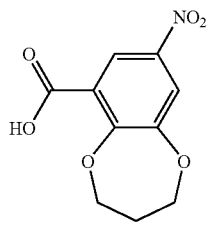
intermediate (21)

A mixture of intermediate (22) (0.12 mol) in NaOH 1N (200 ml) was stirred and refluxed for 4 hours. The reaction mixture stood overnight at room temperature, then cooled on an ice-bath and a HCl-solution 1N (200 ml) was added. The mixture was allowed to warm to room temperature and the formed precipitate was filtered, yielding 26.7 g of intermediate (21).

Example A.9 a) Preparation of

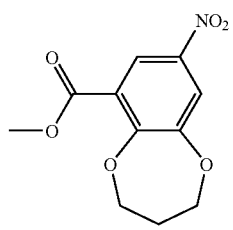
intermediate (22)

A mixture of 5-nitro-2,3-dihydroxybenzoic acid methylester (0.3 mol), potassium carbonate (0.66 mol), 1,3-dibromopropane (0.42 mol) and tetra-n-butylammonium bromide (4.5 g) in 2-propanone (900 ml) and DMA (600 ml) was stirred and refluxed for 30 hours. The reaction mixture was stirred for two days at room temperature and then filtered. The solvent was evaporated and the residue was partitioned between water and DCM. The separated organic layer was dried, filtered and concentrated. The residue was suspended in DIPE, filtered, dried and purified by column chromatography over silica gel (eluent: CH$_2$Cl$_2$/CH$_3$OH 98/2), yielding 33.5 g of intermediate (22).

b) Preparation of

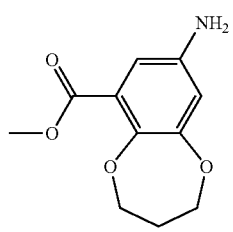
intermediate (23)

A mixture of intermediate (22) (0.11 mol) in THF (250 ml) was hydrogenated with palladium-on-carbon 10% (3 g) as a catalyst in the presence of a thiophene-solution (1 ml). After uptake of hydrogen (3 equivalents), the catalyst was filtered off over dicalite and the filtrate was concentrated, yielding 24.7 g of intermediate (23).

c) Preparation of

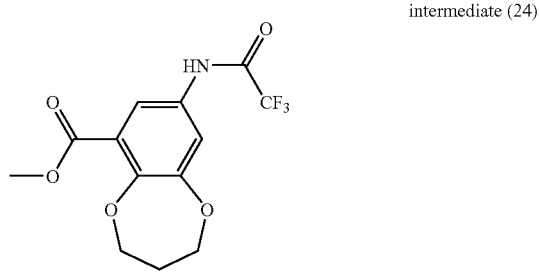
intermediate (24)

Intermediate (23) (0.11 mol) was dissolved in trichloromethane (500 ml) and the mixture was cooled on an ice-bath to a temperature below 10° C. Trifluoroacetic acid anhydride (0.14 mol) was added dropwise at the same temperature and then the reaction mixture was stirred for 1 hour at room temperature and then concentrated. The residue was crystallized from DIPE at room temperature overnight, yielding 5.8 g of intermediate (24).

d) Preparation of

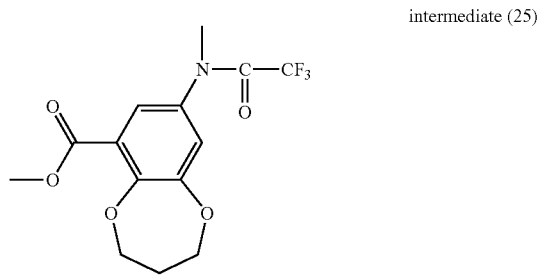
intermediate (25)

NaH 60% (0.046 mol) was added portionwise at room temperature to a mixture of intermediate (24) (0.131 mol) in DMF (140 ml) under a nitrogen flow. The mixture was stirred at room temperature for 1 hour. Iodomethane (0.046 mol) was added dropwise. The mixture was stirred at a temperature of 50° C. overnight, then cooled to room temperature, poured out into ice water and extracted with toluene. The organic layer was washed with water, dried, filtered and the solvent was evaporated. Petroleumether was added and decanted and the residue was warmed in petroleumether and again decanted. The residue was concentrated, yielding 12.8 g of intermediate (25).

e) Preparation of

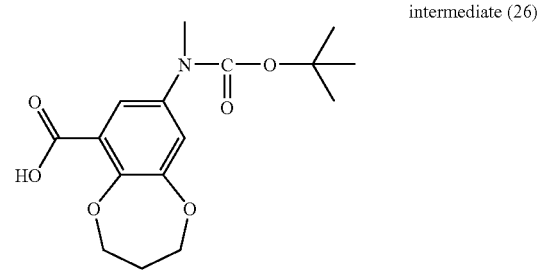
intermediate (26)

A mixture of intermediate (25) (0.0294 mol) in NaOH (1M, 0.059 mol) and water (60 ml) was stirred and refluxed for 1 hour. The reaction mixture was cooled on an ice-bath until room temperature. Then tert-butyl dicarbonate (0.036 mol) was added and the reaction mixture was stirred overnight at room temperature. HCl (1N, 0059 mol) was added and the product was extracted with DCM. The separated organic layer was dried, filtered and concentrated, yielding 10.8 g of intermediate (26).

Example A.10 a) Preparation of

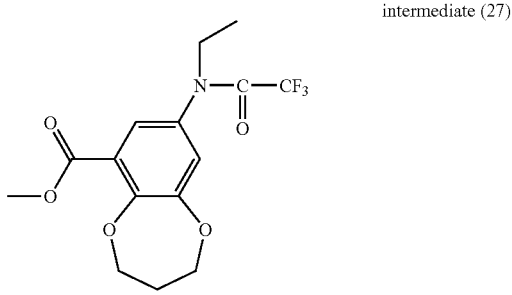
intermediate (27)

NaH 60% (0.171 mol) was added portionwise at room temperature to a mixture of intermediate (24) (0.131 mol) in DMF (450 ml) under a nitrogen flow. The mixture was stirred at room temperature for 1 hour. Iodoethane (0.171 mol) was added dropwise. The mixture was stirred at a temperature between 50 and 60° C. for 2 days, then cooled to room temperature, poured out into ice water and extracted with ethyl acetate. The organic layer was washed with water, dried, filtered and the solvent was evaporated. The residue was purified by column chromatography over silica gel (eluent: toluene/ethyl acetate 90/10), yielding 26.5 g of intermediate (27).

b) Preparation of

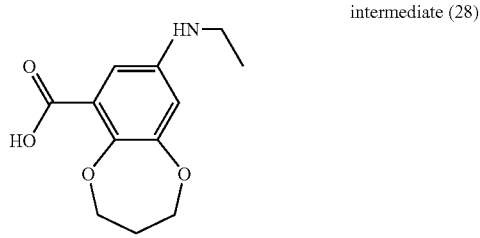
intermediate (28)

Lithiumhydroxide monohydrate (0.264 mol) was added portionwise at room temperature to a mixture of intermediate (27) (0.063 mol) in water (150 ml). The mixture was stirred at room temperature for 18 hours. Water (150 ml) was removed by evaporation. The mixture was acidified with HCl 3N till a pH=4 was obtained, then extracted with ethyl acetate. The organic layer was separated, dried, filtered, and the solvent was evaporated, yielding 14 g of intermediate (28).

Example A.11

Preparation of

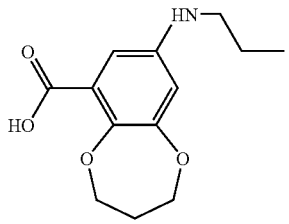

intermediate (29)

Intermediate (24) (0.0565 mol) was taken up in DMF (110 ml). NaH 60% (0.061 mol) was added portionwise. The mixture was stirred for 90 minutes at room temperature. 1-Iodopropane (0.061 mol) was added and the reaction mixture was stirred at 50-60° C. for 45 hours; then cooled. The mixture was poured into cold HCl (1N, 300 ml) and extracted with DCM (2×200 ml). The combined organic layer was washed with water, dried, filtered and the solvent was evaporated. The residue was purified by column chromatography over silica gel (eluent:hexaan/EtOAc 70/30). The desired fractions were collected and the solvent was evaporated. The residue was dissolved in THF (100 ml). An aqueous NaOH solution (2N, 125 ml) was added. The mixture was stirred overnight. The organic solvent was evaporated. The aqueous layer was washed with DCM, saturated with sodium chloride, cooled on an ice bath and acidified with a concentrated HCl solution to a pH of 3 to 4. Then the mixture was extracted with diethylether (4×100 ml). The combined organic layer was dried, filtered and the solvent was evaporated, yielding 6.5 g of intermediate (29).

Example A.12 a) Preparation of

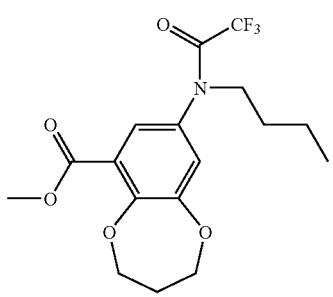

intermediate (30)

A mixture of intermediate (24) (0.166 mol) in DMF (350 ml) was stirred at room temperature. NaH (60%) (0.2 mol) was added portionwise. The mixture was stirred at room temperature for 1.5 hours, then heated to 50° C. 1-Iodobutane (0.2 mol) was added. The reaction mixture was stirred over the weekend at 50° C.; then cooled. Water was added and the mixture was extracted with toluene. The separated organic layer was dried, filtered and the solvent was evaporated. The residue was purified over silica gel on a glass filter (eluent: $CH_2Cl_2/CH_3OH$ 99/1). The desired fractions were collected and the solvent was evaporated, yielding 34 g of intermediate (30).

b) Preparation of

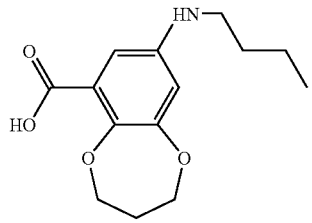

intermediate (31)

Intermediate (30) (0.09 mol) in NaH (10%) (400 ml) and THF (100 ml) was stirred at room temperature for 28 hours. The organic solvent was evaporated. The aqueous mixture was washed with DCM; then acidified with a concentrated HCl solution (pH 3 to 4) and extracted with DCM. The combined organic layers were dried, filtered and the solvent was evaporated, yielding 22 g of intermediate (31).

Example A.13 a) Preparation of

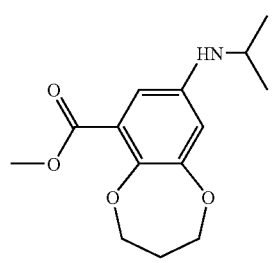

intermediate (32)

A mixture of intermediate (23) (0.2688 mol), 2-bromopropane (0.537 mol) and triethylamine (0.403 mol) in DMF (600 ml) was stirred at 130° C. overnight, then brought to room temperature. DMF was evaporated. The residue was taken up in ethyl acetate, poured out into ice water and extracted with ethyl acetate. The organic layer was washed with water, dried, filtered and the solvent was evaporated. The residue was purified by column chromatography over silica gel (eluent: cyclohexane/EtOAc 80/20). The pure fractions were collected and the solvent was evaporated, yielding 25 g of intermediate (32) (mp. 145° C.).

b) Preparation of

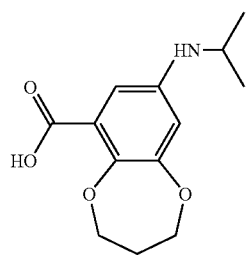

intermediate (33)

A mixture of intermediate (32) (0.0942 mol) in NaOH (200 ml, 2N) and THF (200 ml) was stirred at room temperature for 72 hours. The solvent was evaporated. Ethyl acetate was added. The mixture was extracted with ethyl acetate. The aqueous layer was acidified with HCl till pH 2 was obtained. The mixture was stirred. The precipitate was filtered, washed with a minimum of water and dried, yielding 22 g of intermediate (33), (mp. 203° C.).

Example A.14 a) Preparation of

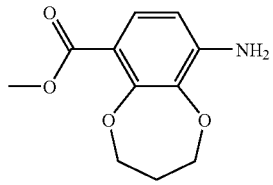

intermediate (34)

Sulfuric acid 97% (80 ml) was added carefully to a mixture of methyl 9-(acetylamino)-3,4-dihydro-2H-1,5-benzodioxepin-6-carboxylate (0.51 mol) in methanol (1000 ml). The mixture was stirred at 60° C. for 1 hour and then cooled. The solvent was evaporated. The residue was taken up in DCM. The mixture was washed with a KHCO₃ solution. The organic layer was separated, dried, filtered and the solvent was evaporated. The residue was suspended in DIPE and a small amount of ACN. The precipitate was filtered off, washed and dried, yielding 105 g of intermediate (34).

b) Preparation of

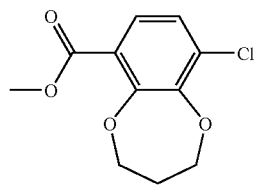

intermediate (35)

A mixture of intermediate (34) (0.24 mol) in water (240 ml) was stirred at 0° C. HCl (120 ml) was added dropwise at 0° C. The mixture was stirred for 15 minutes. A mixture of sodium nitrite (0.24 mol) in water (120 ml) was added dropwise at 0° C. The mixture was stirred at 0° C. for 30 minutes to give mixture (A). A mixture of copper chloride (0.24 mol) in HCl (120 ml) was added at room temperature. Mixture (A) was added dropwise. The reaction mixture was stirred at room temperature for 1 hour. The precipitate was filtered off and washed and dried, yielding 55.8 g of intermediate (35).

c) Preparation of

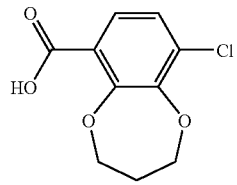

intermediate (36)

A mixture of intermediate (35) (0.22 mol) and KOH (2.2 mol) in water (1000 ml) was stirred and refluxed for 30 minutes and then cooled. The mixture was acidified with a concentrated HCl solution. The precipitate was filtered off, washed and dried, yielding 48 g of intermediate (36).

d) Preparation of

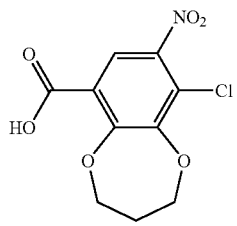

intermediate (37)

A mixture of intermediate (36) (0.01 mol) in sulfuric acid (20 ml) was cooled to −30° C., then a mixture of nitric acid (0.01 mol) in sulfuric acid (20 ml) was added dropwise at −30° C. and the reaction mixture was stirred for 5 minutes. The mixture was poured out into ice-water, the resulting precipitate was filtered off and washed with water, yielding intermediate (37).

Example A.15 a) Preparation of

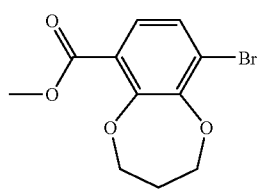

intermediate (38)

A mixture of intermediate (34) (0.27 mol) in water (270 ml) was stirred at room temperature. Sulfuric acid (97%) (30 ml) was added dropwise at room temperature. The mixture was stirred for 15 minutes. A mixture of sodium nitrite (0.27 mol) in water (270 ml) was added dropwise at room temperature. The mixture was stirred at room temperature for 30 minutes to give mixture (A). A mixture of copper(I)bromide (0.4 mol) in water (540 ml) and hydrobromic acid (270 ml) was stirred at room temperature. Mixture (A) was added dropwise at room temperature. The reaction mixture was stirred at room temperature for 1 hour. The precipitate was filtered off, washed with a diluted sulfuric acid solution and water and dried under reduced pressure overnight. The residue was taken up in DCM. The organic layer was separated, dried, filtered and the solvent was evaporated. The solid was dried under reduced pressure, yielding 71.5 g of intermediate (38).

b) Preparation of intermediate (39)

A solution of nitric acid (0.135 mol) in sulfuric acid (70 ml) was added dropwise at a temperature between 0 and 5° C. to a mixture of intermediate (38) (0.123 mol) in sulfuric acid (280 ml). The reaction mixture was stirred at 0° C. for 10 minutes, poured out into ice water and extracted with DCM. The organic layer was separated, dried, filtered, and the solvent was evaporated, yielding intermediate (39).

c) Preparation of

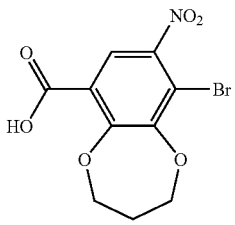

intermediate (40)

NaOH 2N (700 ml) was added at room temperature to a mixture of intermediate (39) (0.1205 mol) in THF (700 ml). The mixture was stirred at room temperature for 2 hours. NaOH was evaporated. Ethyl acetate was added. The aqueous layer was acidified with concentrated HCl. The precipitate was filtered, washed with a minimum of water and dried, yielding 36.5 g of intermediate (40).

Example A.16 a) Preparation of

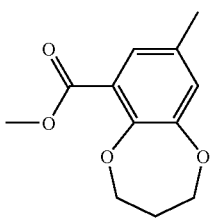

intermediate (41)

A mixture of methyl 2,3-dihydroxy-5-methylbenzoate (0.198 mol), 1,3-dibromopropane (0.198 mol) and $K_2CO_3$ (0.396 mol) in 2-propanone (360 ml) was stirred and refluxed for 6 hours, then cooled and the solvent was evaporated. The mixture was poured out into ice water and filtered. The filtrate was extracted with ethyl acetate. The organic layer was separated, dried, filtered, the solvent was evaporated and purified by column chromatography over silica gel (eluent: cyclohexane/ethyl acetate 80/20 to 70/30), yielding intermediate (41).

b) Preparation of

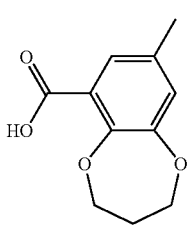

intermediate (42)

A mixture of intermediate (41) (0.1129 mol) in a mixture of a NaOH solution 2N (370 ml) and THF (370 ml) was stirred at room temperatue for 15 hours. THF was evaporated and the mixture was acidified with HCl 12N. The precipitate was filtered, washed with water and dried, yielding 21.9 g of intermediate (42) (mp. 74° C.).

Example A.17 a) Preparation of

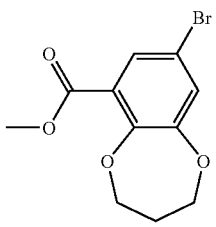

intermediate (45)

A mixture of 5-bromo-2,3-dihydroxy-benzoic acid methyl ester (0.397 mol) and $K_2CO_3$ (0.87 mol) in 1,3-dibromopropane (49 ml) and 2-propanone (1000 ml) was stirred and refluxed for 22 hours, then the reaction mixture was cooled, filtered over dicalite and the solvent was evaporated. The residue was partitioned between $NaHCO_3$ (5%, aq.) and DCM. The organic layer was separated, dried, filtered over dicalite and the solvent was evaporated, yielding 112 g intermediate (45).

b) Preparation of

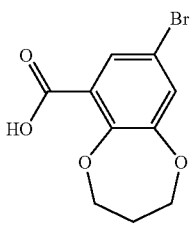

intermediate (46)

A mixture of intermediate (45) (0.14 mol) in THF (200 ml) and NaOH solution 2N (300 ml) was stirred at 30-60° C. for 4 hours, then the organic solvent was evaporated and the aqueous concentrate was cooled on ice and extracted with DCM. The aqueous layer was cooled further on ice, acidified to pH=1 and the solid residue was filtered off and dried, yielding 33 g of intermediate (46).

c) Preparation of

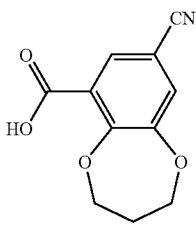

intermediate (47)

A mixture of intermediate (46) (0.33 mol) and copper(I) cyanide (2.7 mol) in DMA (800 ml) was stirred at 140° C. for 20 hours, then the reaction mixture was cooled and $FeCl_3.6H_2O$ (130 g), HCl (33 ml) and water (200 ml) were added. The mixture was stirred at 60° C. for 20 hours, cooled and poured out into water. Ethyl acetate was added and the layers were filtered to remove insoluble salts. The organic layer was separated, washed with water, dried, filtered and the solvent was evaporated. The residue was taken up in water and a 5% NaOH solution. was added, then the mixture was extracted with DIPE, acidified with HCl and extracted with ethyl acetate. The organic layer was separated, dried and the solvent was evaporated. The residue was purified by short column chromatography (eluent: CH$_2$Cl$_2$/CH$_3$OH 95/5+2 ml acetic acid), yielding 7 g of intermediate (47).

Example A.18 a) Preparation of

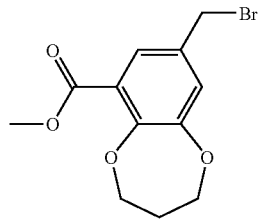
intermediate (48)

A mixture of intermediate (16) (0.126 mol), NBS (0.151 mol) and [1,1'-biphenyl]-2,2'dicarboxylic acid (0.0126 mol) in tetrachloromethane (500 ml) was stirred and refluxed for 5 hours, poured out into K$_2$CO$_3$ 10% and extracted with DCM. The organic layer was separated, dried, filtered, and the solvent was evaporated till dryness. The residue was purified by column chromatography over silica gel (eluent:CH$_2$Cl$_2$/cyclohexane 80/20 to 100/0), yielding 16.5 g of intermediate (48).

b) Preparation of

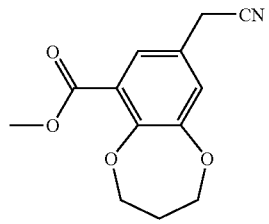
intermediate (49)

A mixture of intermediate (48) (0.048 mol) and NaCN (0.1096 mol) in DMSO (330 ml) was stirred at room temperature for 15 hours. K$_2$CO$_3$ (10%) was added. The mixture was extracted with ethyl acetate. The organic layer was separated, dried, filtered, and the solvent was evaporated. The residue was purified by column chromatography over silica gel (eluent: cyclohexane/ethyl acetate 70/30), yielding 10.8 g of intermediate (49).

c) Preparation of

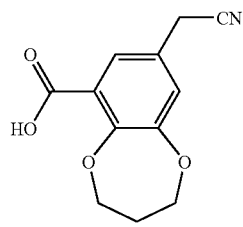
intermediate (50)

A mixture of intermediate (49) (0.0419 mol) and lithium-hydroxide monohydrate (0.0837 mol) in THF (100 ml) and water (100 ml) was stirred at room temperature for 5 hours. THF was evaporated. The mixture was acidified with a concentrated HCl solution and extracted with ethyl acetate. The organic layer was separated, dried, filtered, and the solvent was evaporated till dryness, yielding 9.8 g of intermediate (50).

Example A.19 a) Preparation of

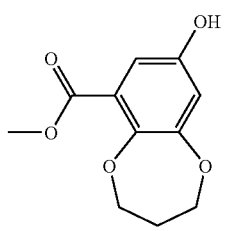
intermediate (51)

Intermediate (23) (0.0895 mol) was added portionwise at room temperature to a mixture of concentrated sulfuric acid (28 ml) in water (42 ml). Ice (70 g) was added. The mixture was stirred vigorously, then cooled to 0° C. A solution of NaNO$_2$ (0.0967 mol) in water (15 ml) was added at a temperature between 0° C. and 7° C. The mixture was stirred for 15 minutes, then added at a temperature between 5° C. and 7° C. to a hot solution (85° C.) of CuSO$_4$.5H$_2$O (0.358 mol) in water (250 ml) under a nitrogen flow. The mixture was stirred and refluxed for 30 minutes, then cooled, poured out into ice water and extracted with ethyl acetate. The organic layer was separated, dried, filtered, and the solvent was evaporated. The residue was purified by column chromatography over silica gel (eluent: toluene/ethyl acetate 80/20). Two fractions were collected and the solvent was evaporated, yielding 2.7 g of intermediate (51).

b) Preparation of

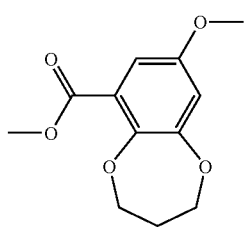
intermediate (52)

A mixture of intermediate (51) (0.012 mol), (CH$_3$)$_2$SO$_4$ (0.012 mol) and K$_2$CO$_3$ (0.0144 mol) in 2-propanone (30 ml) was stirred and refluxed for 4 hours, then cooled to room temperature and the solvent was evaporated till dryness. The residue was taken up in a mixture of DCM and water. The organic layer was separated, dried, filtered, and the solvent was evaporated, yielding 2.7 g of intermediate (52).

c) Preparation of

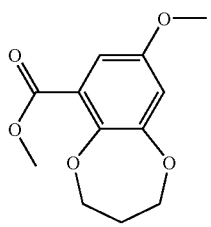

intermediate (53)

NaOH 2N (20 ml) was added at room temperature to a mixture of intermediate (52) (0.0113 mol) in THF (20 ml). The mixture was stirred at room temperature for 18 hours. THF was evaporated at 30° C. The aqueous layer was extracted twice with ethyl acetate, acidified with HCl 6N and extracted with ethyl acetate. The organic layer was separated, dried, filtered, and the solvent was evaporated, yielding 2.5 g of intermediate (53).

Example A.20 a) Preparation of

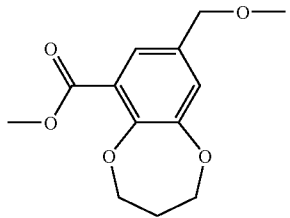

intermediate (54)

A mixture of intermediate (48) (0.11 mol) and CH$_3$ONa/CH$_3$OH 30% (0.44 mol) in methanol (330 ml) was stirred at 60° C. for 2 hours, then brought to room temperature and the solvent was evaporated till dryness. The residue was taken up in a mixture of water and DCM. The mixture was extracted with DCM. The organic layer was separated, dried, filtered, and the solvent was evaporated, yielding 24 g of intermediate (54).

b) Preparation of

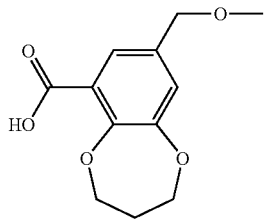

intermediate (55)

Lithiumhydroxide dihydrate (0.182 mol) was added dropwise at room temperature to a mixture of intermediate (54) (0.091 mol) in THF (20 ml) and water (200 ml). The mixture was stirred at room temperature overnight. THF was evaporated. Ethyl acetate was added. The mixture was extracted with ethyl acetate. The aqueous layer was acidified with concentrated HCl. DCM was added. The mixture was extracted with DCM. The organic layer was separated, dried, filtered, and the solvent was evaporated, yielding 21.5 g of intermediate (55).

Example A.21

Preparation of

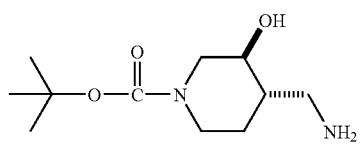

intermediate (56)

A mixture of 1,1-dimethylethyl(trans)-3-hydroxy-4-[[(phenylmethyl)amino]methyl]-1-piperidinecarboxylate [described in WO-00/37461 as intermediate (1-d)] (0.023 mol) in methanol (100 ml) was hydrogenated with palladium-on-carbon (10%, 1 g) as a catalyst. After uptake of hydrogen (1 equivalent), the catalyst was filtered off and the filtrate was evaporated. The residue was solidified in DIPE+ACN, filtered off and dried, yielding 4 g of 1,1-dimethylethyl(trans)-4-(aminomethyl)-3-hydroxy-1-piperidinecarboxylate (intermediate 56, mp. 178° C.).

In an analogous way, but starting from cis-3-hydroxy-4-piperidinemethanol (described in *J. Org. Chem.*, 34, pp. 3674-3676 (1969)), 1,1-dimethylethyl(cis)-4-(aminomethyl)-3-hydroxy-1-piperidinecarboxylate (intermediate 57) was prepared.

intermediate (57)

Example A.22 a) Preparation of intermediate (58)

1,1-Dimethylethyl(trans)-3-hydroxy-4-[[(phenylmethyl)amino]methyl]-1-piperidinecarboxylate [described in WO-00/37461 as intermediate (1-d)] (2.73 mol) was separated and purified by chiral column chromatography over Chiralcel AD (eluent:hexane/ethanol 80/20). The desired fractions were collected and the solvent was evaporated. Toluene was added and azeotroped on the rotary evaporator, yielding 377 g of 1,1-dimethylethyl(3S-trans)-3-hydroxy-4-[[(phenylmethyl)amino]methyl]-1-piperidinecarboxylate (intermediate 58).

b) Preparation of

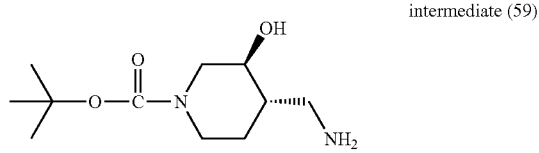
intermediate (59)

A mixture of intermediate (58) (0.028 mol) in methanol (100 ml) was hydrogenated with palladium-on-carbon (10%, 2 g) as a catalyst. After uptake of hydrogen (1 equivalent) the catalyst was filtered off and the filtrate was evaporated, yielding 4.7 g of 1,1-dimethylethyl(3S-trans)-4-(aminomethyl)-3-hydroxy-1-piperidinecarboxylate (intermediate (59); $[\alpha]^{20,D}$=+4.37° (c=24.03 mg/5 ml in $CH_3OH$)).

Example A.23 a) Preparation of

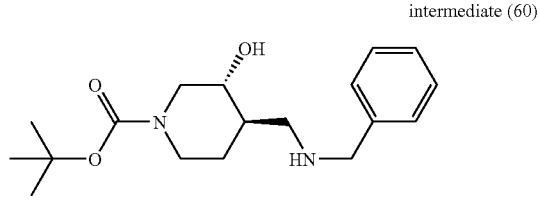
intermediate (60)

A mixture of 1,1-dimethylethyl(3R-trans)-3-hydroxy-4-[[(4-methylphenyl)-sulfonyl]oxymethyl]-1-piperidinecarboxylate [described in WO-00/37461 as intermediate (1-c-I)] (0.03 mol) and benzylamine (0.1 mol) in THF (250 ml) was stirred for 16 hours at 125° C. (autoclave). The reaction mixture was cooled and the solvent was evaporated. The residue was partitioned between DCM and an aqueous $K_2CO_3$ solution. The organic layer was separated, dried, filtered and the solvent was evaporated. The residue was crystallized from DIPE, yielding 5.3 g of 1,1-dimethyl-ethyl (3R-trans)-3-hydroxy-4-[[(phenylmethyl)amino]methyl]-1-piperidinecarboxylate (intermediate 60) ($[\alpha]^{20,D}$=−68.65° (c=23.16 mg/S ml in $CH_3OH$); mp. 91° C.).

b) Preparation of

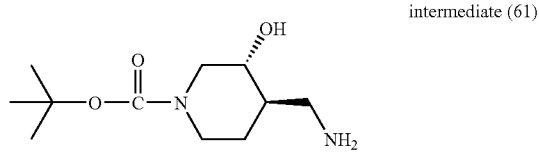
intermediate (61)

A mixture of intermediate (60) (0.016 mol) in methanol (150 ml) was hydrogenated with palladium-on-carbon (10%, 2 g) as a catalyst at a temperature of 50° C. After uptake of hydrogen (1 equivalent) the catalyst was filtered off and the filtrate was evaporated, yielding 1,1-dimethylethyl(3R-trans)-4-(aminomethyl)-3-hydroxy-1-piperidinecarboxylate (intermediate 61).

Example A.24 a) Preparation of

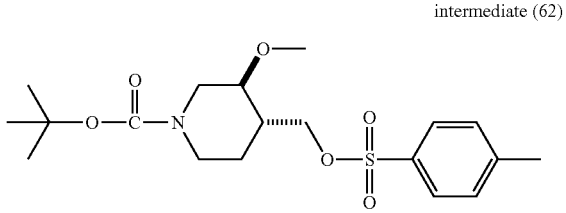
intermediate (62)

Reaction under nitrogen atmosphere. Sodiumhydride (0.3 mol) was added to a solution of 1,1-dimethylethyl trans-3-hydroxy-4-[[[(4-methylphenyl)sulfonyl]oxy]methyl]-1-piperidinecarboxylate [described in WO-00/37461 as intermediate (1-c)] (0.27 mol) in THF (1300 ml). The mixture was stirred for 30 minutes. Methyliodide (0.54 mol) was added and the resulting reaction mixture was stirred for 90 minutes. A small amount of water was added. The solvent was evaporated and the residue was partitioned between water and DCM. The organic layer was separated, dried, filtered and the solvent was evaporated, yielding 1,1-dimethylethyl trans-4-[[[(4-methylphenyl)sulfonyl]oxy]-methyl]-3-methoxy-1-piperidinecarboxylate (intermediate 62).

b) Preparation of

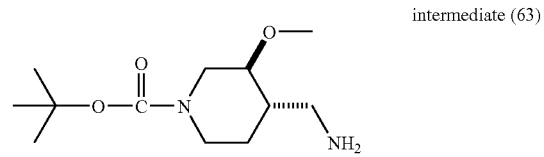
intermediate (63)

A mixture of intermediate (62) (0.065 mol) in THF (250 ml) was treated with liquid $NH_3$ in an autoclave at 125° C. during 16 hours. The reaction mixture was filtered and the filtrate was evaporated. The residue was partitioned between a 5% aqueous NaOH solution and DCM. The organic layer was separated, dried, filtered and the solvent was evaporated, yielding 16 g of 1,1-dimethylethyl(trans)-4-(aminomethyl)-3-methoxy-1-piperidinecarboxylate (intermediate (63).

Example A.25 a) Preparation of

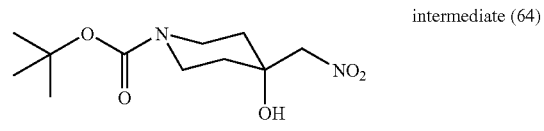
intermediate (64)

A mixture of tert-butyl 4-oxo-1-piperidinecarboxylate (0.1 mol) and nitro-methane (0.1 mol) in methanol (200 ml) was stirred at 10° C. Sodium methanolate (0.11 mol) was added dropwise at 10° C. The reaction mixture was stirred for 20 hours at room temperature. The solvent was evaporated. The residue was taken up into water, then neutralized with acetic acid, then extracted twice with DCM. The separated organic layer was washed with water, dried, filtered and the solvent evaporated. The residue was suspended in DIPE, filtered off, washed and dried, yielding 17.2 g of intermediate (64)(mp. 160° C.).

b) Preparation of

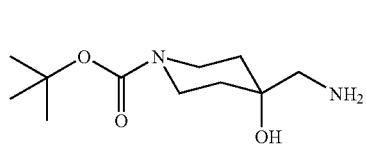
intermediate (65)

A mixture of intermediate (64) (0.058 mol) and acetic acid (12 ml) in methanol (250 ml) was hydrogenated at 14° C. with palladium-on-carbon (10%, 1 g) as a catalyst. After uptake of hydrogen (3 equivalents), the catalyst was filtered off and the filtrate was evaporated. The residue was taken up into ice/water, then alkalized with potassium hydroxide and salted out with $K_2CO_3$. This mixture was extracted twice with DCM. The separated organic layer was dried, filtered and the solvent evaporated. The residue was suspended in DIPE, filtered off, washed and dried, yielding 7.5 g of intermediate (65).

Example A.26 a) Preparation of

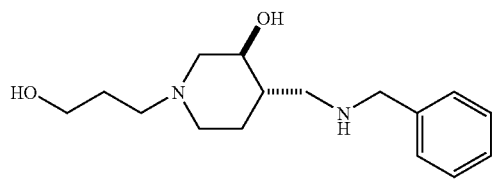
intermediate (66)

A mixture of (trans)-4-[[(phenylmethyl)amino]methyl]-3-piperidinol (prepared as intermediate (6) in WO-00/37461) (0.04 mol), 3-bromo-1-propanol (0.04 mol) and $Na_2CO_3$ (0.08 mol) in methylisobutyl ketone (400 ml) was stirred and refluxed for 18 hours. The solvent was evaporated. The residue was partitioned between water and DCM. The organic layer was separated, dried, filtered and the solvent was evaporated. The residue was purified by column chromatography over silica gel (eluent:$CH_2Cl_2$/($CH_3OH/NH_3$) 93/7). The desired fractions were collected and the solvent was evaporated. Toluene was added, then evaporated again, yielding 7.2 g of intermediate (66).

b) Preparation of

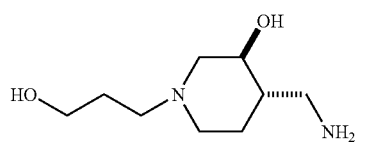
intermediate (67)

A mixture of intermediate (66) (0.026 mol) in methanol (150 ml) was hydrogenated with palladium-on-carbon (10%, 2 g) as a catalyst. After uptake of hydrogen (1 equivalent), the catalyst was filtered off and the filtrate was evaporated, yielding 4.4 g of intermediate (67).

Example A.27 a) Preparation of

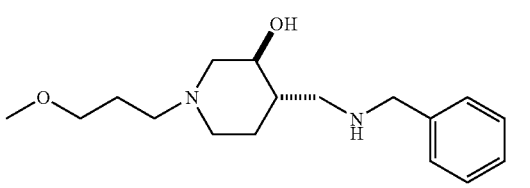
intermediate (68)

A mixture of (trans)-4-[[(phenylmethyl)amino]methyl]-3-piperidinol (prepared as intermediate (6) in WO-00/37461) (0.04 mol), 1-chloro-3-methoxypropane (0.04 mol) and $Na_2CO_3$ (0.08 mol) in methylisobutyl ketone (300 ml) was stirred and refluxed for 20 hours, then cooled and the solvent was evaporated. The residue was taken up into DCM, then washed with water, dried, filtered and the solvent was evaporated. The residue was purified by column chromatography over silica gel (eluent:$CH_2Cl_2$/($CH_3OH/NH_3$) 97/3). The pure fractions were collected and the solvent was evaporated, yielding 5 g of intermediate (68).

b) Preparation of

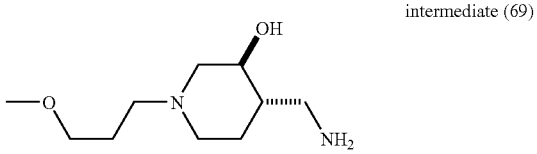
intermediate (69)

A mixture of intermediate (68) (0.016 mol) in methanol (150 ml) was hydrogenated with palladium-on-carbon (10%, 1 g) as a catalyst. After uptake of hydrogen (I equivalent), the catalyst was filtered off and the filtrate was evaporated, yielding 3.3 g of intermediate (69).

Example A.28 a) Preparation of

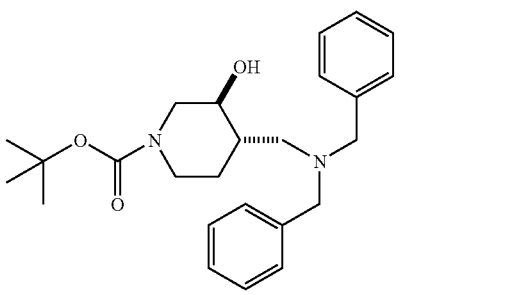
intermediate (70)

A mixture of 1,1-dimethylethyl(trans)-3-hydroxy-4-[[(phenylmethyl)amino]methyl]-1-piperidinecarboxylate (intermediate (1-d) in WO-99/02156) (0.426 mol), benzaldehyde (0.5 mol) and palladium-on-carbon (10%) (5 g) in a thiophene solution (5 ml) and methanol (1000 ml) was stirred at 70-80° C. overnight. The solvent was evaporated. The residue was partitioned between DCM (150 ml) and 5% aqueous NaOH (150 ml). The mixture was separated into its layers. The aqueous layer was extracted with DCM.

The combined organic layer was dried, filtered and the solvent was evaporated. The residue was purified by column chromatography over silica gel (eluent:CH$_2$Cl$_2$/(CH$_3$OH/NH$_3$) 90/10). The pure fractions were collected and the solvent was evaporated. The residue was crystallized from DIPE and a drop of ACN. The precipitate was filtered off and dried, yielding 2.35 g 1,1-dimethylethyl(trans)-4-[[bis(phenylmethyl)amino]methyl]-3-hydroxy-1-piperidinecarboxylate (intermediate 70), mp. 133° C.).

b) Preparation of

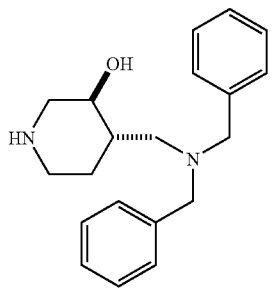

intermediate (71)

A mixture of intermediate (70) (0.284 mol) in 2-propanol (1000 ml) and a mixture of 6N HCL in 2-propanol (250 ml) was stirred and refluxed for 15 minutes and then cooled. The solvent was evaporated. A 5% aqueous NaOH solution (750 ml) was added. The mixture was extracted three times with DCM. The organic layer was separated, dried, filtered and the solvent was evaporated, yielding 88.95 g of (trans)-4-[[bis(phenylmethyl)amino]methyl]-3-piperidinol (intermediate 71).

c) Preparation of

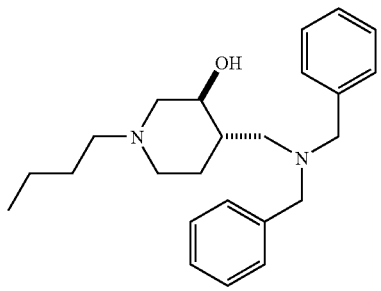

intermediate (72)

A mixture of intermediate (71) (0.083 mol) and butylaldehyde (7 g) in methanol (300 ml) was hydrogenated with palladium-on-carbon (10%) (2 g) as a catalyst in the presence of a thiophene solution (3 ml). After uptake of hydrogen (1 equivalent), the catalyst was filtered over celite and the filtrate was evaporated. The residue was dissolved in aqueous HCl 2N (500 ml). The mixture was washed with toluene and then separated into its layers. The aqueous layer was basified with 50% aqueous NaOH and then extracted three times with toluene. The combined organic layer was dried, filtered and the solvent was evaporated, yielding 29 g of (trans)-4-[[bis(phenylmethyl)amino]-methyl]-1-butyl-3-piperidinol (intermediate 72).

d) Preparation of

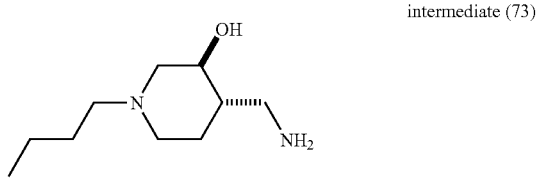

intermediate (73)

A mixture of intermediate (72) (0.079 mol) in methanol (250 ml) was hydrogenated with palladium-on-carbon (10%) (2 g) as a catalyst. After uptake of hydrogen (2 equivalents), the catalyst was filtered over celite and the filtrate was evaporated, yielding 13.8 g of (trans)-4-(aminomethyl)-1-butyl-3-piperidinol (intermediate 73).

Example A.29 a) Preparation of

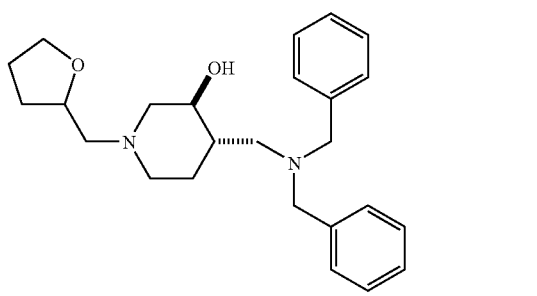

intermediate (74)

Intermediate (71) (0.0387 mol) dissolved in 2-methyl-propanol (200 ml). Tetrahydrofurfuryl methanesulfonate (0.05 mol) and Na$_2$CO$_3$ (0.0774 mol) were added. The reaction mixture was stirred and refluxed for 24 hours; then cooled. The precipitate was filtered off. The solvent was evaporated. The residue was purified by column chromatography over silica gel (eluent: CH$_2$Cl$_2$/CH$_3$OH 97/3). The desired fractions were collected and the solvent was evaporated, yielding 11.1 g of intermediate (74).

b) Preparation of

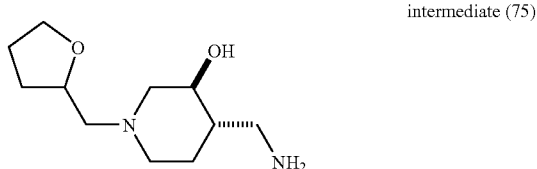

intermediate (75)

Intermediate (74) (0.0279 mol) in methanol (150 ml) was hydrogenated with palladium-on-carbon (10%, 2 g) as a catalyst. After uptake of hydrogen (2 equivalents), the catalyst was filtered off over dicalite and the solvent was evaporated, yielding 5.74 g of intermediate (75).

Example A.30 a) Preparation of

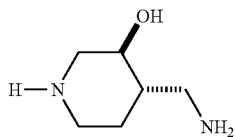
intermediate (76)

1,1-Dimethylethyl(trans)-4-(aminomethyl)-3-hydroxy-1-piperidinecarboxylate (prepared as intermediate (1-e) in WO-00/37461) (0.06 mol) in 2-propanol saturated with HCl (60 ml) and 2-propanol (400 ml) was stirred and refluxed for 30 minutes, then cooled. The solvent was evaporated and co-evaporated with toluene. The residue was dried, yielding 12 g of intermediate (76).

b) Preparation of

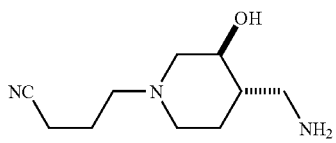
intermediate (77)

A mixture of 4-bromo-butanenitrile (0.06 mol), intermediate (76) (0.06 mol) and $Na_2CO_3$ (0.24 mol) in ACN (600 ml) was stirred and refluxed for 20 hours; then cooled and filtered. The solvent was evaporated. The residue was purified by column chromatography over silica gel (eluent: $CH_2Cl_2$/($CH_3OH/NH_3$) 85/15). The desired fractions were collected and the solvent was evaporated, yielding 4.5 g of intermediate (77).

Example A.31 a) Preparation of

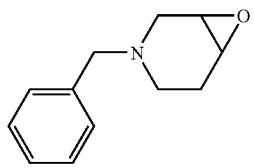
intermediate (78)

A mixture of trifluoroacetic acid (1.15 mol) in water (2000 ml) was stirred at room temperature. 1,2,3,6-Tetrahydro-1-(phenylmethyl)-pyridine (1.15 mol) was added dropwise to the mixture and the mixture was stirred at room temperature for 15 minutes. N-Bromosuccinimide (1.4 mol) was added portionwise and the mixture was warmed to 30-35° C. over 1 hour. The reaction mixture was stirred for 30 minutes. Again N-bromosuccinimide (0.085 mol) was added portionwise and the mixture warmed to 35° C. The reaction mixture was stirred overnight at room temperature and then decanted and added dropwise to a NaOH solution 20% (2000 ml). The mixture was stirred overnight at room temperature. The product was extracted with DCM (3×). The separated organic layer was dried, filtered and concentrated, yielding 193 g of intermediate (78).

b) Preparation of

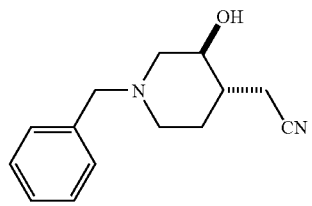
intermediate (79)

A mixture of lithium hydride (0.66 mol) in THF (600 ml, p.a) was reacted at room temperature under nitrogen, then a mixture of 2-hydroxy-2-methyl-propanenitrile (0.66 mol) in THF (150 ml) was added dropwise and the reaction mixture was stirred for 2 hours at room temperature, giving mixture (A). A mixture of intermediate (78) (0.6 mol) in THF (250 ml) was added dropwise to mixture (A) and after complete addition, the reaction mixture was stirred and refluxed for 4 hours, then stirred overnight at room temperature. DCM and water were added and the organic layer was separated, dried, filtered and the solvent was evaporated, yielding 128 g of intermediate (79).

c) Preparation of

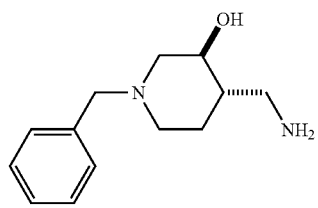
intermediate (80)

Intermediate (79) (0.6 mol) in $CH_3OH/NH_3$ (1.5 l) was hydrogenated at 14° C. with Raney Nicke as a catalyst. After uptake of hydrogen (2 equivalents), the catalyst was filtered off and the solvent was evaporated. The residue was dissolved in ACN and converted into the ethanedioic acid salt (1:1) with ethanedioic acid (0.6 ml). The solvent was decanted. The residue was suspended in 2-propanol. The precipitate was filtered off and taken up in methanol, boiled and cooled. The precipitate was filtered off, washed and dried, yielding 107 g of intermediate (80).

Example A.32

Preparation of

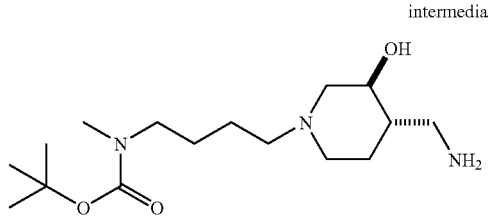
intermediate (81)

A mixture of 1,1-dimethylethyl methyl[4-[(methylsulfonyl)oxy]butyl]-carbamic acid ester (0.02 mol), intermediate (76) (0.02 mol) and $Na_2CO_3$ (0.08 mol) in ACN (100 ml) was

Example A.33 a) Preparation of intermediate (82)

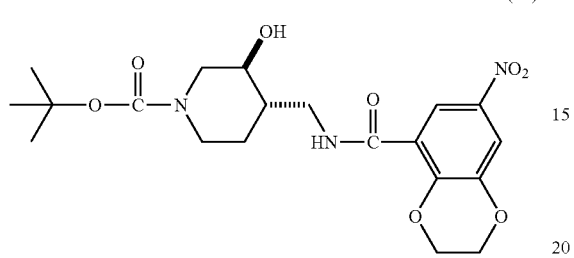

Intermediate (3) (0.146 mol) in DCM (400 ml) was stirred. Triethylamine (0.146 mol) was added. The reaction mixture was cooled to a temperature below 10° C. Formic acid (0.146 mol) was added dropwise at this temperature and the reaction mixture was stirred at this temperature for 1 hour (=mixture A). Intermediate (56) (0.146 mol) in DCM (400 ml) was stirred at room temperature for 1 hour; then added to mixture (A). The reaction mixture was stirred for 90 minutes at room temperature. Water was added. The separated organic layer was dried, filtered and the solvent was evaporated, yielding 81 g of intermediate (82).

b) Preparation of intermediate (83)

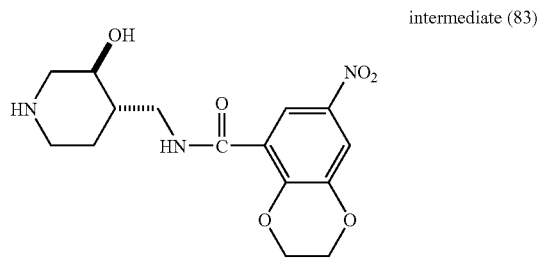

Intermediate (82) (0.15 mol) in 2-propanol/HCl 6N (120 ml) and 2-propanol (1200 ml) was stirred and refluxed for 2 hours. The reaction mixture was allowed to cool to room temperature overnight. The formed precipitate was filtered off and dried, yielding 54.5 g of intermediate (83), (mp. 150° C.).

In an analogous way, intermediates (84) and (85) were prepared.

intermediate (84)

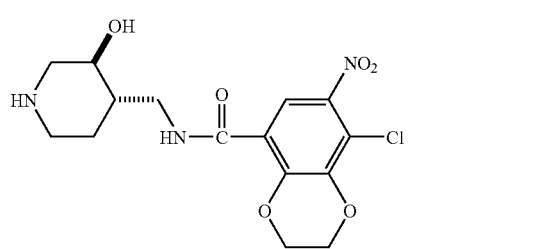

-continued intermediate (85)

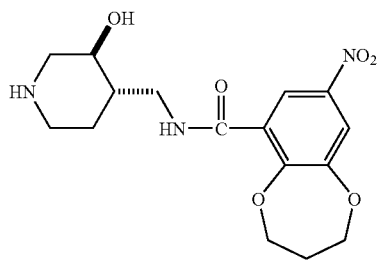

Example A.34 a) Preparation of intermediate (86)

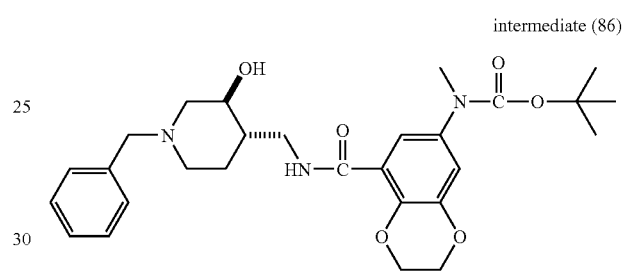

A mixture of intermediate (7) (0.08 mol) in DCM (400 ml) and triethylamine (0.1 mol) was stirred at 5° C. Formic acid (0.08 mol) was added dropwise. The mixture was stirred for 30 minutes at 5° C. Intermediate (80) (0.08 mol) and triethylamine (0.25 mol) in DCM (400 ml) were added at 5° C. The reaction mixture was allowed to warm to room temperature and washed with water. The separated organic layer was dried, filtered and the solvent was evaporated and coevaporated with toluene, yielding 41 g of intermediate (86).

b) Preparation of intermediate (87)

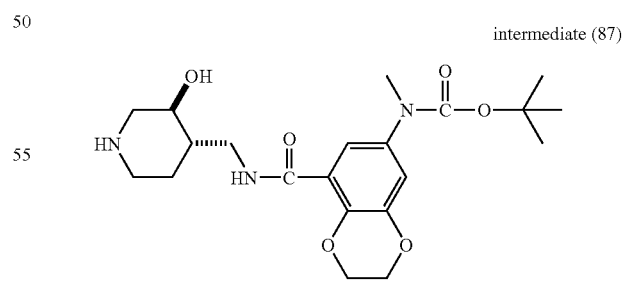

Intermediate (86) (0.08 mol) in methanol (250 ml) was hydrogenated with palladium-on-carbon (10%, 2 g) as a catalyst. After uptake of hydrogen (1 equivalent), the catalyst was filtered off and the solvent was evaporated, yielding 34 g of intermediate (87).

In an analogous way, intermediate (88) was prepared.

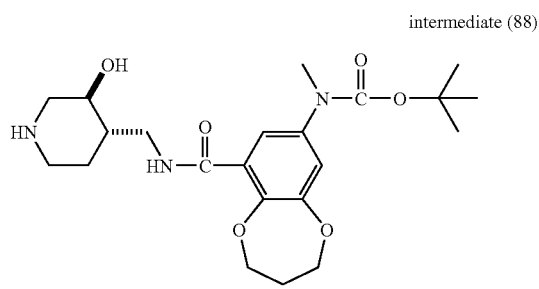
intermediate (88)

Example A.35

Preparation of

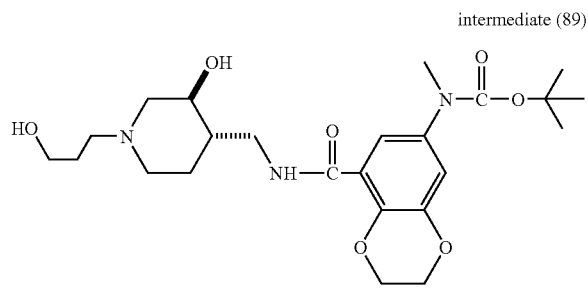
intermediate (89)

Intermediate (7) (0.013 mol) in DCM (100 ml) was stirred. Triethylamine (0.015 mol) was added and the mixture was stirred at 5° C. Formic acid (0.013 mol) was added dropwise at 5° C.; then the reaction mixture was stirred at 5° C. for 30 minutes. Triethylamine (0.03 mol) and intermediate (67) (0.013 mol) in DCM (100 ml) were added at 5° C. The reaction mixture was allowed to warm to room temperature, then washed with water. The separated organic layer was dried, filtered and the solvent was evaporated, yielding 5.3 g of intermediate (89).

Example A.36 a) Preparation of

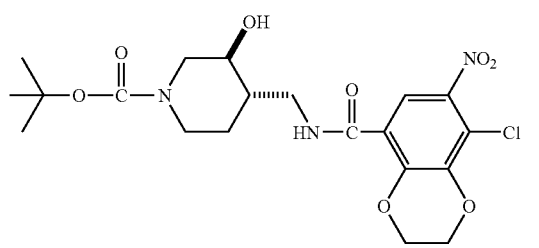
intermediate (90)

Intermediate (9) (0.06 mol) was added to DCM (250 ml). Triethylamine (8.4 ml) was added and the mixture was cooled to −5° C. Formic acid (0.06 mol) was added dropwise in 5 minutes. The reaction mixture was stirred for 40 minutes at a temperature ranging between −5 and −10° C. Intermediate (56) (0.06 mol) in DCM (50 ml) and triethylamine (8.4 ml) were added at once. The ice bath was removed and the mixture was stirred at room temperature for 2 hours. DCM (200 ml) was added. The mixture was washed with water/NaOH (5% aq)/water/cold HCl (5% aqueous)/water. The separated organic layer was dried, filtered and the solvent was evaporated. The residue was triturated under DIPE/ACN. The precipitate was filtered off and dried, yielding 23.2 g of intermediate (90).

b) Preparation of

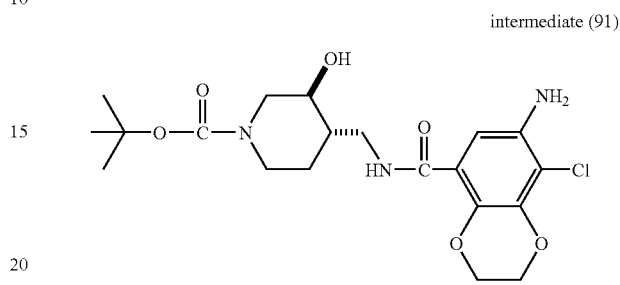
intermediate (91)

Intermediate (90) (0.0478 mol) in methanol (250 ml) was hydrogenated at 50° C. with platinum-on-carbon (5%, 3 g) as a catalyst in the presence of thiophene solution (3 ml). After uptake of hydrogen (3 equivalents), the catalyst was filtered off over dicalite and the solvent was evaporated. The residue was triturated under DIPE. The precipitate was filtered off and dried, yielding 19.7 g of intermediate (91) (mp. 161° C.).

In an analogous way, intermediates (92), (93) and (94) were prepared.

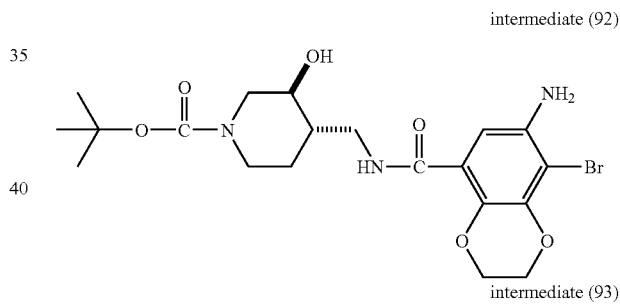
intermediate (92)

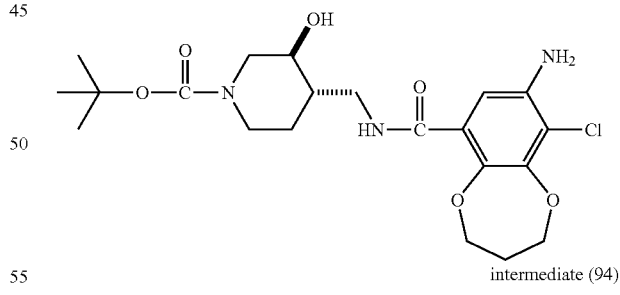
intermediate (93)

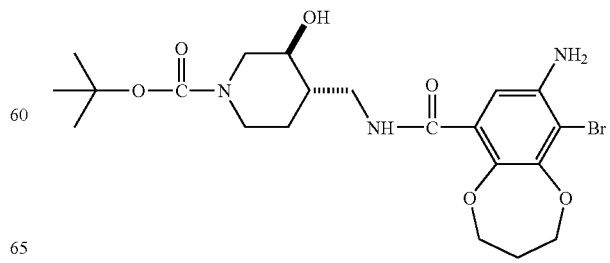
intermediate (94)

Example A.37

Preparation of (intermediate 95)

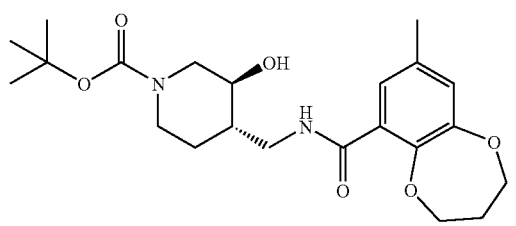

A mixture of intermediate (17) (0.336 mol) and triethylamine (0.4 mol) in DCM (1000 ml) was stirred at 5° C., then ethyl chloroformate (0.35 mol) was added dropwise and the reaction mixture was stirred for 30 minutes. To this mixture, a solution of intermediate (59) (83 g) in DCM (1000 ml) was added at 5° C., then the reaction mixture was allowed to reach room temperature and was washed with water. The organic layer was separated, dried, filtered and the solvent was evaporated, yielding 150 g of intermediate (95).

TABLE I-1 intermediates (96) to (114) were prepared according to the same procedure of Example A.38

| Intm. | Structure | Physical data |
|---|---|---|
| 97 | 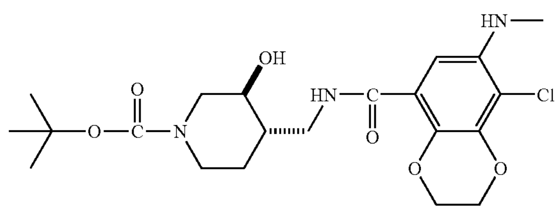 | trans; |
| 98 | 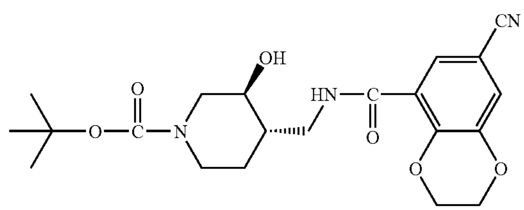 | 3S-trans; |
| 99 | 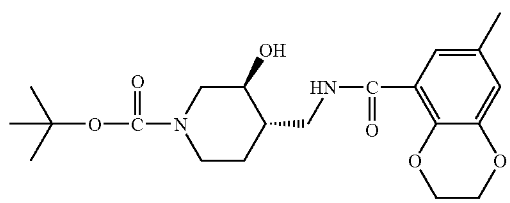 | 3S-trans; |
| 100 | 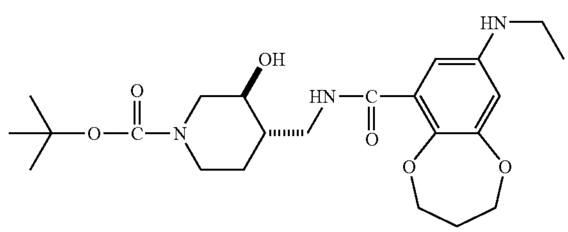 | trans; |
| 101 | 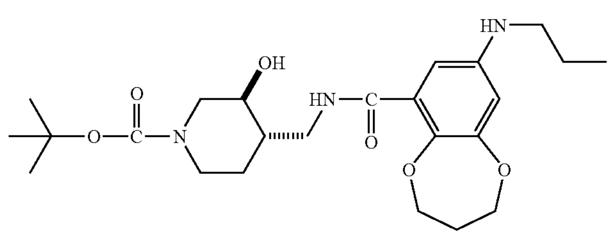 | trans; |

TABLE I-1-continued intermediates (96) to (114) were prepared according to the same procedure of Example A.38

| Intm. | Structure | Physical data |
|---|---|---|
| 102 | 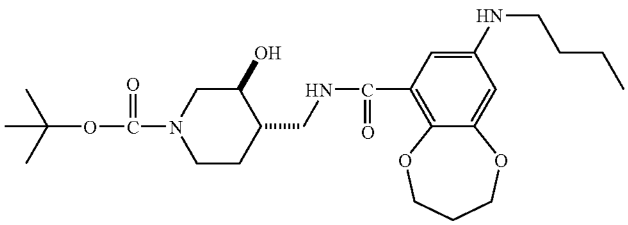 | trans; |
| 103 | 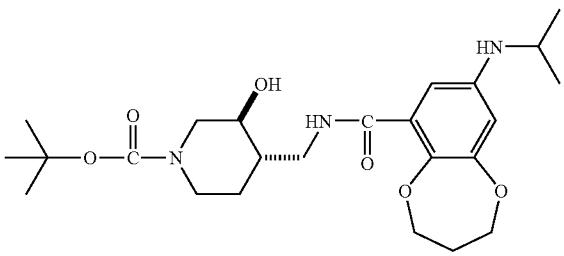 | trans; mp. 175° C. |
| 104 | 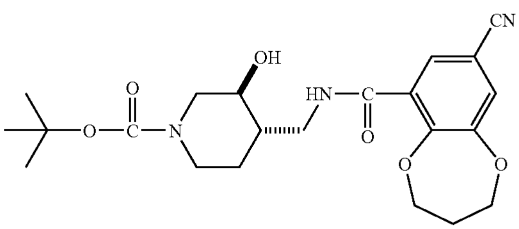 | trans; |
| 105 | 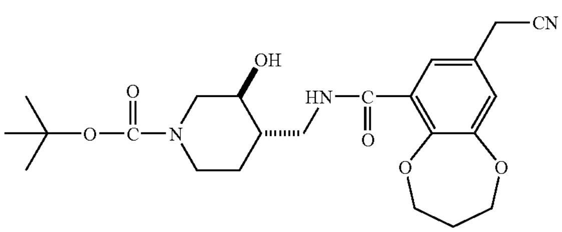 | trans; |
| 106 | 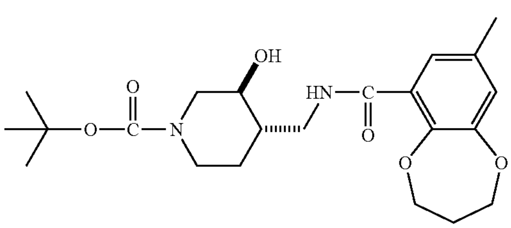 | trans; |
| 107 | 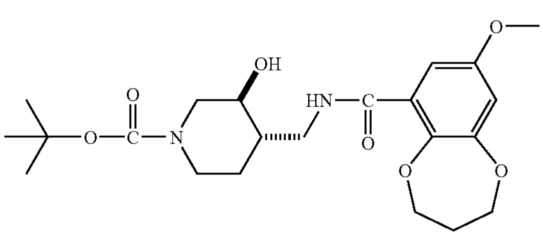 | trans; |

TABLE I-1-continued intermediates (96) to (114) were prepared according to the same procedure of Example A.38

| Intm. | Structure | Physical data |
|---|---|---|
| 108 | 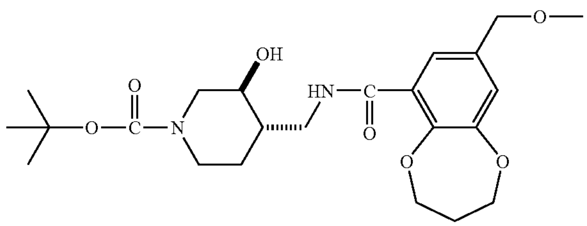 | trans; |
| 109 | 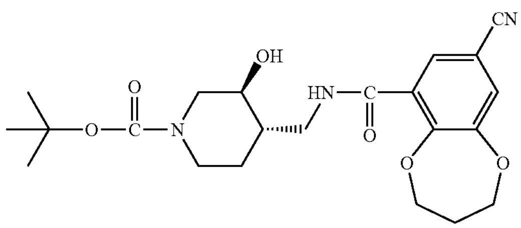 | 3S-trans; |
| 110 | 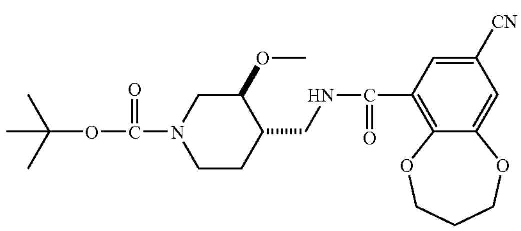 | trans; |
| 111 | 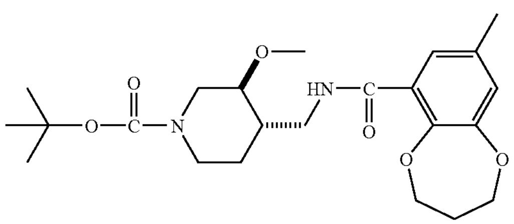 | trans; |
| 112 | 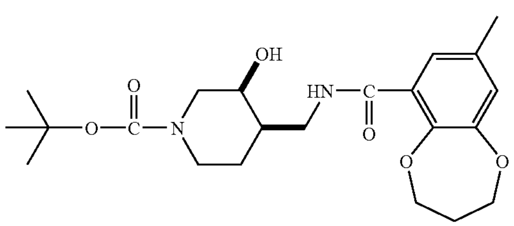 | cis; |
| 113 | 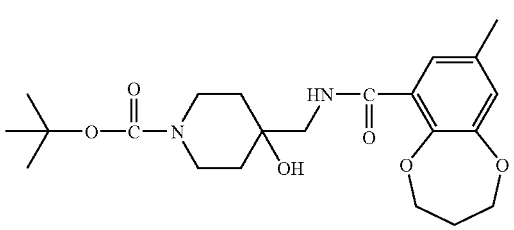 | |

TABLE I-1-continued intermediates (96) to (114) were prepared according to the same procedure of Example A.38

| Intm. | Structure | Physical data |
|---|---|---|
| 114 | 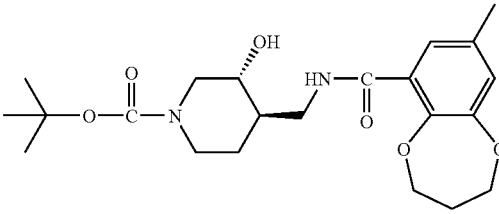 | 3R-trans; |

Example A.38

Preparation of

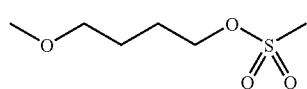 intermediate (115)

4-Methoxy 1-butanol (0.9 mol) was stirred in DCM (1500 ml) and triethylamine (1.35 mol) was added, then methylsulfonyl chloride (1.1 mol) was added dropwise (temperature rise up to 40° C.) and the reaction mixture was stirred for 2 hours at room temperature. The mixture was washed with water. The organic layer was separated, dried and the solvent was evaporated, then co-evaporated with toluene, yielding 167 g of intermediate (115).

Example A.39

Preparation of

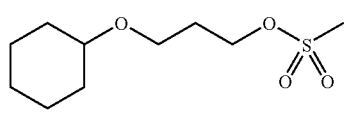 intermediate (116)

Triethylamine (0.11 mol) was added to a mixture of 3-cyclohexyloxypropan-1-ol (0.063 mol) in DCM (120 ml), then methylsulfonyl chloride (0.07 mol) was added dropwise and the reaction mixture was stirred at room temperature for 1 hour. The mixture was washed with an aqueous Na$_2$CO$_3$ solution and with water. The organic layer was separated, dried, filtered off and the solvent was evaporated. The residue was purified by column chromatography over silica gel (eluent: CH$_2$Cl$_2$/CH$_3$OH 99/1). The product fractions were collected and the solvent was evaporated, then co-evaporated with toluene, yielding 8.6 g of intermediate (116).

Example A.40 a) Preparation of

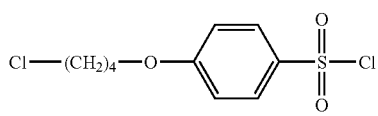 intermediate (117)

A mixture of 4-phenoxybutyl chloride (0.135 mol) in DCM (50 ml) was stirred and cooled to 0° C. Chlorosulftnic acid (0.149 mol) was added dropwise in 45 minutes. The ice bath was removed and the reaction mixture was stirred at room temperature for 2 hours. Then, ethanedioyl dichloride (0.176 mol) was added dropwise, followed by DMF (2 ml). The reaction mixture was stirred at room temperature for 20 hours. Then, the mixture was poured out on ice, extracted with DCM, dried and the solvent was evaporated, yielding intermediate (117).

b) Preparation of

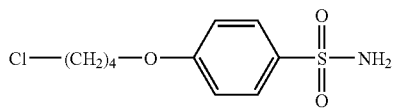 intermediate (118)

A solution of intermediate (117) (0.135 mol) in THF (500 ml) was stirred and cooled to 0° C. then, ammonia (gas) was bubbled through the solution. The reaction mixture was filtered and the solvent was evaporated. DCM (600 ml) was added to the residue and the mixture was washed with HCl (600 ml, 1N). The aqueous layer was separated and extracted with DCM (2 times 300 ml). The combined organic layers were washed with brine, dried and the solvent was evaporated. The residue was crystallised from CH$_3$OH/DIPE, filtered off and dried, yielding 18.5 g of intermediate (118).

In an analogous way, but starting from 4-phenoxypropyl chloride or 4-phenoxyethyl chloride, intermediates (119) and (120) were prepared.

intermediate (119)

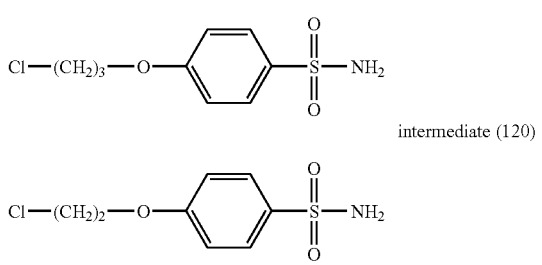

intermediate (120)

Example A.41

Preparation of intermediate (121)

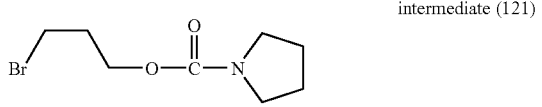

1-Pyrrolidinecarbonyl chloride (0.037 mol) was dissolved in tetrachloromethane (12 ml). 3-Bromo-1-propanol (0.036 mol) was added dropwise and the reaction mixture was stirred at room temperature for 7 days. The mixture was cooled on ice and $CH_3OH/(NH_3)$ (2 ml) was added. Then, DCM (100 ml) was added and the mixture was washed with water, dried and the solvent was evaporated. The residue was purified over silica gel on a glass filter (eluent: DCM). The product fractions were collected and the solvent was evaporated, yielding 4 g of intermediate (121).

Example A.42 a) Preparation of

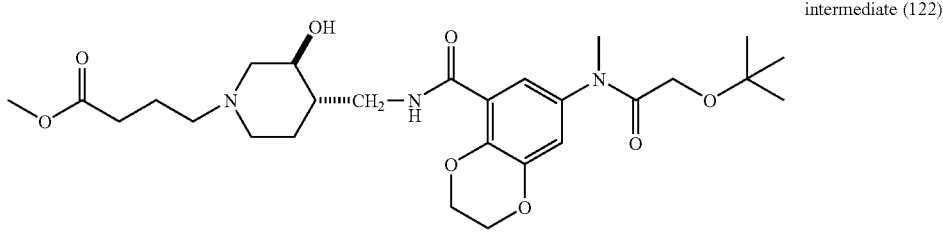

intermediate (122)

A mixture of intermediate (87) (0.0154 mol), 4-bromobutanoic acid, methyl ester (0.02 mol) and triethylamine (0.02 mol) in DMF (150 ml) was stirred overnight at 70° C. The reaction mixture was cooled and the solvent was evaporated. The residue was taken up in DCM and washed with water. The separated organic layer was dried, filtered and the solvent was evaporated, yielding 8 g of intermediate (122).

b) Preparation of intermediate (123)

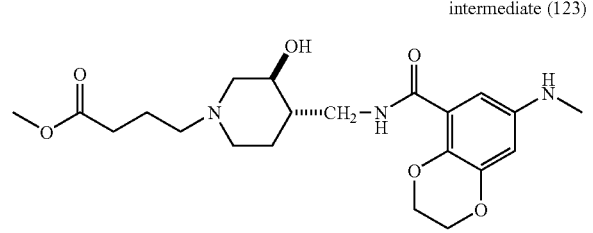

Intermediate (122) (0.0154 mol) in HCl/2-propanol (6N) (0.09 mol) and methanol (100 ml) was stirred and refluxed for 1 hour. The reaction mixture was cooled. The solvent was evaporated. The residue was taken up in DCM and washed with $H_2O/NH_3$. The separated organic layer was dried, filtered and the solvent was evaporated. The residue was purified by column chromatography over silica gel (eluent: $CH_2Cl_2/(CH_3OH/NH_3)$ 97/3). The desired fractions were collected and the solvent was evaporated, yielding 1.75 g of intermediate (123).

In an analogous way, intermediates (124) to (129) were prepared.

intermediate (124)

intermediate (125)

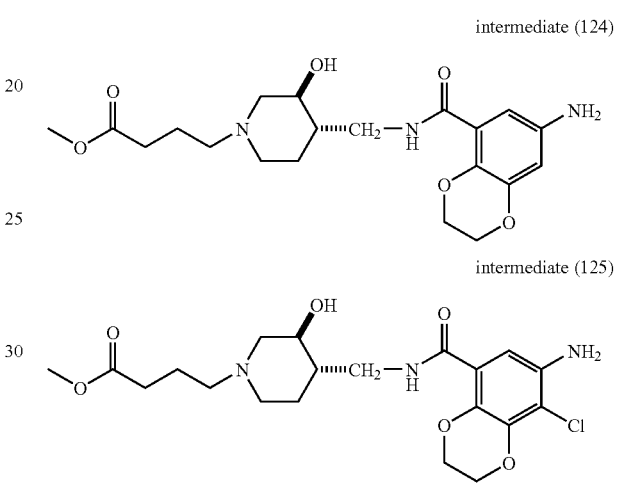

-continued intermediate (126)

intermediate (127)

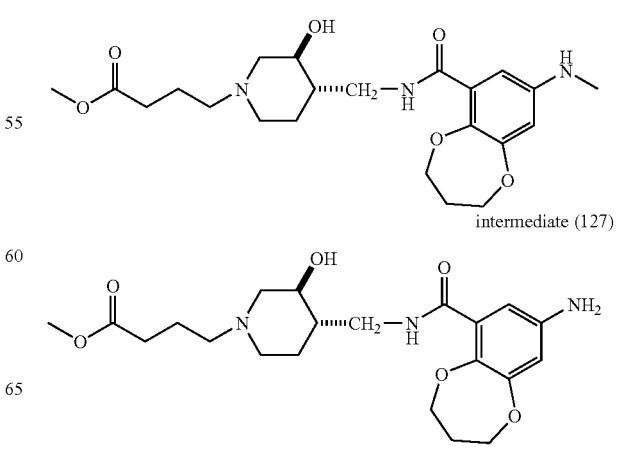

-continued intermediate (128)

intermediate (129)

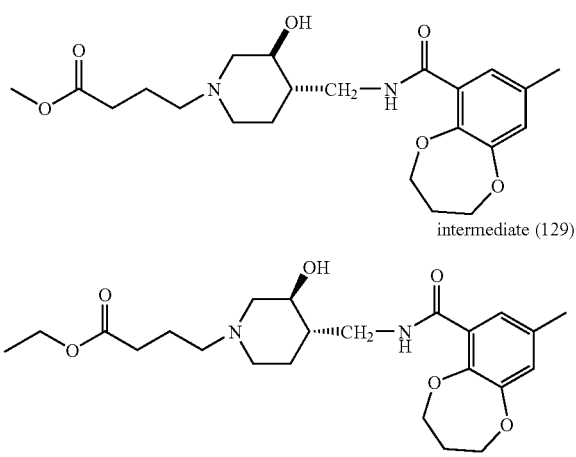

For the preparation of the final compounds, also art known intermediates have been used such as, e.g. 3-cyanopropyl bromide, tetrahydrofurfuryl methanesulfonate, 3-hydroxypropyl bromide, 2-methoxyethyl bromide, 3-methoxypropyl chloride, (trans)-4-(aminomethyl)-1-[2-(1,3-dioxolan-2-yl)ethyl]-3-piperidinol (described as intermediate 8 in WO-00/37461), 1-chloro-3-(1-methylethoxy)-propane, 2-(3-chloropropyl)-2-methyl-1,3-dioxolane, 2-(2-bromoethyl)-1,3-dioxolane, methyl 4-bromobutanoate, 2-chloro-acetonitrile, 2-(2-chloroethoxy)-ethanol, N-(2-chloroethyl)-methanesulfonamide, and N-[3-[(methylsulfonyl)oxy]propyl]-methanesulfonamide.

B. Preparation of the Final Compounds

Example B.1

A mixture of intermediate (95) (0.336 mol) in HCl/2-propanol (160 ml) and 2-propanol (1400 ml) was stirred and refluxed for 1 hour. The solvent was evaporated and the residue was taken up in a mixture of DCM and a small amount of methanol. The mixture was washed with an aqueous ammonia solution and the organic layer was separated, dried, filtered, and evaporated, yielding 71 g of compound (255).

Example B.2 a) Preparation of intermediate (20)

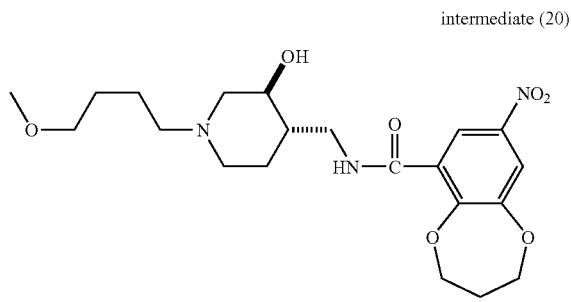

A mixture of intermediate (85) (0.01 mol), intermediate (115) (0.014 mol) and sodiumcarbonate (0.02 mol) in isobutanol (100 ml) was stirred and refluxed for 40 hours; then cooled and filtered. The filtrate's solvent was evaporated. The residue was purified by column chromatography over silica gel (eluent: $CH_2Cl_2/(CH_3OH/NH_3)$ 97/3). The desired fractions were collected and the solvent was evaporated, yielding 2.6 g of intermediate (20).

b) Intermediate (20) (0.006 mol) in methanol (100 ml) was hydrogenated with palladium-on-carbon (10%, 1 g) as a catalyst in the presence of a thiophene solution (0.5 ml). After uptake of hydrogen (3 equivalents), the catalyst was filtered off and the solvent was evaporated. The residue was purified over silica gel on a glass filter (eluent:$CH_2Cl_2/(CH_3OH/NH_3)$ 96/4). The desired fractions were collected, filtered and the solvent was evaporated. The residue was dissolved in 2-propanol and converted into the (E)-2-butenedioic acid salt (1:1) with (E)-2-butenedioic acid. The precipitate was filtered off, washed and dried, yielding 1.8 g of compound (1) (mp. 174° C.).

Example B.3 a) Preparation of intermediate (43)

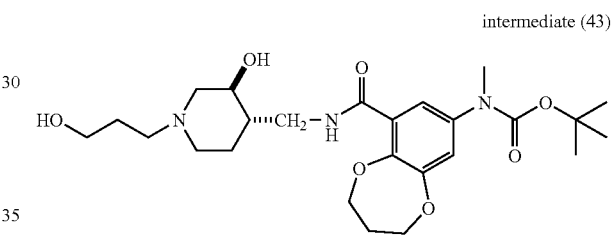

Intermediate (26) (0.012 mol) was dissolved in DCM (60 ml). Triethylamine (0.012 mol) was added and the reaction mixture was cooled to a temperature below 10° C. Formic acid (0.012 mol) was added carefully and the reaction mixture was stirred for 45 minutes at a temperature below 10° C. to give mixture (A). Intermediate (67) (0.011 mol) was stirred in DCM (60 ml). Triethylamine (0.029 mol) was added and the reaction mixture was stirred for 45 minutes at room temperature, to give mixture (B). Mixture (A) was added to mixture (B) and the resulting reaction mixture was stirred overnight at room temperature. The reaction mixture was washed with 5% NaOH, then with water. The organic layer was separated, dried, filtered and the solvent was evaporated. The residue was purified by column chromatography over silica gel (eluent:$CH_2Cl_2/CH_3OH$ 95/5). The product fractions were collected and the solvent was evaporated, yielding 3.5 g of intermediate (43).

b) A mixture of intermediate (43) (0.007 mol) in HCl/2-propanol 6N (7 ml) and 2-propanol (70 ml) was stirred and refluxed for one hour. The solvent was evaporated. The residue was partitioned between water and DCM. Sodiumcarbonate was added. The organic layer was separated, dried, filtered and the solvent was evaporated. The residue was suspended in DIPE, filtered off and dried (vacuum, 40° C.). The residue was dissolved in water and 50% NaOH. This mixture was extracted with DCM. The separated organic layer was dried, filtered and the solvent evaporated. The residue was dried (vacuum, 40° C.), then crystallized from DIPE/ACN, filtered off and dried, yielding 1.3 g of compound (2) (mp. 150° C.).

Example B.4 a) Preparation of

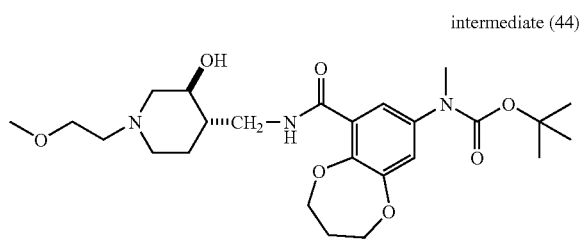

intermediate (44)

A mixture of intermediate (88) (0.0106 mol), 1-bromo-2-methoxy-ethane (0.015 mol) and sodiumcarbonate (0.02 mol) in isobutanol (100 ml) was stirred and refluxed for 20 hours, then the reaction mixture was cooled, the salts were filtered off and the filtrate was evaporated. The residue was purified by column chromatography over silica gel (eluent: $CH_2Cl_2/(CH_3OH/NH_3)$ 97/3). The product fractions were collected and the solvent was evaporated, yielding 3.3 g of intermediate (44).

b) A mixture of intermediate (44) (0.0067 mol) and HCl/2-propanol 6N (0.03 mol) in 2-propanol (80 ml) was stirred and refluxed for 1 hour, then the reaction mixture was cooled and the solvent was evaporated. The residue was taken up in DCM and washed with a 2% aqueous NaOH solution. The organic layer was separated, dried, filtered and the solvent was evaporated. The residue was suspended in DIPE, the mixture was boiled and cooled. The resulting precipitate was filtered off, washed and dried, yielding 1.78 g compound (33) (mp. 135° C.).

Example B.5

A mixture of compound (255) (0.0125 mol), 3-methoxypropyl chloride (0.025 mol) and potassiumcarbonate (0.0375 mol) in ACN (50 ml) was stirred and refluxed for 20 hours. The reaction mixture was cooled, poured out into water and extracted with DCM. The organic layer was separated, dried, filtered and the solvent was evaporated. The residue was purified by column chromatography over silica gel (eluent:$CH_2Cl_2/(CH_3OH/NH_3)$ 93/7/0.5). The pure fractions were collected and the solvent was evaporated. The precipitate was filtered off and recrystallized from a mixture of 2-propanone and DIPE, yielding 3 g of compound (200) (mp. 108° C.; $[\alpha]^{20,D}=-10.70°$, (c=10.28 mg/2 ml in methanol)).

Example B.6

A mixture of compound (8) (0.0094 mol), butanal (0.0094 mol) and potassium acetate (0.015 mol) in methanol (100 ml) was hydrogenated with platinum-on-carbon (5%, 1 g) as a catalyst in the presence of a thiophene solution (2 ml). After uptake of hydrogen (1 equivalent), the catalyst was filtered off over celite and the filtrate was evaporated. The residue was partitioned between a 2% aqueous NaOH solution (100 ml) and DCM (150 ml). The layers were separated. The aqueous phase was re-extracted with DCM (100 ml). The combined organic layers were dried, filtered and the solvent was evaporated. The residue was purified by column chromatography over silica gel (eluent:$CH_2Cl_2/(CH_3OH/NH_3)$ 97/3). The product fractions were collected and the solvent was evaporated. The residue was dissolved in ACN and converted into the ethanedioic acid salt (1:2), then filtered off and dried, yielding 1.62 g of compound (11) (mp. >110° C.). An analogous procedure can by used by replacing butyraldehyde with 4-fluoro-benzaldehyde for preparing compounds such as, e.g. compound (64).

Example B.7

Intermediate (123) (0.004 mol) in water (100 ml) was stirred and refluxed for 6 hours. The reaction mixture was cooled and washed with DCM. The solvent was evaporated. The residue was suspended in ACN. The precipitate was filtered off, washed and dried, yielding 1.58 g of compound (16) (mp. 240° C.).

Example B.8

Triethylamine (1.4 ml) was added to a suspension of intermediate (12) (0.01 mol) in DCM (75 ml) and the reaction mixture was cooled to a temperature below 0° C. Formic acid (0.96 ml) was added dropwise at a temperature below 0° C. and the reaction mixture was stirred for 30 minutes at a temperature below 0° C. A suspension of intermediate (69) (0.01 mol) in DCM (25 ml) and triethylamine (2.4 ml) was added, then the mixture was stirred at room temperature for 3 hours. DCM (100 ml) and water (150 ml) were added, the mixture was stirred and the layers were separated. The organic layer was washed with a 5% aqueous NaOH solution and with water, then dried, filtered and the solvent was evaporated. The residue was purified by column chromatography over silica gel (eluent: $CH_2Cl_2/(CH_3OH/NH_3)$ 96/4). The product fractions were collected and the solvent was evaporated. The residue was crystallised from DIPE with a small amount of ACN, the resulting precipitate was filtered off and dried, yielding 2.2 g of compound (26) (mp. 106-108° C.).

Example B.9

A mixture of compound (43) (0.0051 mol) in a 5% aqueous HCl solution (50 ml) and THF (50 ml) was stirred overnight at room temperature; then concentrated in vacuo. The concentrate was basified with an aqueous ammonia solution and extracted with DCM (3×). The separated organic layer was dried, filtered and the solvent was evaporated. The residue was crystallized from DIPE/ACN. The precipitate was filtered off and dried, yielding 1.9 g of compound (44) (mp. 130° C.).

Example B.10 a) Preparation of

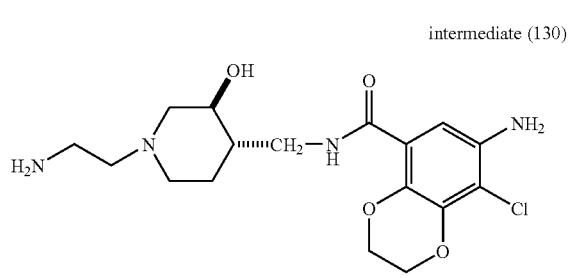

intermediate (130)

Compound (24) (0.026 mol) in CH$_3$OH/NH$_3$ (250 ml) was hydrogenated with Raney Nickel as a catalyst in the presence of thiophene solution (1 ml). After uptake of hydrogen (2 equivalents), the catalyst was filtered off and the solvent was evaporated. The residue was crystallized from ACN (0° C.). The precipitate was filtered off and dried, yielding 8 g of intermediate (130). b) Intermediate (130) (0.008 mol) was taken up in chloroform (100 ml). Triethylamine (0.012 mol) was added. Methanesulfonyl chloride (0.008 mol) in chloroform (10 ml) was added dropwise at a temperature below 5° C. The reaction mixture was stirred for 30 minutes, washed with water, dried, filtered and the solvent was evaporated. The residue was purified by column chromatography over silica gel (eluent: CH$_2$Cl$_2$/(CH$_3$OH/NH$_3$) 93/7). The desired fractions were collected and the solvent was evaporated. The residue was suspended in DIPE/ACN (0° C.). The precipitate was filtered off and dried, yielding 1.1 g of compound (63) (mp. 180° C.).

Example B.11

A mixture of intermediate (130) (0.016 mol), 2-chloro-3-methyl-pyrazine (0.016 mol) and calcium oxide (0.02 mol) in DMA (5 ml) was stirred at 120° C. for 48 hours; then cooled. Water was added and the mixture was extracted with CH$_2$Cl$_2$/CH$_3$OH. The separated organic layer was dried, filtered and the solvent was evaporated. The residue was purified by column chromatography over silica gel (eluent: CH$_2$Cl$_2$/(CH$_3$OH/NH$_3$) 93/7). The desired fractions were collected and the solvent was evaporated. The residue was suspended in DIPE (0° C.). The precipitate was filtered off and dried, yielding 1.45 g of compound (68) (mp. 100° C.).

Example B.12 a) Preparation of

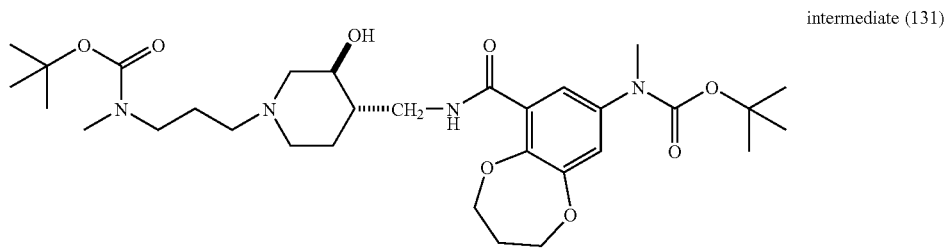

intermediate (131)

A mixture of intermediate (88) (0.01 mol) and 1,1-dimethyl-methyl-(3-oxopropyl)-carbamic acid ester (±0.015 mol) in THF (100 ml) was hydrogenated with palladium-on-carbon (10%, 2 g) as a catalyst in the presence of thiophene solution (2 ml). After uptake of hydrogen (1 equivalent), the catalyst was filtered off and the filtrate was evaporated. The residue was purified by short column chromatography over silica gel. The product fractions were collected and the solvent was evaporated, yielding 2.9 g of intermediate (131).

b) A mixture of intermediate (131) (0.0048 mol) and HCl/2-propanol (6N) (5 ml) in 2-propanol (100 ml) was stirred and refluxed for 1 hour, then the reaction mixture was cooled and the solvent was evaporated. The residue was taken up in DCM and washed with a 2% aqueous NaOH solution. The organic layer was separated, dried, filtered and the solvent was evaporated. The residue was purified by column chromatography on silica gel (eluent: CH$_2$Cl$_2$/(CH$_3$OH/NH$_3$) 90/10). The product fractions were collected and the solvent was evaporated. The residue was dissolved in 2-propanol and converted into the (E)-2-butenedioic acid salt (2:3) with fumaric acid (2 equivalents). The precipitate was filtered off, and dried, yielding 1.13 g of compound (81) (mp. >130° C.).

Example B.13 a) Preparation of

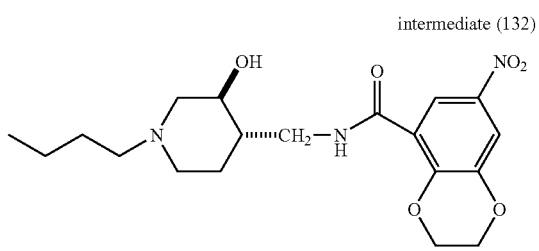

intermediate (132)

A mixture of intermediate (3) (0.013 mol) in DCM (60 ml) was stirred and cooled in an ice-bath. Triethylamine (0.013 mol) was added carefully and the mixture was stirred at a temperature of 10° C., then formic acid (0.013 mol) was added dropwise and the mixture was stirred for 45 minutes. A solution of intermediate (73) (0.012 mol) in DCM (30 ml) was added and the reaction mixture was stirred overnight at room temperature. The reaction mixture was washed with a 5% aqueous NaOH-solution and water. The separated aqueous layer was extracted with DCM. The separated organic layer was dried, filtered and concentrated. The residue was purified by column chromatography over silica gel (eluent: CH$_2$Cl$_2$/CH$_3$OH 90/10). The pure fractions were collected and the solvent was evaporated. The residue was concentrated with toluene and the solvent was evaporated, yielding 2.75 g of intermediate (132).

b) A mixture of intermediate (132) (0.0069 mol) in methanol (150 ml) was hydrogenated with palladium-on-carbon (10%, 1 g) as a catalyst in the presence of thiophene solution (1 ml). After uptake of hydrogen (3 equivalents), the catalyst was filtered off over dicalite and the filtrate was concentrated. The residue was crystallized from 2-propanol and DIPE and converted into the ethanedioic acid salt (2:3). The residue was filtered and dried, yielding 2.25 g of compound (107) (mp. > 160° C.).

Example B.14 a) Preparation of

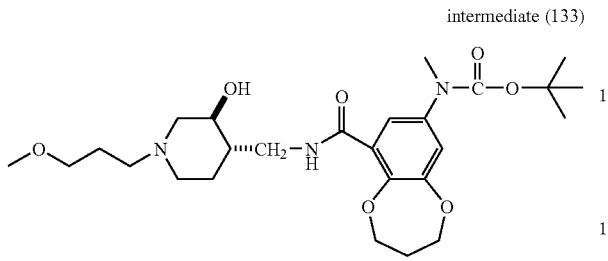

intermediate (133)

A mixture of intermediate (26) (0.016 mol) in DCM (60 ml) was stirred, triethylamine (0.016 mol) was added and the reaction mixture was cooled on an icebath (temperature below 10° C.). Then formic acid (0.016 mol) was added dropwise and the reaction mixture was stirred at a temperature below 10° C. for 45 minutes. (Solution A). A solution of intermediate (69) (0.013 mol) in DCM (60 ml) was stirred at room temperature, triethylamine (0.03 mol) was added and the reaction mixture was stirred at room temperature for 45 minutes. The first solution (A) was added and the reaction mixture was stirred overnight at room temperature. The reaction mixture was washed with water. The separated organic layer was dried, filtered and concentrated. The residue was purified by column chromatography over silica gel (eluent: $CH_2Cl_2/(CH_3OH/NH_3\ 7N)95/5$). The product fractions were collected and the solvent was evaporated, yielding 3.1 g of intermediate (133).

b) A mixture of intermediate (133) (0.006 mol) in 2-propanol/HCl (6N) (6 ml) and 2-propanol (60 ml) was stirred and refluxed for 1 hour. The reaction mixture stood overnight at room temperature and was then concentrated. The residue was partitioned between an aqueous ammonia-solution and DCM. The separated organic layer was dried, filtered and concentrated. The product was crystallized from ACN and DIPE, filtered and dried, yielding 1.55 g of compound (113) (mp. 126° C.).

Example B.15 a) Preparation of

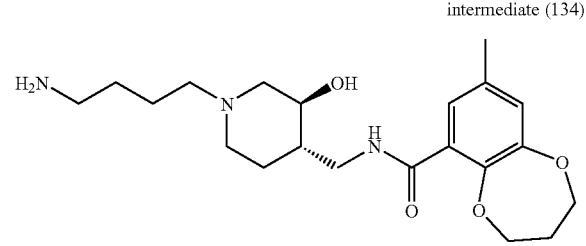

intermediate (134)

Compound (226) (0.013 mol) in $CH_3OH/NH_3$ (300 ml) was hydrogenated with Raney Nickel (1 g) as a catalyst. After uptake of hydrogen (2 equivalents) the catalyst was filtered off and the filtrate was evaporated, yielding 5.1 g of intermediate (134).

b) Methanesufonyl chloride (0.54 ml) was added dropwise at room temperature to a mixture of intermediate (134) (0.0064 mol) and triethylamine (0.013 mol) in DCM (60 ml). After 3 hours, methanesufonyl chloride (0.2 ml) was added and the mixture was stirred for 24 hours. The mixture was washed with water, the organic layer was dried, filtered and the solvent was evaporated. The residue was purified by flash column chromatography over silica gel (eluent: $CH_2Cl_2/(CH_3OH/NH_3)$ 99/1, 98/2, 97/3). The product fractions were collected and the solvent was evaporated. The residue was crystallised from DIPE with a small amount of ACN, filtered off, washed and dried, yielding 0.7 g of compound (193) (mp. 134° C.; $[\alpha]^{20,D}=-9.83°$ (c=23.40 mg/5 ml in $CH_3OH$)).

Example B.16

A mixture of compound (192) (0.006 mol) in pyridine (0.012 mol), DCM (50 ml) and THF (50 ml) was stirred (5° C.) under Argon. Thionyl chloride (0.006 mol) was added dropwise (5° C.). The reaction mixture was stirred at 5° C. for 1 hour, ammonia (gaseous) was bubbled through at 5° C. for 10 min. After reaching room temperature, the mixture was stirred for 2 hours, taken up in DCM and washed with water. The organic layer was dried, filtered and the solvent was evaporated. The residue was purified over silica gel on a glass filter (eluent: $CH_2Cl_2/(CH_3OH/NH_3)$ 93/7). The product fractions were collected and the solvent was evaporated. The residue was crystallised from DIPE, filtered off, washed and dried, yielding 0.4 g of compound (197) (m.p. 136° C.; $[\alpha]^{20,D}=-11.52°$ (c=10.42 mg/5 ml in $CH_3OH$)).

Example B.17

A mixture of compound (192) (0.005 mol) and triethylamine (0.01 mol) in DCM (30 ml) was stirred at 5° C. Formic acid (0.005 mol) was added dropwise at 5° C. The mixture was stirred at 5° C. for 30 minutes. Then, 1-methyl-piperazine (0.015 mol) was added at 5° C. The reaction mixture was allowed to reach room temperature and was washed with water. The organic layer was dried, filtered and the solvent was evaporated. The residue was purified by column chromatography over silica gel (eluent:$CH_2Cl_2/(CH_3OH/NH_3)$ 95/5). The product fractions were collected and the solvent was evaporated. The residue was dissolved in ethyl acetate and converted into the ethanedioic acid salt (1:1). The precipitate was filtered off and dried, yielding 0.6 g of compound (238) (mp. >112° C.).

Example B.18

A mixture of compound (241) (0.0033 mol), potassium hydroxide (0.009 mol) and ethanol (50 ml) was stirred and refluxed for 5 days. The mixture was cooled and the solvent was evaporated. The residue was partitioned between water and DCM and was extracted 2 times with DCM. The organic layer was seperated, dried, filtered and the solvent was evaporated. The residue was purified by column chromatography over silica gel (eluent: $CH_2Cl_2/(CH_3OH/NH_3)$ 95/5). The product fractions were collected and the solvent was evaporated. The residue was dried, yielding 0.14 g of compound (249).

Table F-1 lists the compounds that were prepared according to one of the above Examples.

TABLE F-1

| Co. No. | Ex. No. | Structure | Physical data |
|---|---|---|---|
| 1 | B.2 | 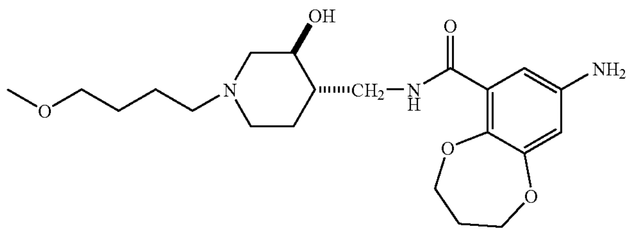 | (trans); (E)-2-butenedioate (1:1); mp. 174° C. |
| 2 | B.3 | 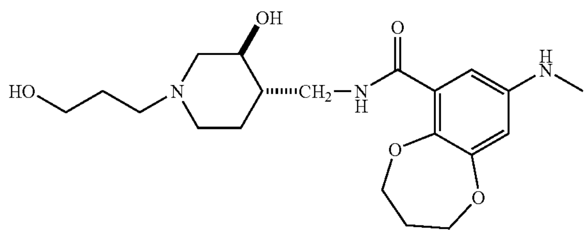 | (trans); mp. 150° C. |
| 3 | B.2 | 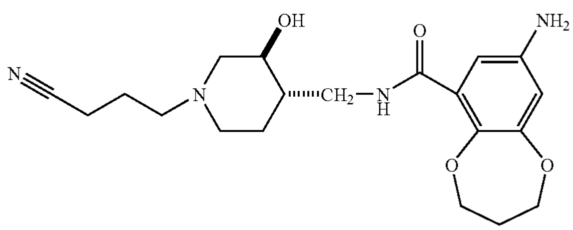 | (trans); mp. 127° C. |
| 4 | B.2 | 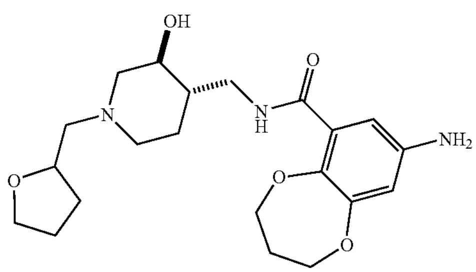 | (trans); mp. 90.2-112.3° C. |
| 5 | B.1 | 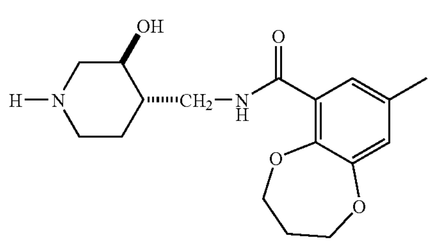 | (trans); ethanedioate (1:1); mp. 213° C. |
| 6 | B.2 | 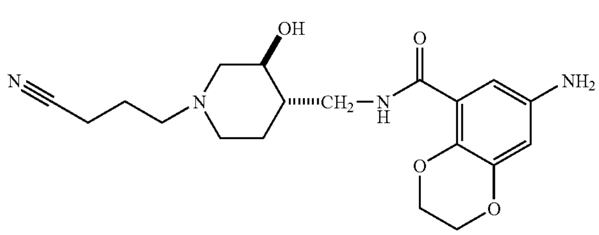 | (trans); mp. 142° C. |

TABLE F-1-continued

| Co. No. | Ex. No. | Structure | Physical data |
|---|---|---|---|
| 7 | B.5 | 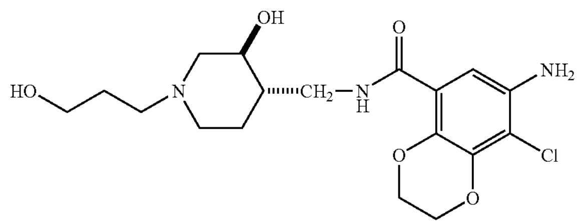 | (trans); ethanedioate (1:2); mp. >125° C. |
| 8 | B.1 | 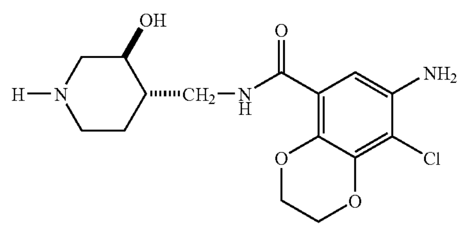 | (trans); HCl (1:2); mp. >180° C. |
| 9 | B.5 | 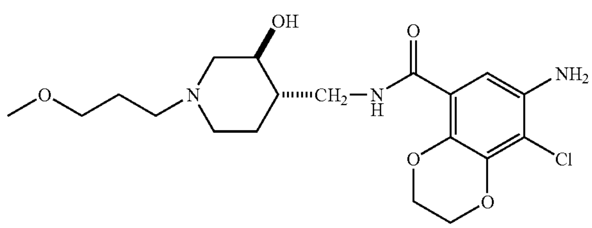 | (trans); ethanedioate (1:1) 2-propanolate (1:1); mp. >92° C. |
| 10 | B.5 | 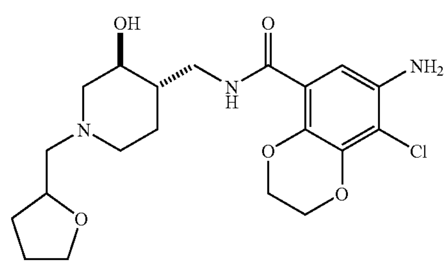 | (trans); ethanedioate (1:2); mp. >130° C. |
| 11 | B.6 | 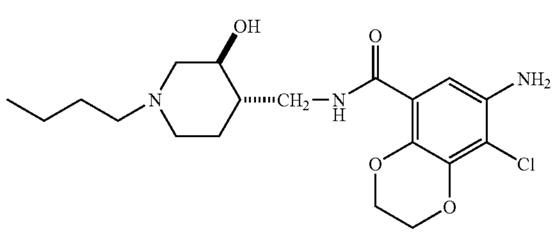 | (trans); ethanedioate (1:2); mp. >110° C. |

TABLE F-1-continued

| Co. No. | Ex. No. | Structure | Physical data |
|---|---|---|---|
| 12 | B.3 | 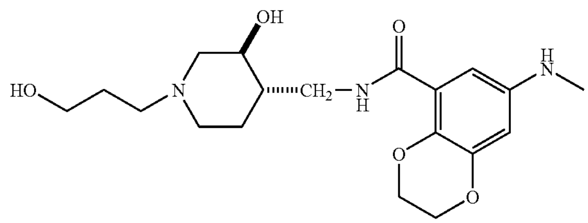 | (trans); mp. 146° C. |
| 13 | B.3 | 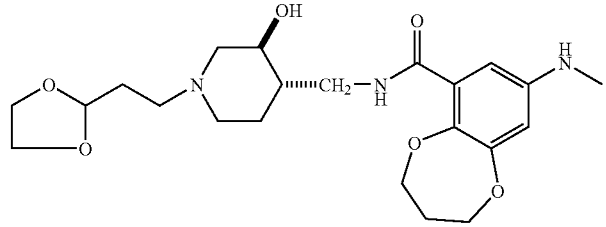 | (trans); mp. 140° C. |
| 14 | B.5 | 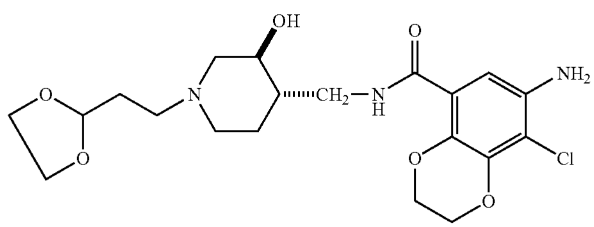 | (trans); mp. 168-170° C. |
| 15 | B.5 | 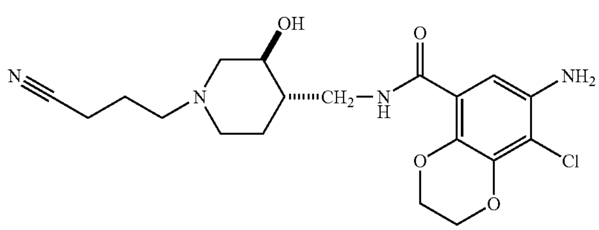 | (trans); ethanedioate (1:2); mp.>115° C. |
| 16 | B.7 | 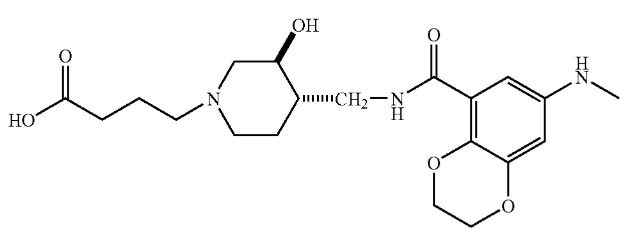 | (trans); mp. 240° C. |

TABLE F-1-continued

| Co. No. | Ex. No. | Structure | Physical data |
|---|---|---|---|
| 17 | B.3 | 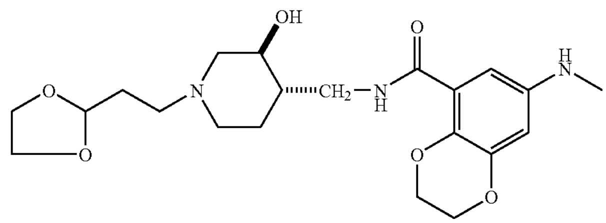 | (trans); mp. 128° C. |
| 18 | B.7 | 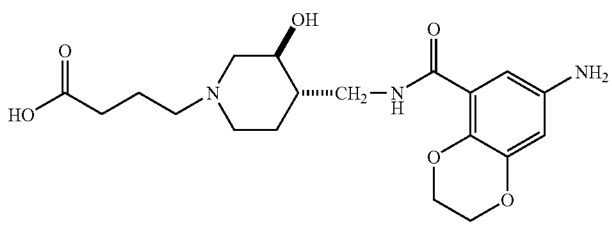 | (trans); mp. 140° C. |
| 19 | B.3 | 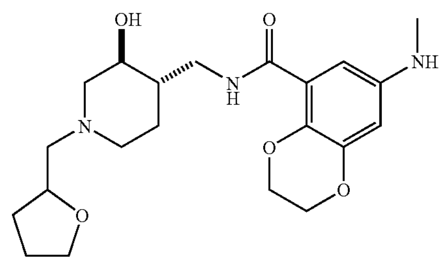 | (trans); HCl (1:1); mp. 197° C. |
| 20 | B.3 | 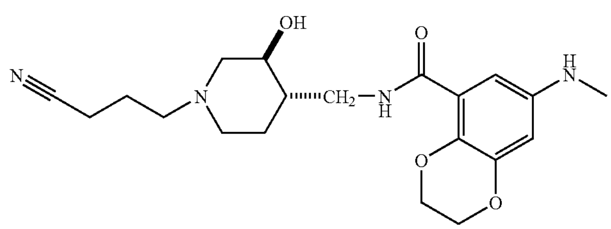 | (trans); (E)-2-butenedioate (2:1); mp. 184° C. |
| 21 | B.3 | 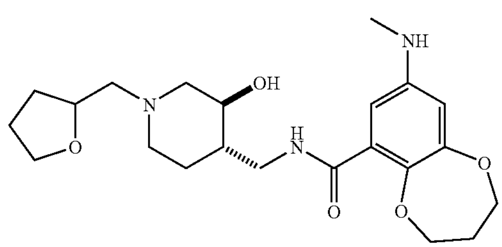 | (trans); mp. 153° C. |

TABLE F-1-continued

| Co. No. | Ex. No. | Structure | Physical data |
|---|---|---|---|
| 22 | B.2 | 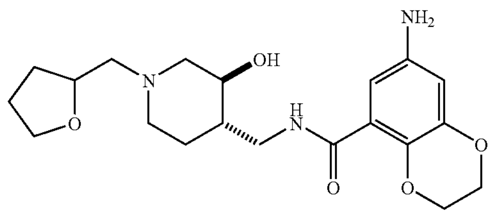 | (trans); ethanedioate (1:2); mp. >174° C. |
| 23 | B.2 | 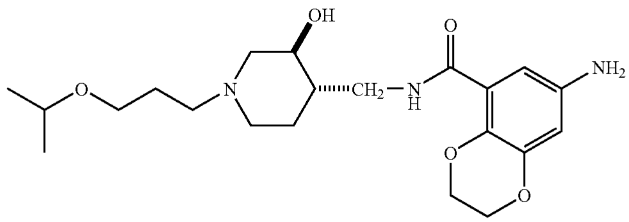 | (trans); ethanedioate (1:2); mp. >162° C. |
| 24 | B.5 | 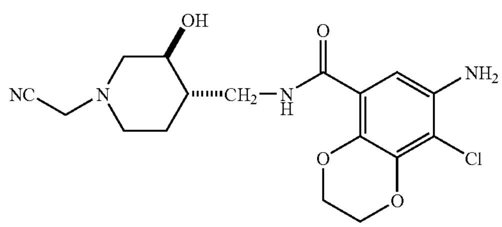 | (trans); |
| 25 | B.7 | 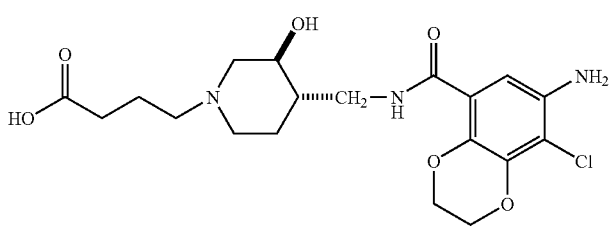 | (trans); H$_2$O (1:1); mp. >125° C. |
| 26 | B.8 | 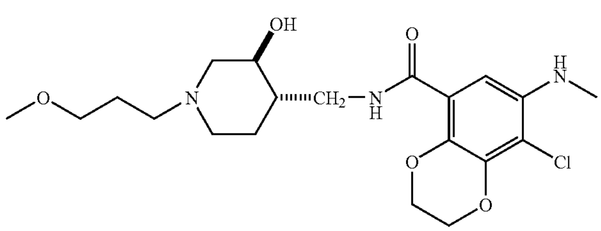 | (trans); mp. 104.7-107.6° C. |

TABLE F-1-continued

| Co. No. | Ex. No. | Structure | Physical data |
|---|---|---|---|
| 27 | B.7 | 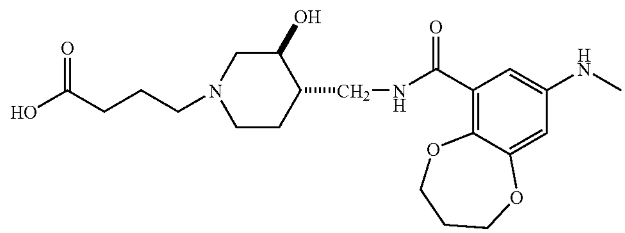 | (trans); mp. >180° C. |
| 28 | B.8 | 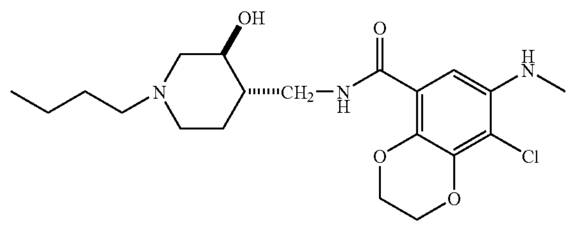 | (trans); ethanedioate (1:2); mp. >125° C. |
| 29 | B.5 | 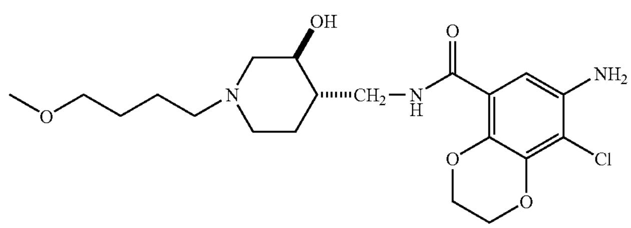 | (trans); mp. 96° C. |
| 30 | B.8 | 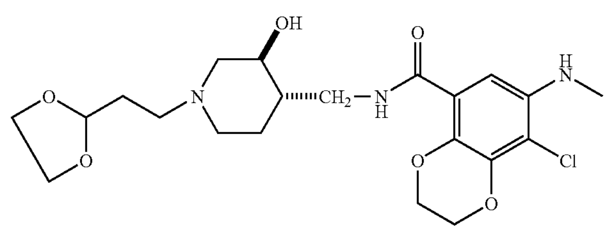 | (trans); mp. 139° C. |
| 31 | B.5 | 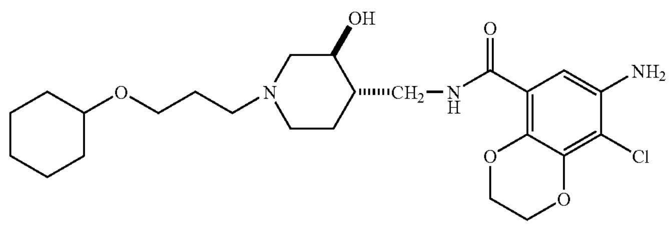 | (trans); mp. 118° C. |

TABLE F-1-continued

| Co. No. | Ex. No. | Structure | Physical data |
|---|---|---|---|
| 32 | B.2 | 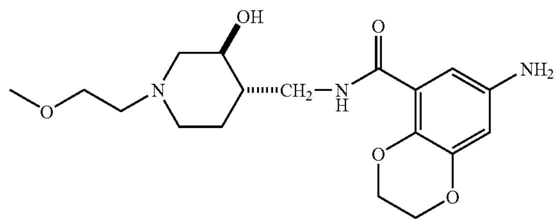 | (trans); ethanedioate (1:2); mp. 162° C. |
| 33 | B.4 | 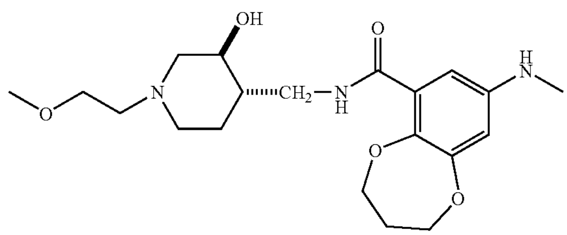 | (trans); mp. 135° C. |
| 34 | B.4 | 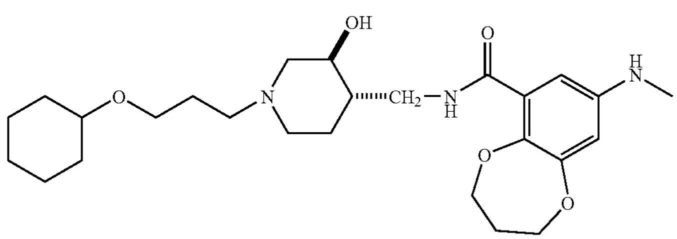 | (trans); mp. 128° C. |
| 35 | B.4 | 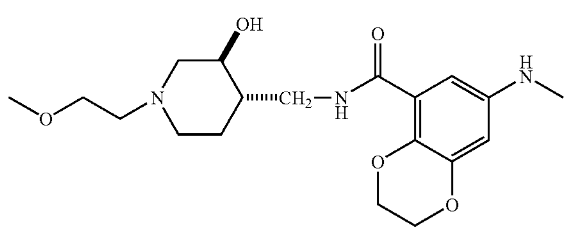 | (trans); mp. 122° C. |
| 36 | B.4 | 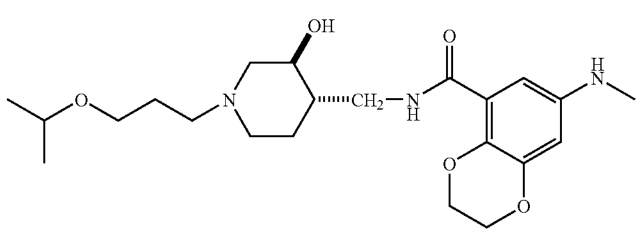 | (trans); HCl (1:2) H$_2$O (1:1); mp. 150° C. |

TABLE F-1-continued

| Co. No. | Ex. No. | Structure | Physical data |
|---|---|---|---|
| 37 | B.2 | 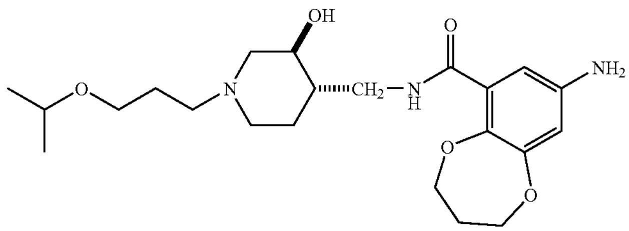 | (trans); mp. 113° C. |
| 38 | B.4 | 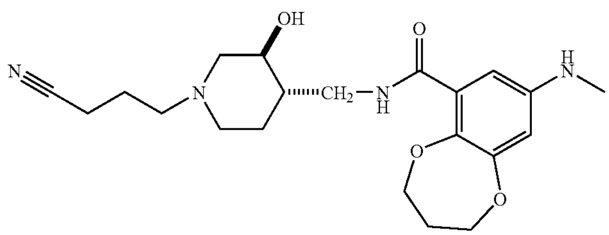 | (trans); HCl (1:2); mp. 135° C. |
| 39 | B.7 | 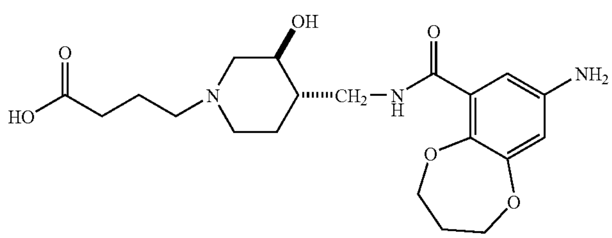 | (trans); 2-propanolate (1:1); mp. 110° C. |
| 40 | B.4 | 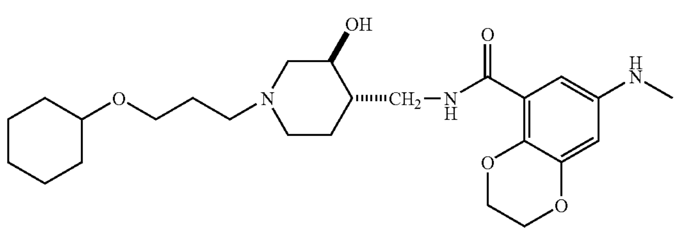 | (trans); ethanedioate (1:2); mp. 152° C. |
| 41 | B.2 | 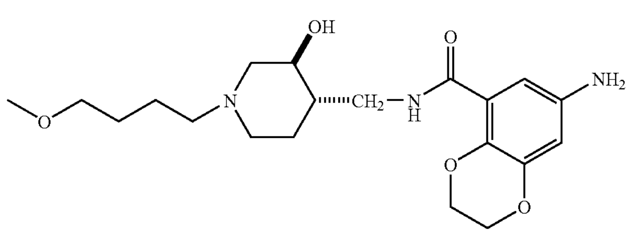 | (trans); ethanedioate (1:2); mp. 150° C. |

TABLE F-1-continued

| Co. No. | Ex. No. | Structure | Physical data |
|---|---|---|---|
| 42 | B.5 | 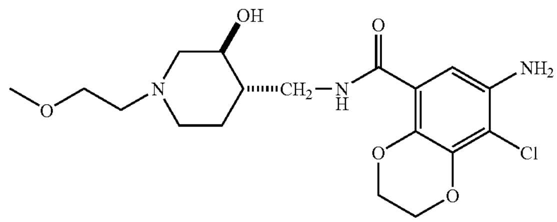 | (trans); HCl (1:2); mp. 180° C. |
| 43 | B.5 | 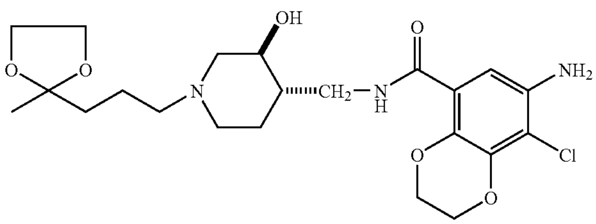 | (trans); mp. 144° C. |
| 44 | B.9 | 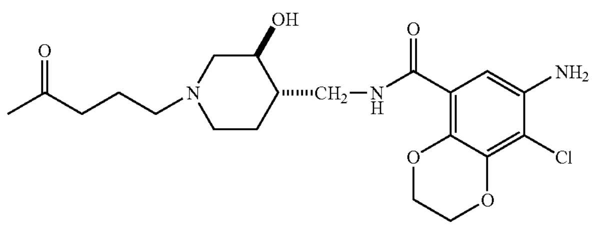 | (trans); mp. 130° C. |
| 45 | B.2 | 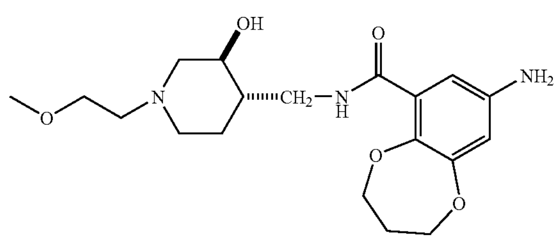 | (trans); (E)-2-butenedioate (2:1); mp. 232° C. |
| 46 | B.6 | 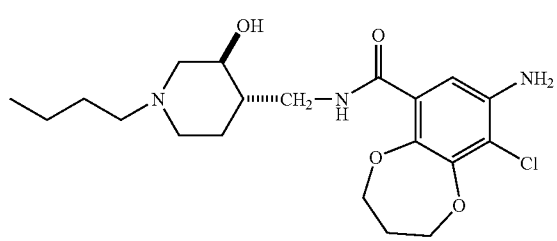 | (trans); mp. 158° C. |

TABLE F-1-continued

| Co. No. | Ex. No. | Structure | Physical data |
|---|---|---|---|
| 47 | B.5 | 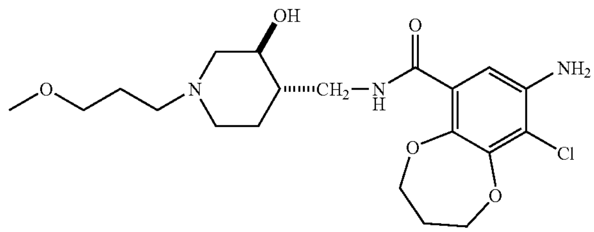 | (trans); mp. 150° C. |
| 48 | B.5 | 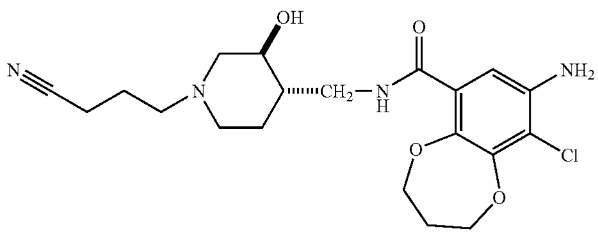 | (trans); mp. 143° C. |
| 49 | B.2 | 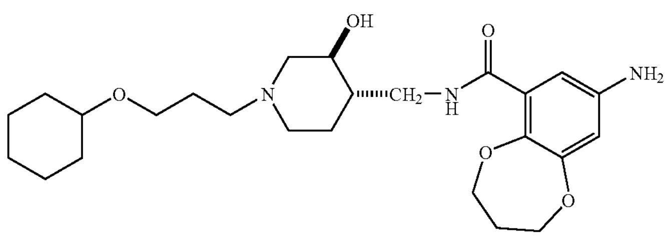 | (trans); (E)-2-butenedioate (1:1); mp. 191° C. |
| 50 | B.5 | 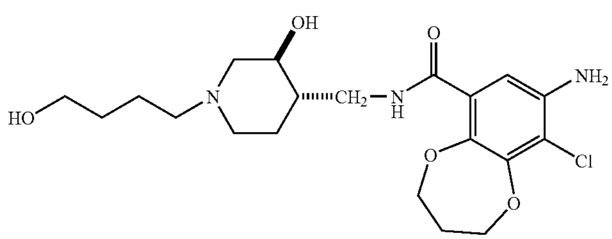 | (trans); mp. 172° C. |
| 51 | B.5 | 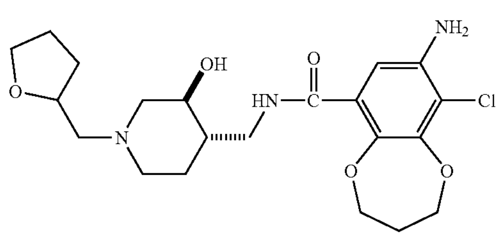 | (trans); mp. 118° C. |

TABLE F-1-continued

| Co. No. | Ex. No. | Structure | Physical data |
|---|---|---|---|
| 52 | B.5 | 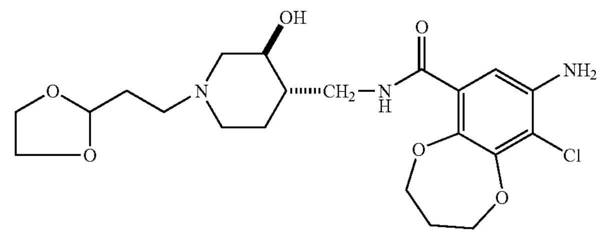 | (trans); mp. 160° C. |
| 53 | B.5 | 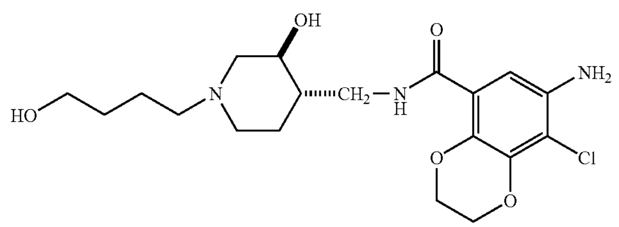 | (trans); mp. 162° C. |
| 54 | B.4 | 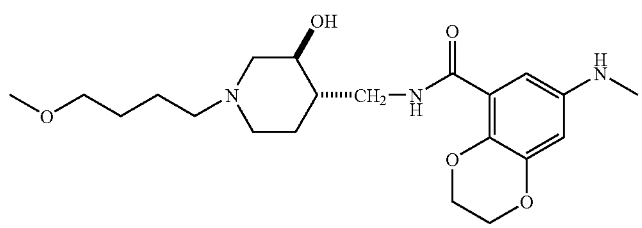 | (trans); (E)-2-butenedioate (2:1); mp. 200° C. |
| 55 | B.6 | 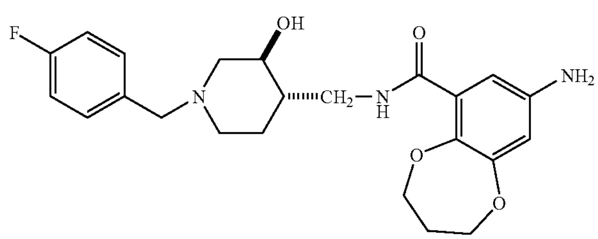 | (trans); (E)-2-butenedioate (1:1); mp. 216° C. |
| 56 | B.4 | 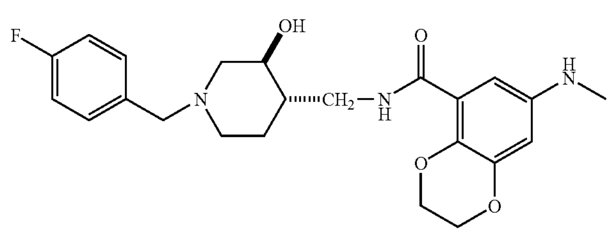 | (trans); mp. 185° C. |

TABLE F-1-continued
| Co. No. | Ex. No. | Structure | Physical data |
|---|---|---|---|
| 57 | B.2 | 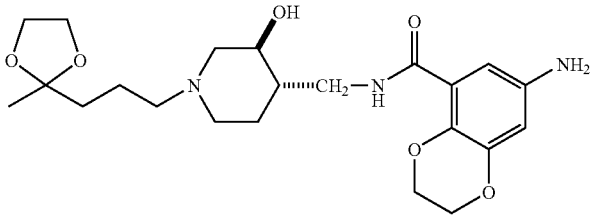 | (trans) |
| 58 | B.5 | 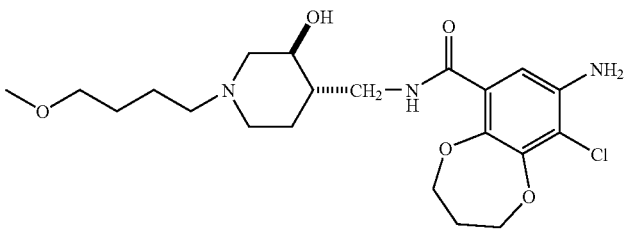 | (trans); mp. 128° C. |
| 59 | B.2 | 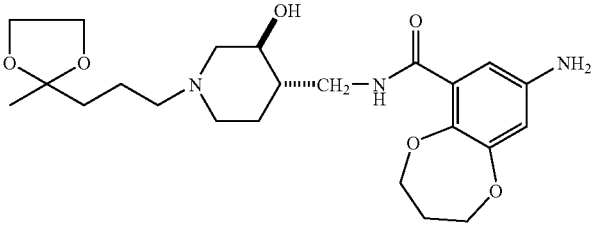 | (trans); (E)-2-butenedioate (1:1); mp. 197° C. |
| 60 | B.9 | 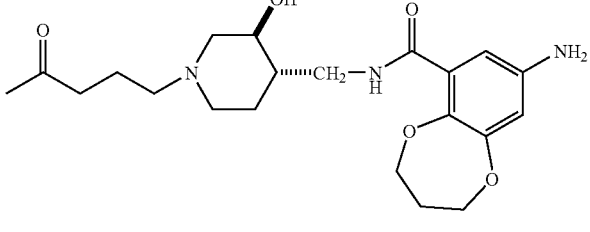 | (trans); (E)-2-butenedioate (1:1); mp. 160° C. |
| 61 | B.9 | 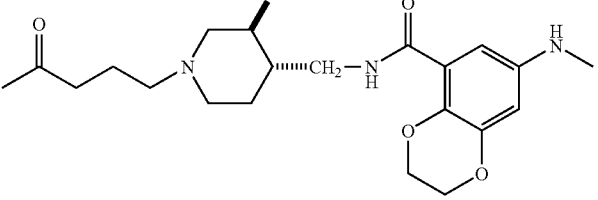 | (trans); mp. 138° C. |

TABLE F-1-continued

| Co. No. | Ex. No. | Structure | Physical data |
|---|---|---|---|
| 62 | B.4 | 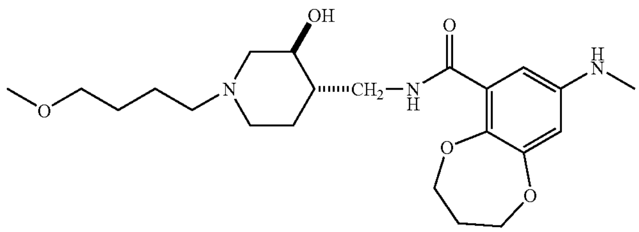 | (trans); mp. 114° C. |
| 63 | B.10 | 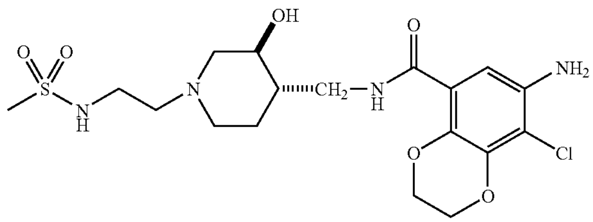 | (trans); mp. 180° C. |
| 64 | B.6 | 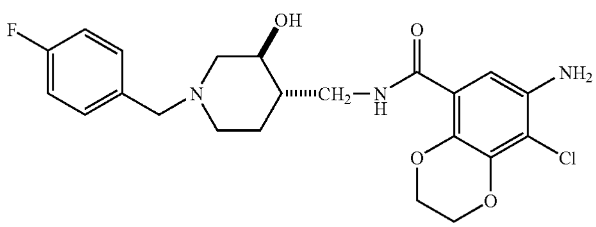 | (trans); mp. 170° C. |
| 65 | B.5 | 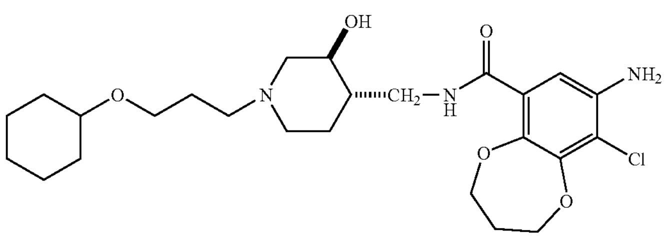 | (trans); mp. 133° C. |
| 66 | B.7 | 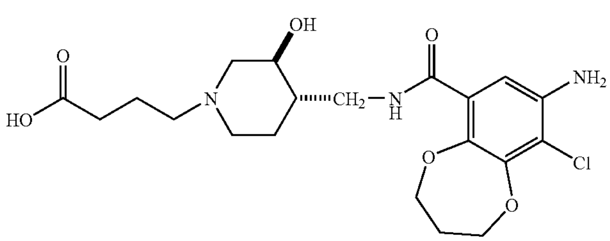 | (trans); mp. 220° C. |

TABLE F-1-continued
| Co. No. | Ex. No. | Structure | Physical data |
|---|---|---|---|
| 67 | B.4 | 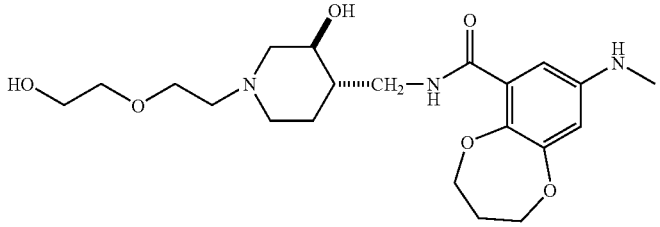 | (trans); HCl (1:2); mp. 182° C. |
| 68 | B.11 | 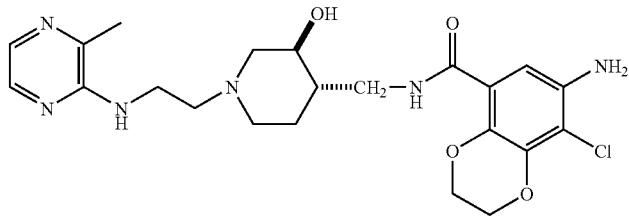 | (trans); mp. 100° C. |
| 69 | B.2 | 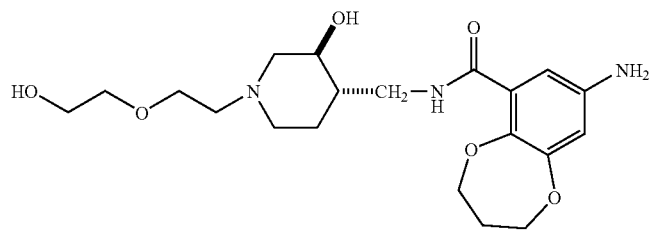 | (trans); (E)-2-butenedioate (2:1); mp. 191° C. |
| 70 | B.5 | 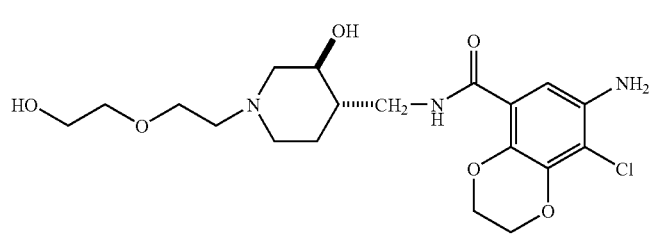 | (trans); mp. 140° C. |
| 71 | B.5 | 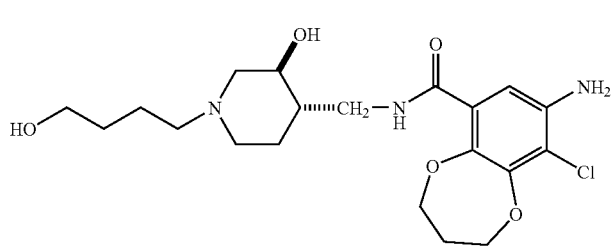 | (trans); mp. 145° C. |

TABLE F-1-continued

| Co. No. | Ex. No. | Structure | Physical data |
|---|---|---|---|
| 72 | B.5 | 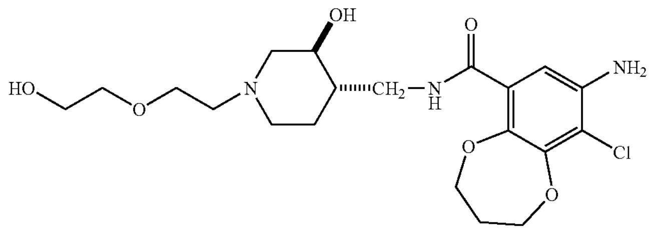 | (trans); mp. 140° C. |
| 73 | B.2 | 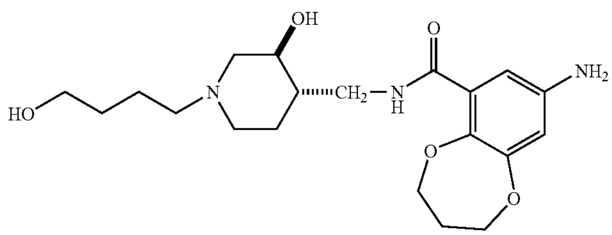 | (trans); (E)-2-butenedioate (2:1); mp. 225° C. |
| 74 | B.4 | 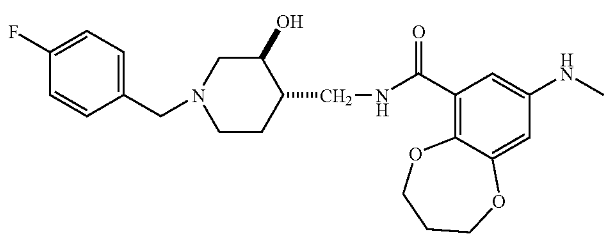 | (trans); mp. 145° C. |
| 75 | B.5 | 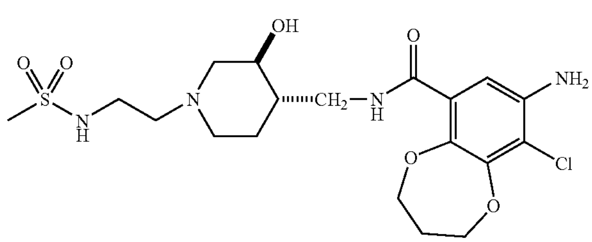 | (trans); mp. 188° C. |
| 76 | B.5 | 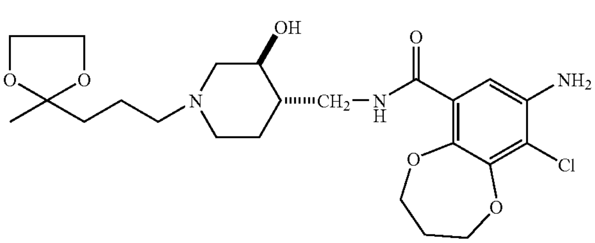 | (trans); mp. 133° C. |

TABLE F-1-continued

| Co. No. | Ex. No. | Structure | Physical data |
|---|---|---|---|
| 77 | B.4 | 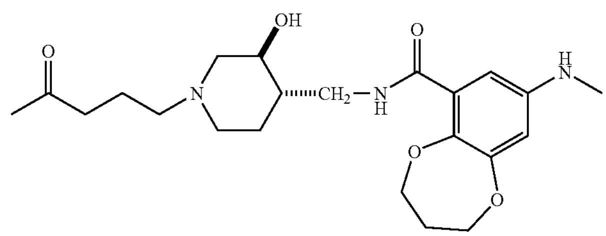 | (trans); (E)-2-butenedioate (2:1); mp. 176° C. |
| 78 | B.6 | 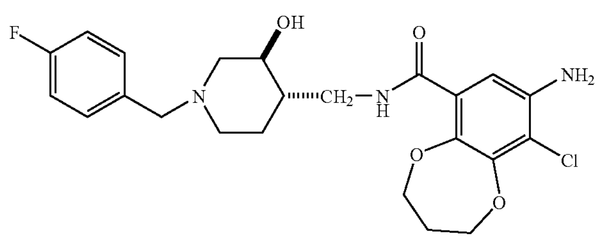 | (trans); mp. 172° C. |
| 79 | B.5 | 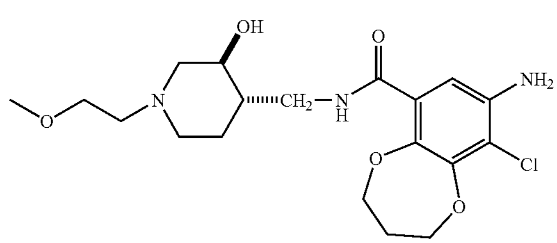 | (trans); mp. 137° C. |
| 80 | B.9 | 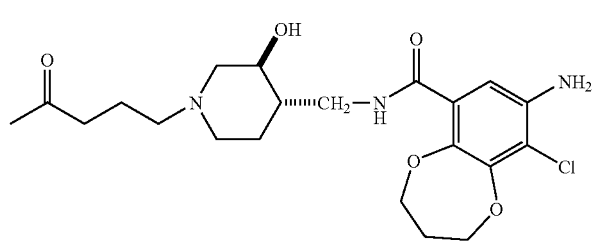 | (trans); mp. 153° C. |
| 81 | B.12 | 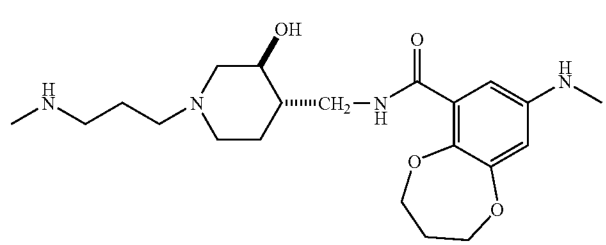 | (trans); (E)-2-butenedioate (1:2) H₂O (1:1); mp. >130° C. |

TABLE F-1-continued

| Co. No. | Ex. No. | Structure | Physical data |
|---|---|---|---|
| 82 | B.5 | 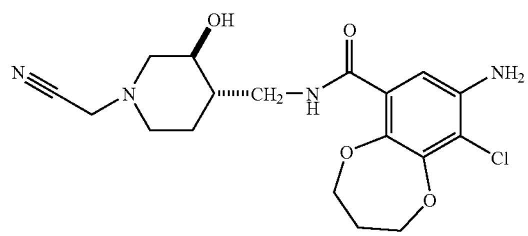 | (trans); mp. 159° C. |
| 83 | B.9 | 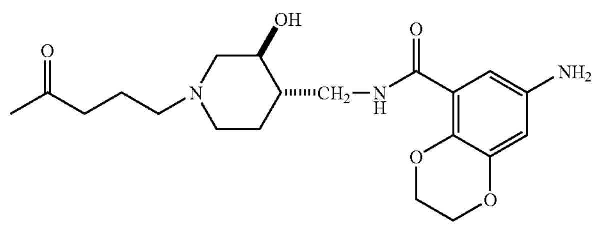 | (trans); mp. 143° C. |
| 84 | B.4 | 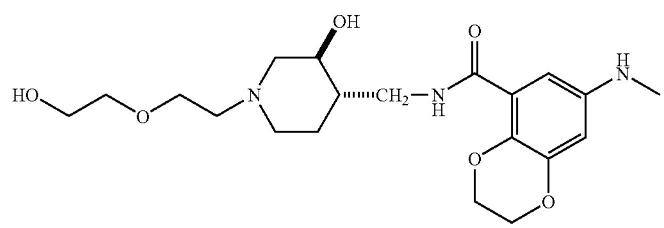 | (trans); HCl (1:2) H₂O (1:1); mp. >165° C. |
| 85 | B.2 | 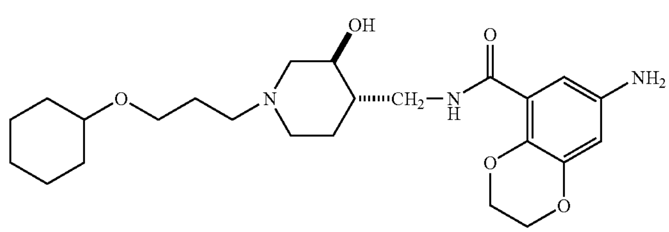 | (trans); ethanedioate (2:3) H₂O (1:1); mp. 168° C. |
| 86 | B.2 | 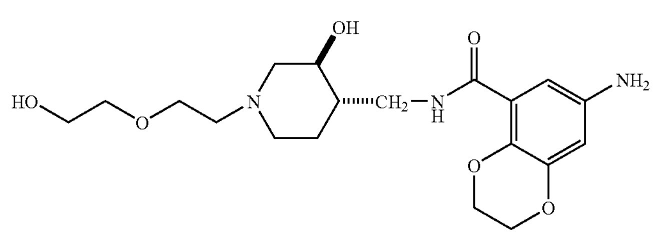 | (trans); ethanedioate (2:3) H₂O (1:1) 2-propanolate (2:1); mp. >70° C. |

TABLE F-1-continued

| Co. No. | Ex. No. | Structure | Physical data |
|---|---|---|---|
| 87 | B.5 | 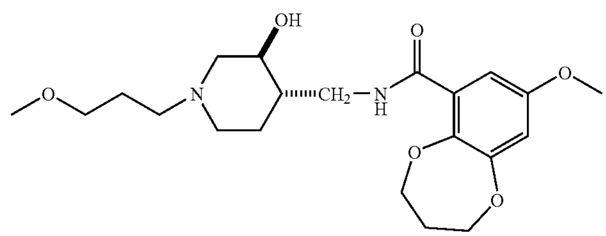 | (trans); mp. 110° C. |
| 88 | B.1 | 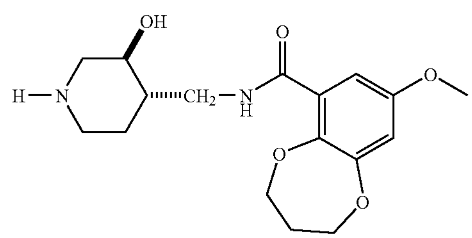 | (trans); ethanedioate (1:1); mp. 188° C. |
| 89 | B.12 | 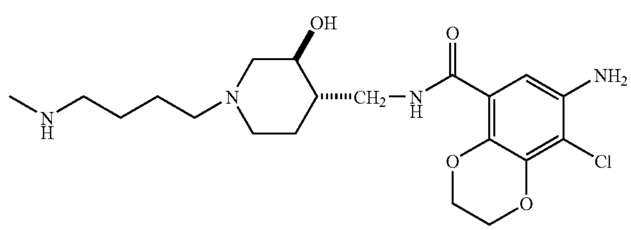 | (trans); HCl (1:2); mp. 220° C. |
| 90 | B.12 | 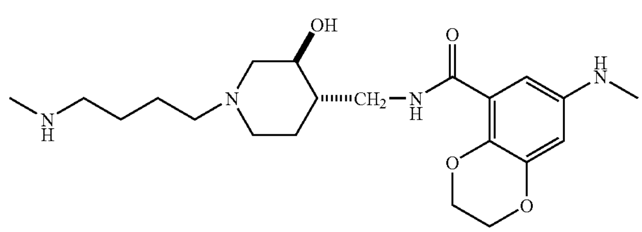 | (trans); (E)-2-butenedioate (2:3) H₂O (1:2); mp. 173° C. |
| 91 | B.12 | 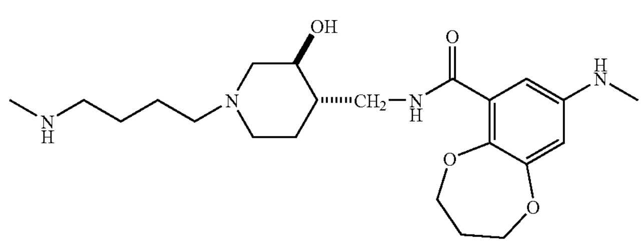 | (trans); mp. 109° C. |
| 92 | B.11 | 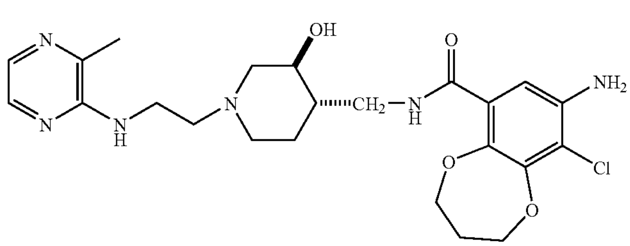 | (trans); mp. 150° C. |

TABLE F-1-continued

| Co. No. | Ex. No. | Structure | Physical data |
|---|---|---|---|
| 93 | B.5 | 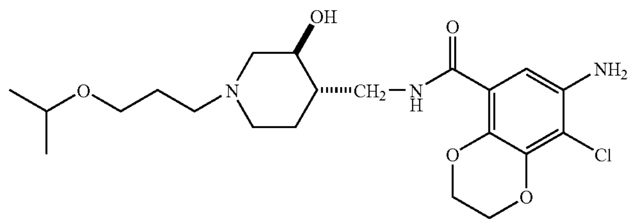 | (trans); ethanedioate (1:2); mp. 139.3-160.5° C. |
| 94 | B.12 | 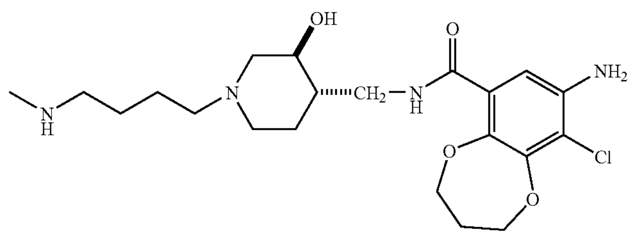 | (trans); mp. 165° C. |
| 95 | B.4 | 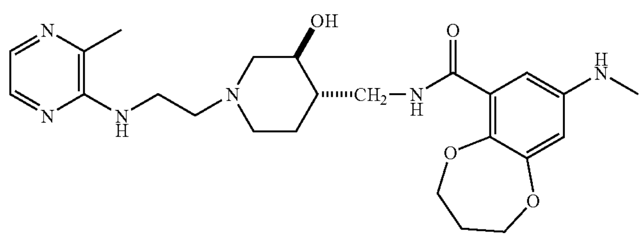 | (trans); mp. 177° C. |
| 96 | B.5 | 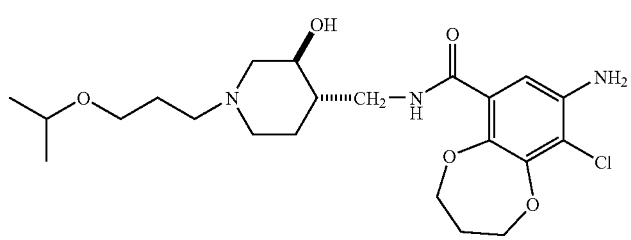 | (trans); mp. 128° C. |
| 97 | B.4 | 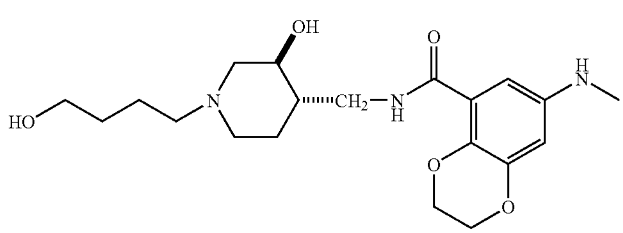 | (trans); (E)-2-butenedioate (2:1); mp. 190° C. |

TABLE F-1-continued

| Co. No. | Ex. No. | Structure | Physical data |
|---|---|---|---|
| 98 | B.2 | 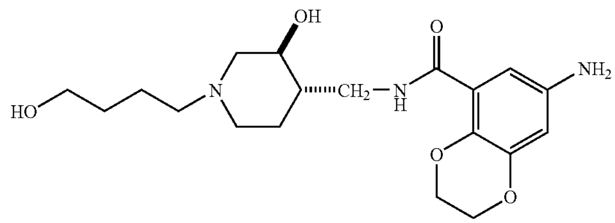 | (trans); (E)-2-butenedioate (2:1); mp. 216° C. |
| 99 | B.2 | 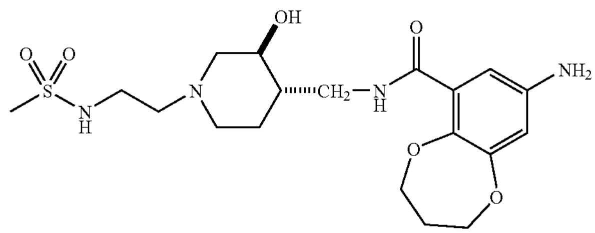 | (trans); mp. 157° C. |
| 100 | B.5 | 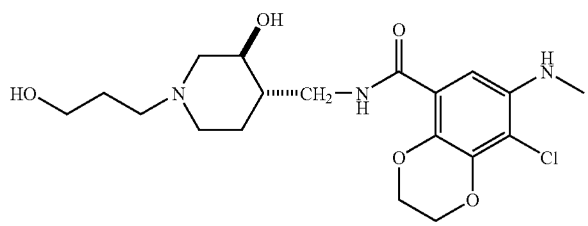 | (trans); mp. 152° C. |
| 101 | B.4 | 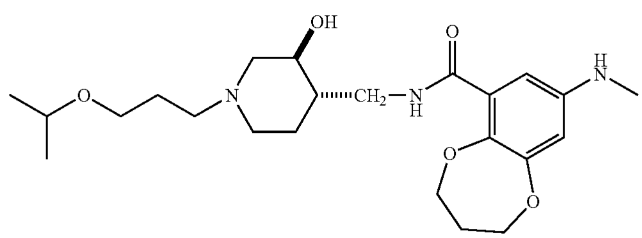 | (trans); mp. 124° C. |
| 102 | B.4 | 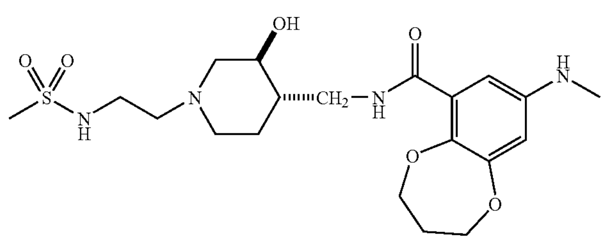 | (trans); HCl (1:2) H$_2$O (2:3) 2-propanolate (2:1), mp. 100° C. |
| 103 | B.4 | 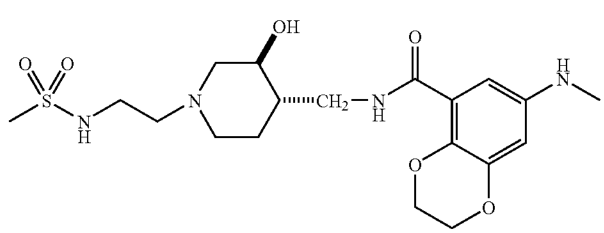 | (trans); HCl (1:2) H$_2$O (1:1) 2-propanolate (1:1); mp. 100° C. |

TABLE F-1-continued

| Co. No. | Ex. No. | Structure | Physical data |
|---|---|---|---|
| 104 | B.2 | 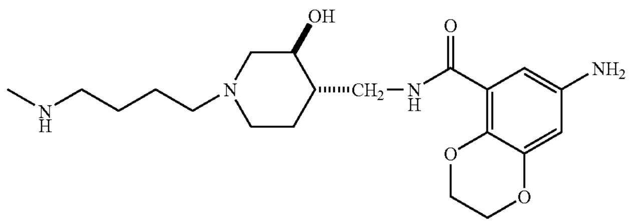 | (trans); HCl (1:2); mp. 100° C. |
| 105 | B.1 | 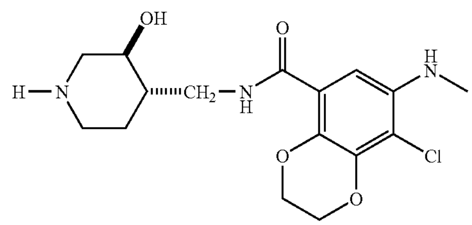 | (trans); (E)-2-butenedioate (2:1) H₂O (1:1); mp. >170° C. |
| 106 | B.2 | 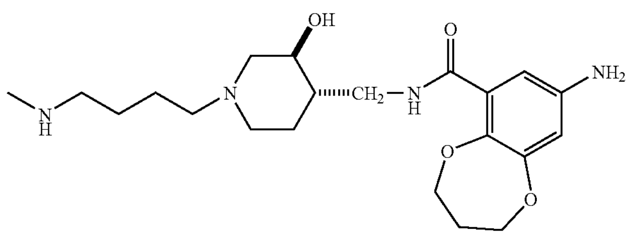 | (trans); ethanedioate (1:2); mp. 100° C. |
| 107 | B.13 | 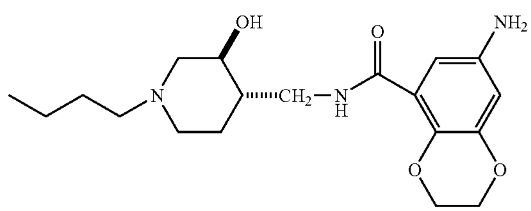 | (trans); ethanedioate (2:3); mp. >160° C. |
| 108 | B.13 | 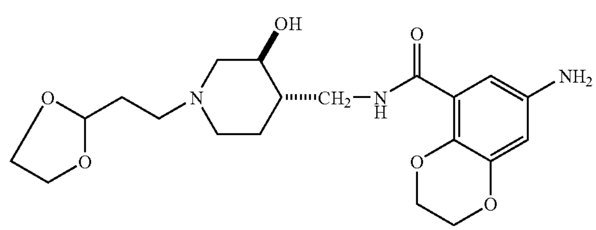 | (trans); mp. 150° C. |
| 109 | B.13 | 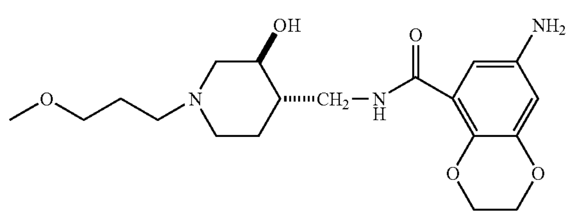 | (trans); HCl (1:2); mp. 205° C. |

TABLE F-1-continued

| Co. No. | Ex. No. | Structure | Physical data |
|---|---|---|---|
| 110 | B.13 | 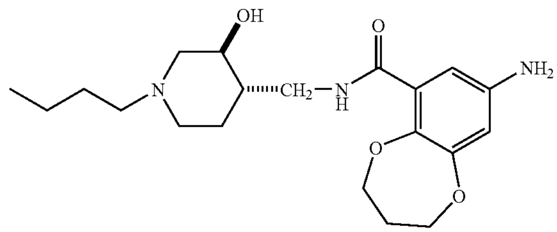 | (trans); HCl (1:2) H₂O (1:1); mp. 200° C. |
| 111 | B.13 | 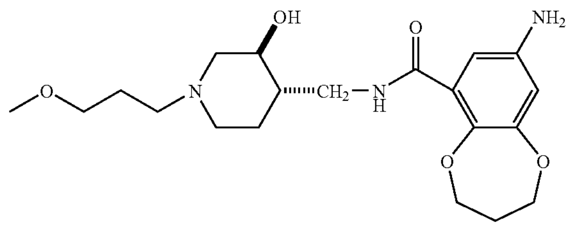 | (trans); HCl (1:2); mp. 174° C. |
| 112 | B.13 | 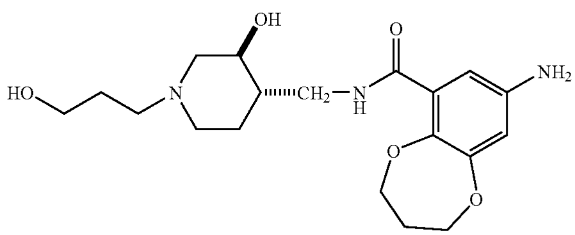 | (trans); mp. 148° C. |
| 113 | B.14 | 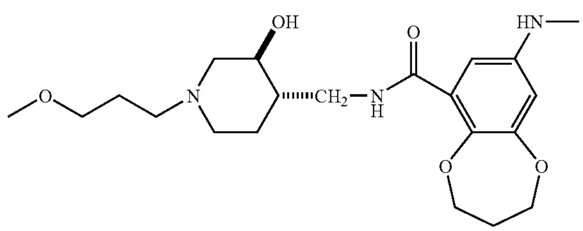 | (trans); mp. 126° C. |
| 114 | B.14 | 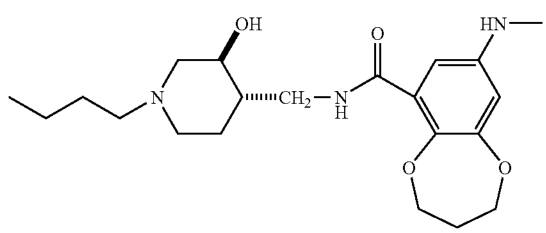 | (trans); HCl (1:2); mp. 176° C. |
| 115 | B.14 | 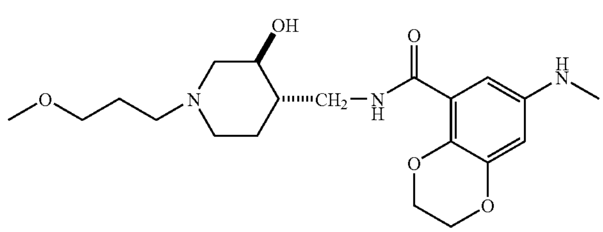 | (trans); HCl (1:2) H₂O (1:1); mp. 157.7-182.2° C. |

TABLE F-1-continued
| Co. No. | Ex. No. | Structure | Physical data |
|---|---|---|---|
| 116 | B.14 | 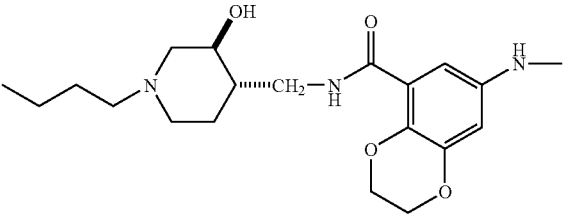 | (trans); HCl (1:2) H₂O (1:1); mp. 186.8-210.3° C. |
| 117 | B.13 | 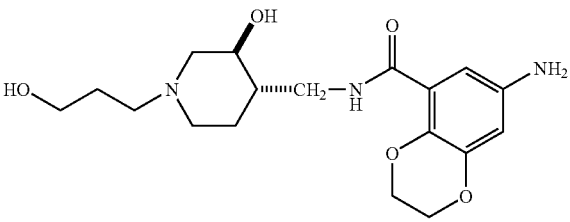 | (trans); mp. 156° C. |
| 118 | B.13 | 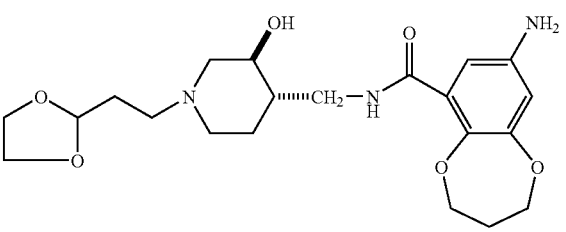 | (trans); mp. 132° C. |
| 119 | B.8 | 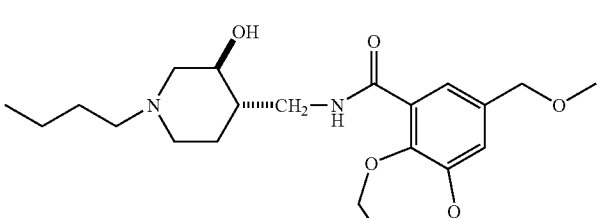 | (trans); ethanedioate (1:1); mp. 114° C. |
| 120 | B.8 | 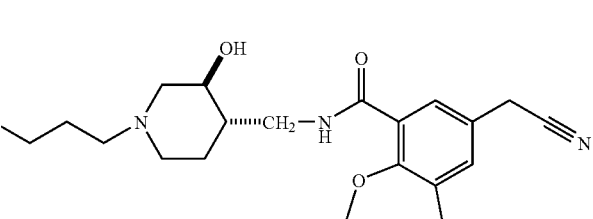 | (trans); mp. 157° C. |
| 121 | B.1 | 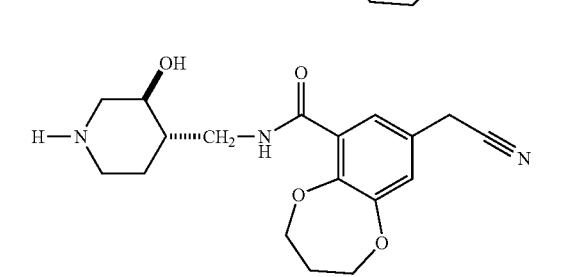 | (trans); ethanedioate (1:1) H₂O (1:1); mp. 103° C. |

TABLE F-1-continued

| Co. No. | Ex. No. | Structure | Physical data |
|---|---|---|---|
| 122 | B.8 | 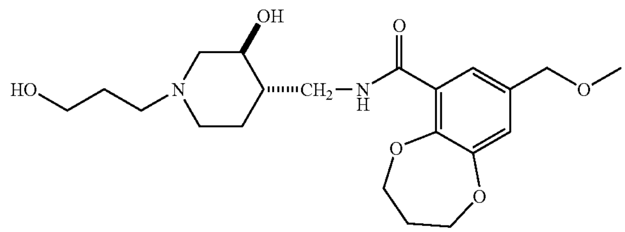 | (trans); mp. 110° C. |
| 123 | B.8 | 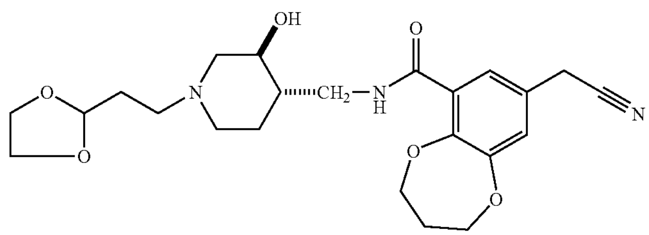 | (trans); ethanedioate (1:1); mp. 137° C. |
| 124 | B.8 | 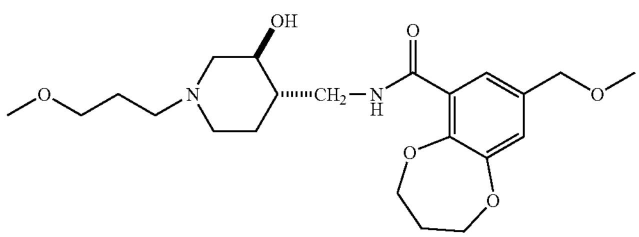 | (trans); ethanedioate (1:1); mp. 124° C. |
| 125 | B.8 | 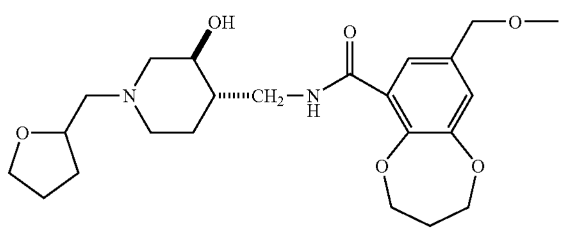 | (trans); ethanedioate (1:1); mp. 104° C. |
| 126 | B.8 | 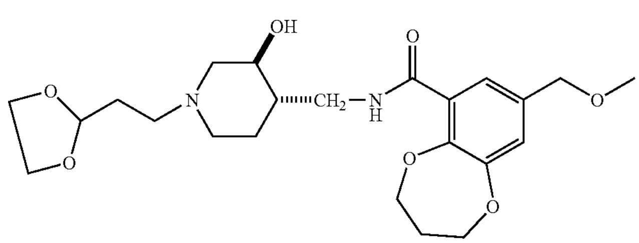 | (trans); ethanedioate (1:1); mp. 142° C. |
| 127 | B.8 | 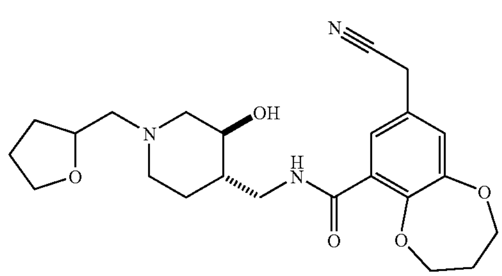 | (trans); ethanedioate (1:1); mp. 96° C. |

TABLE F-1-continued

| Co. No. | Ex. No. | Structure | Physical data |
|---|---|---|---|
| 128 | B.5 | 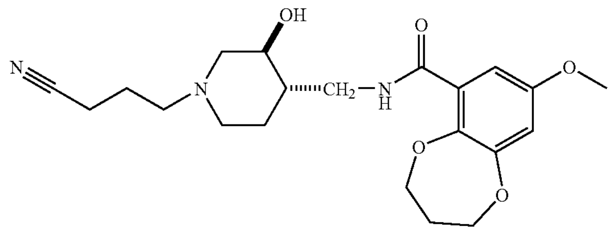 | (trans); ethanedioate (1:1); mp. 108° C. |
| 129 | B.8 | 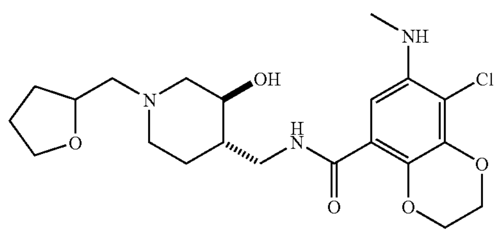 | (trans); mp. >60° C. |
| 130 | B.8 | 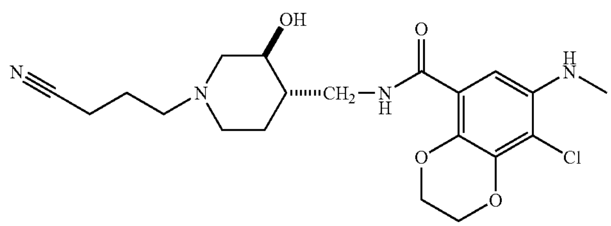 | (trans); mp. 188° C. |
| 131 | B.8 | 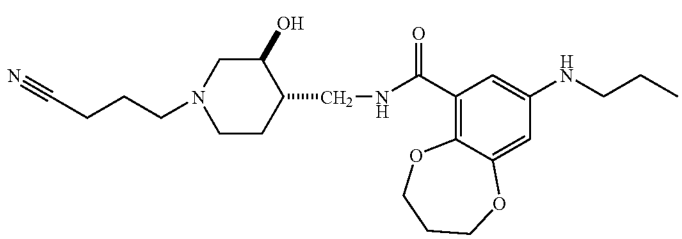 | (trans); mp. 132° C. |
| 132 | B.2 | 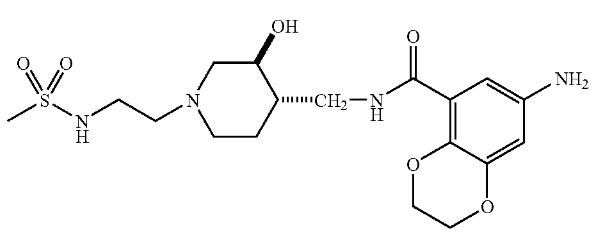 | (trans); (E)-2-butenedioate (2:1) H₂O (1:1) 2-propanolate (2:1); mp. 100° C. |
| 133 | B.1 | 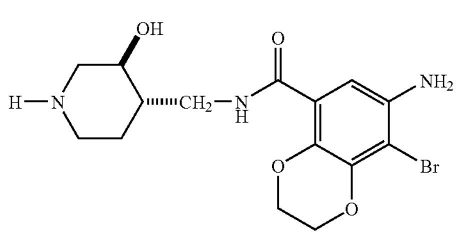 | (trans); HCl (1:1) H₂O (1:1); mp. 185° C. |

TABLE F-1-continued

| Co. No. | Ex. No. | Structure | Physical data |
|---|---|---|---|
| 134 | B.8 | 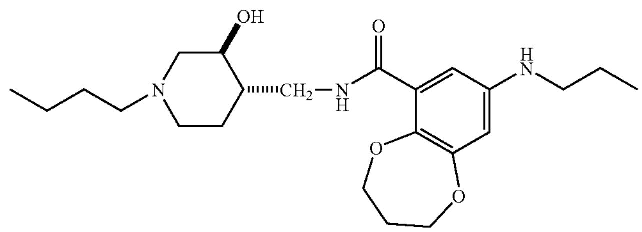 | (trans); mp. 131 ° C. |
| 135 | B.8 | 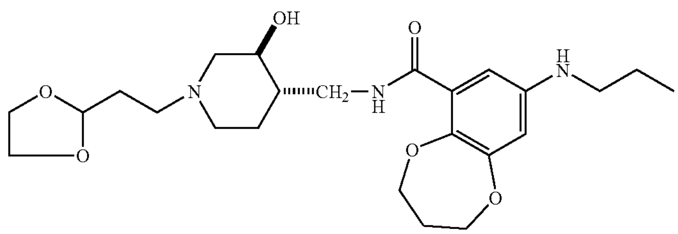 | (trans); mp. 120° C. |
| 136 | B.4 | 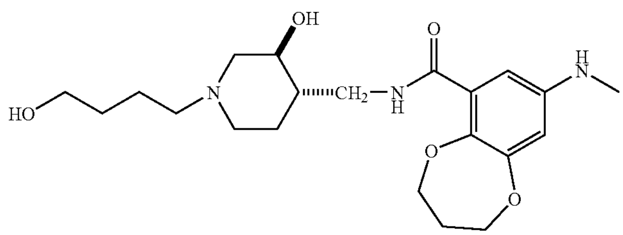 | (trans); mp. 92° C. |
| 137 | B.5 | 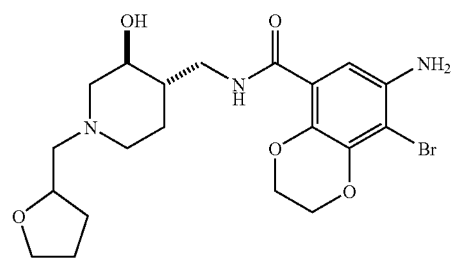 | (trans); mp. 100° C. |
| 138 | B.5 | 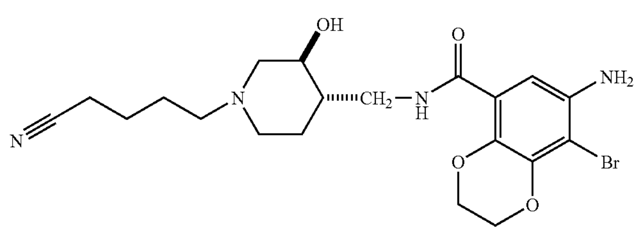 | (trans); mp. 132° C. |
| 139 | B.5 | 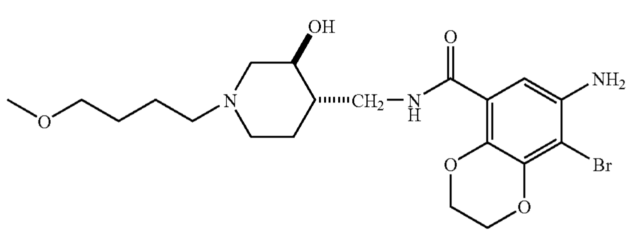 | (trans); mp. 136° C. |

TABLE F-1-continued

| Co. No. | Ex. No. | Structure | Physical data |
|---|---|---|---|
| 140 | B.5 | 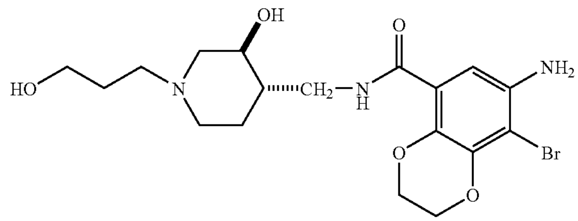 | (trans); mp. 160° C. |
| 141 | B.5 | 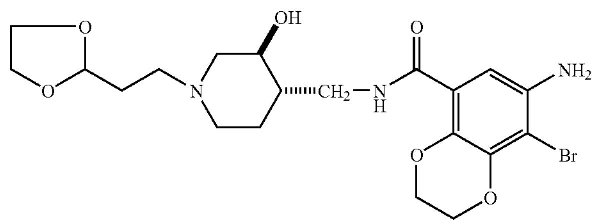 | (trans); mp. 150° C. |
| 142 | B.1 | 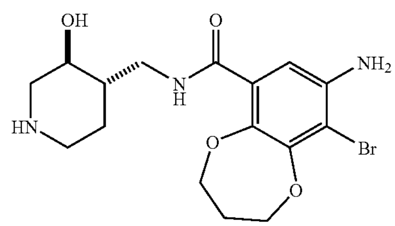 | (trans); HCl (1:2); mp. >260° C. |
| 143 | B.8 | 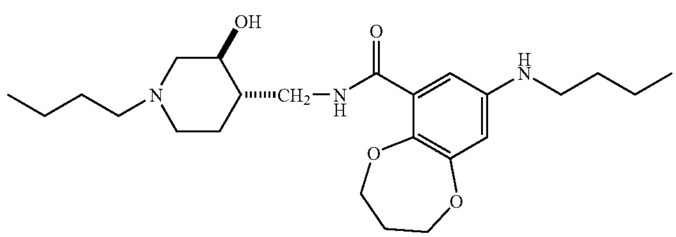 | (trans); mp. 120° C. |
| 144 | B.8 | 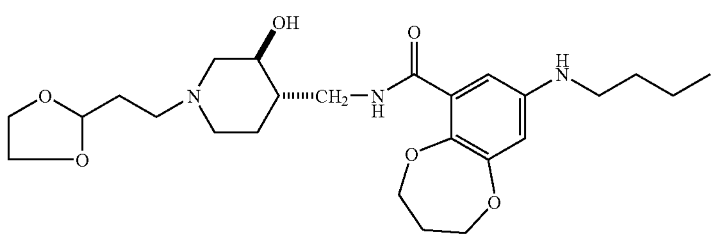 | (trans); mp. 132° C. |
| 145 | B.5 | 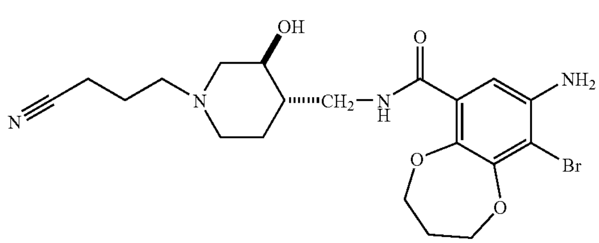 | (trans); mp. 162° C. |

TABLE F-1-continued

| Co. No. | Ex. No. | Structure | Physical data |
|---|---|---|---|
| 146 | B.5 | 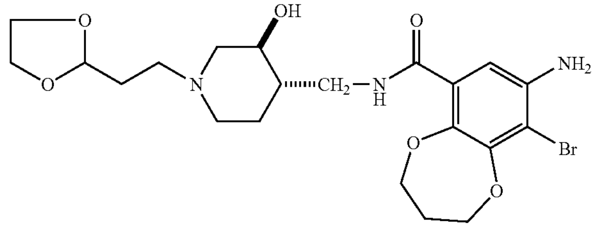 | (trans); mp. 150° C. |
| 147 | B.5 | 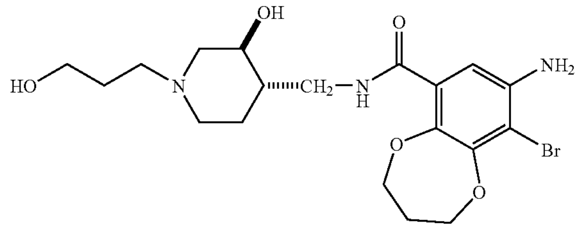 | (trans); mp. 170° C. |
| 148 | B.8 | 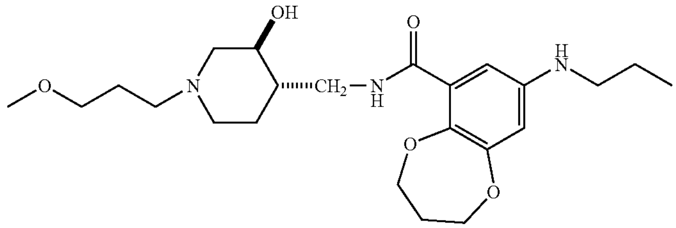 | (trans); mp. 96-98° C. |
| 149 | B.1 | 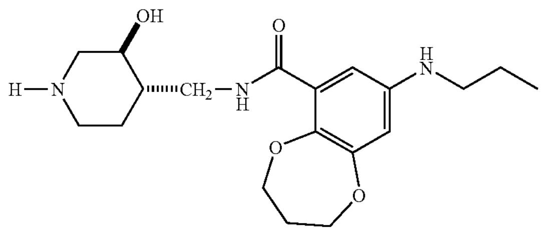 | (trans); (E)-2-butenedioate (2:3) H₂O (2:1); mp. >115° C. |
| 150 | B.8 | 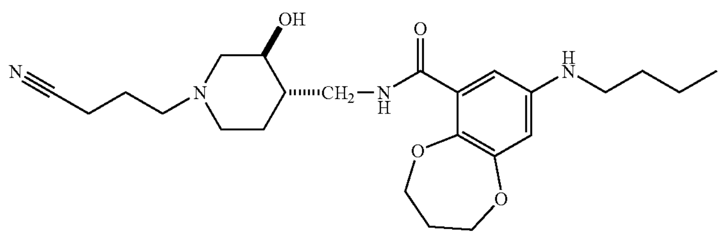 | (trans); (E)-2-butenedioate (1:1); mp. 160° C. |
| 151 | B.8 | 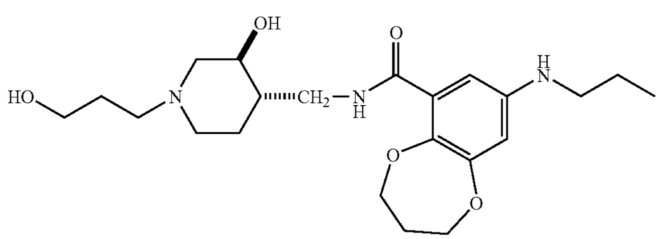 | (trans); mp. 110° C. |

TABLE F-1-continued

| Co. No. | Ex. No. | Structure | Physical data |
|---|---|---|---|
| 152 | B.5 | 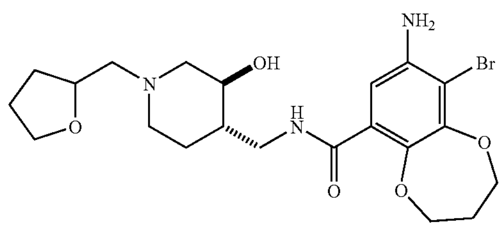 | (trans); mp. 135° C. |
| 153 | B.6 | 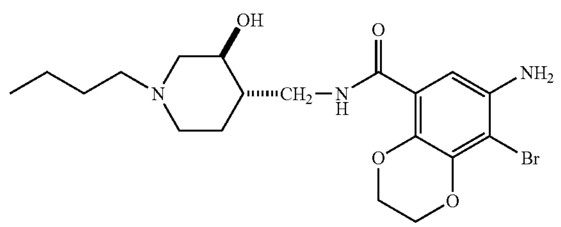 | (trans); mp. 110° C. |
| 154 | B.1 | 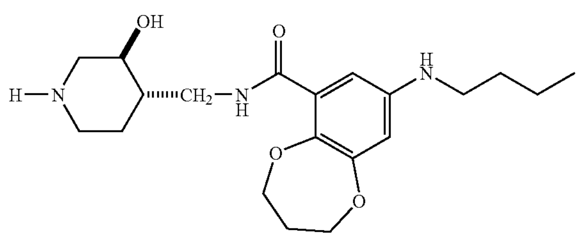 | (trans); HCl (3:2) H$_2$O (4:1); mp. 220° C. |
| 155 | B.5 | 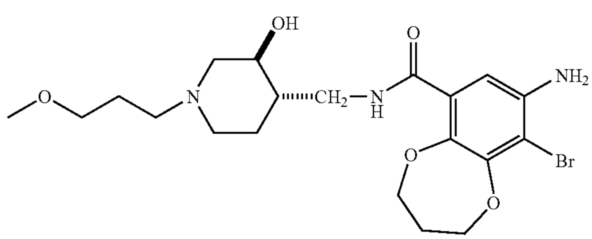 | (trans); mp. 146° C. |
| 156 | B.8 | 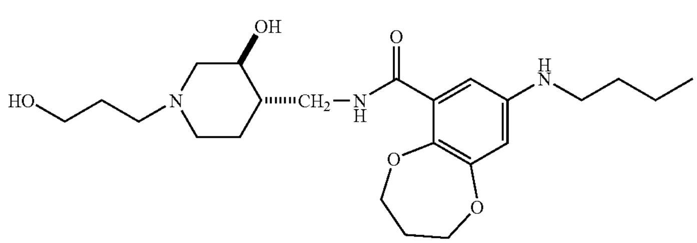 | (trans); mp. 119° C. |
| 157 | B.8 | 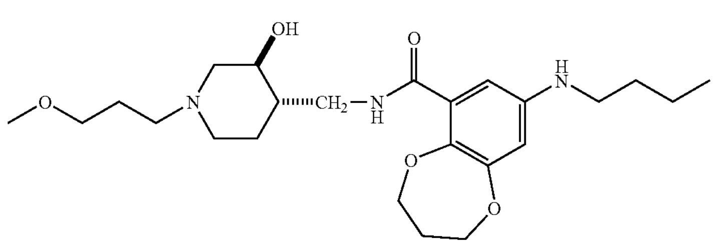 | (trans); mp. 97° C. |

TABLE F-1-continued

| Co. No. | Ex. No. | Structure | Physical data |
|---|---|---|---|
| 158 | B.8 | 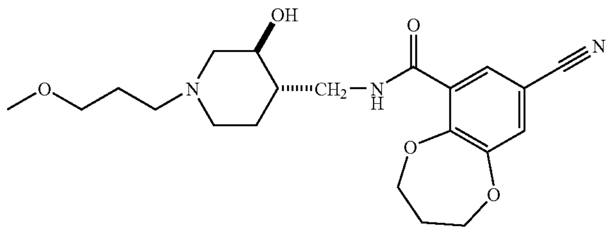 | (trans); H₂O (1:1); mp. >75° C. |
| 159 | B.8 | 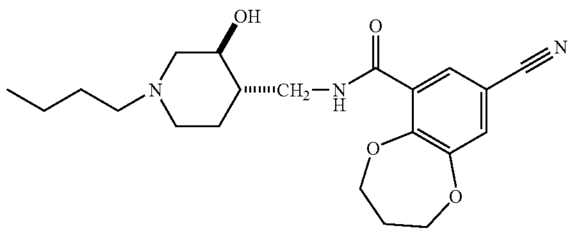 | (trans); mp. 104° C. |
| 160 | B.8 | 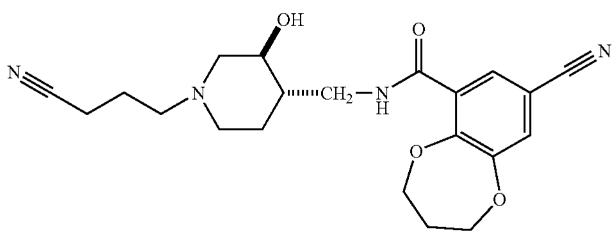 | (trans); mp. 108° C. |
| 161 | B.8 | 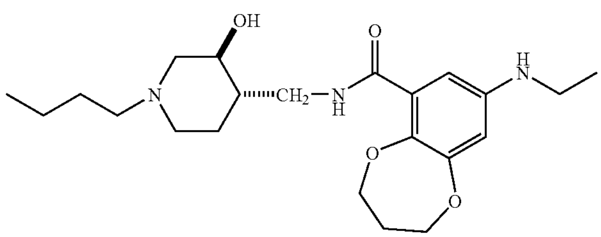 | (trans); mp. 132° C. |
| 162 | B.8 | 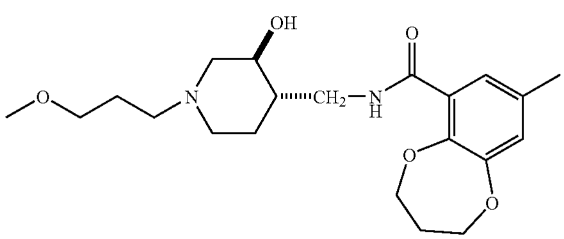 | (trans); ethanedioate (1:1); mp. 100° C. |
| 163 | B.8 | 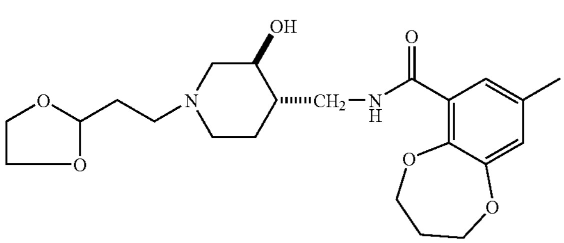 | (trans); ethanedioate (1:1); mp. 76° C. |

TABLE F-1-continued

| Co. No. | Ex. No. | Structure | Physical data |
|---|---|---|---|
| 164 | B.8 | 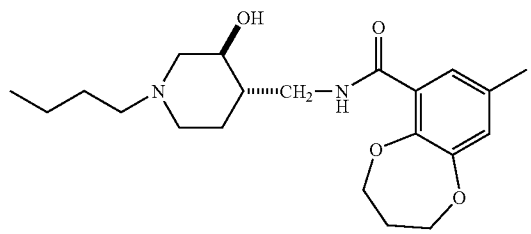 | (trans); ethanedioate (1:1) H$_2$O (1:1); mp. 112° C. |
| 165 | B.8 | 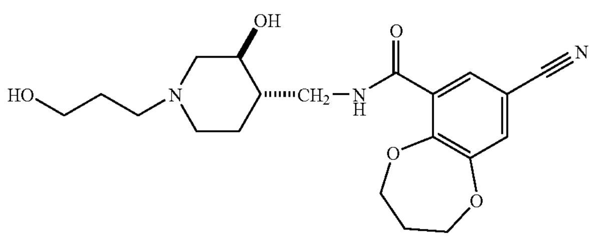 | (trans); mp. 138° C. |
| 166 | B.8 | 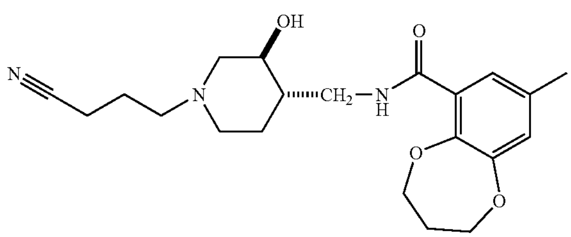 | (trans); mp. 110° C. |
| 167 | B.1 | 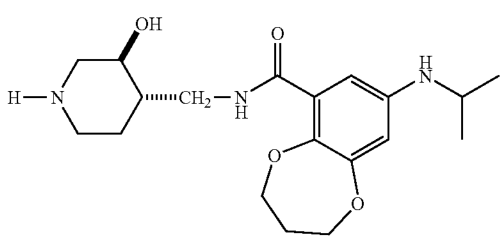 | (trans); ethanedioate (1:1); mp. 130° C. |
| 168 | B.8 | 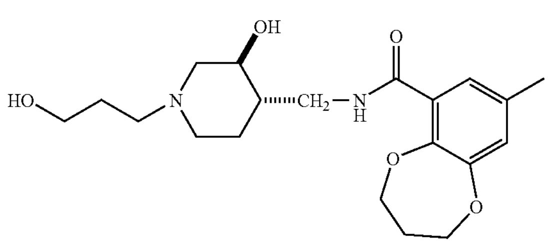 | (trans); ethanedioate (1:1); mp. 72° C. |
| 169 | B.8 | 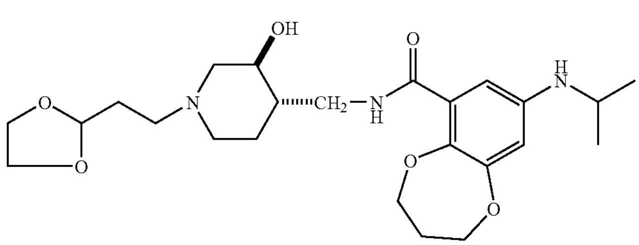 | (trans); mp. 110° C. |

TABLE F-1-continued

| Co. No. | Ex. No. | Structure | Physical data |
|---|---|---|---|
| 170 | B.8 | 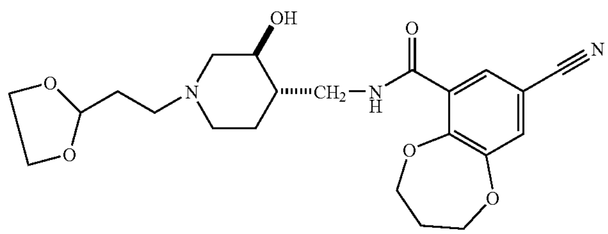 | (trans); H₂O (1:1); mp. 90° C. |
| 171 | B.14 | 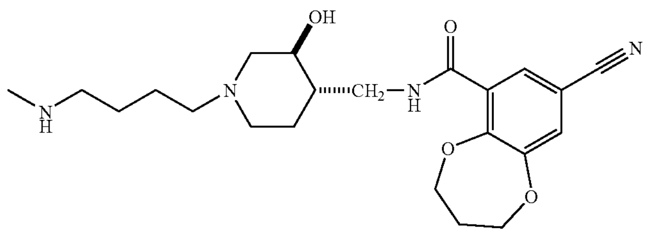 | (trans); mp. 150° C. |
| 172 | B.8 | 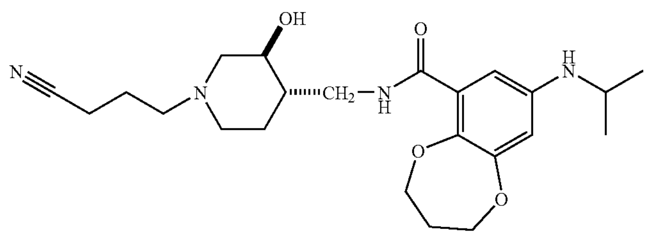 | (trans); ethanedioate (1:1); mp. 120° C. |
| 173 | B.14 | 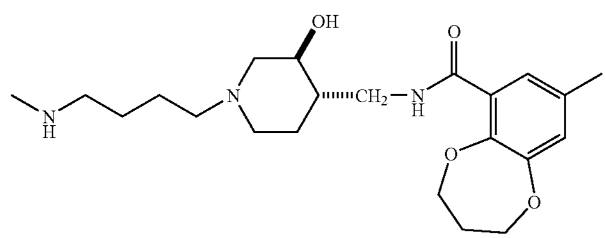 | (trans); ethanedioate (1:2); mp. 100° C. |
| 174 | B.8 | 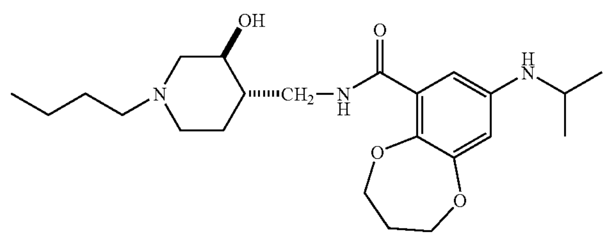 | (trans); ethanedioate (1:1) H₂O (1:1); mp. 110° C. |
| 175 | B.1 | 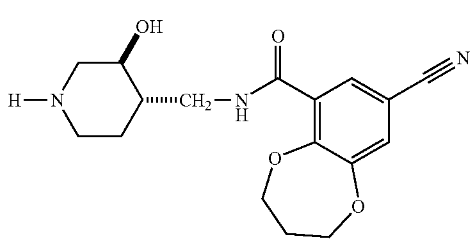 | (trans); mp. 138° C. |

TABLE F-1-continued

| Co. No. | Ex. No. | Structure | Physical data |
|---|---|---|---|
| 176 | B.8 | 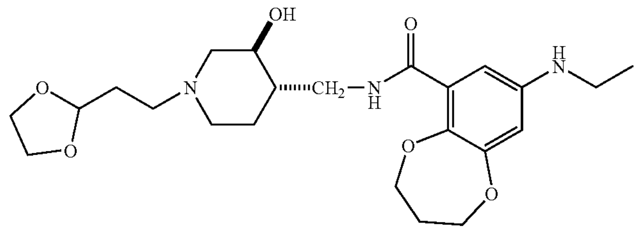 | (trans); mp. 148° C. |
| 177 | B.8 | 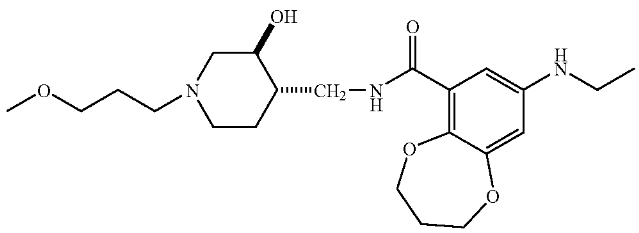 | (trans); mp. 120° C. |
| 178 | B.1 | 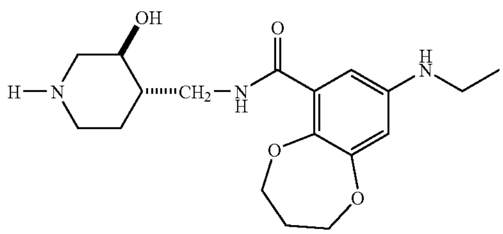 | (trans); ethanedioate (1:1); mp. 240° C. |
| 179 | B.8 | 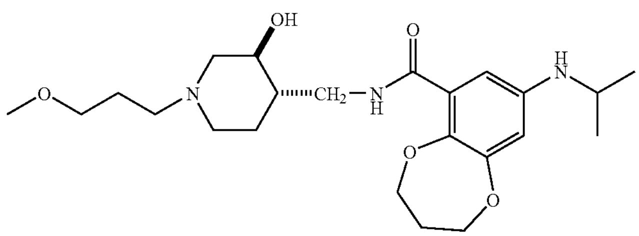 | (trans); ethanedioate (1:1); mp. 100° C. |
| 180 | B.5 | 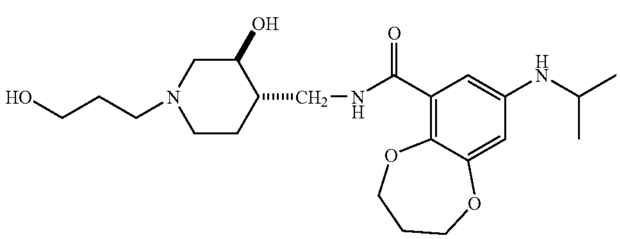 | (trans); mp. 130° C. |
| 181 | B.6 | 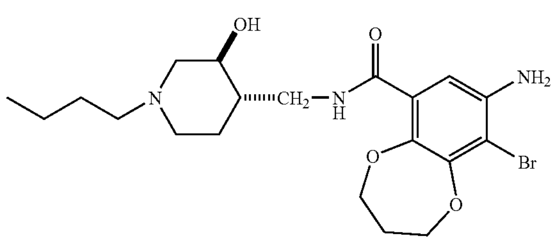 | (trans); mp. 130° C. |

TABLE F-1-continued

| Co. No. | Ex. No. | Structure | Physical data |
|---|---|---|---|
| 182 | B.8 | 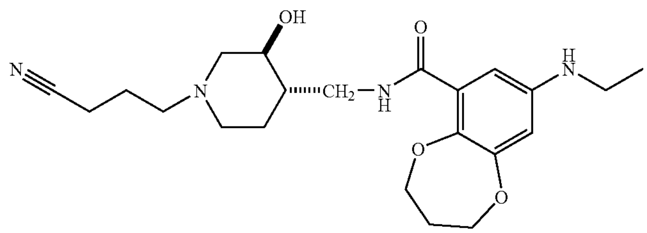 | (trans); mp. 146° C. |
| 183 | B.8 | 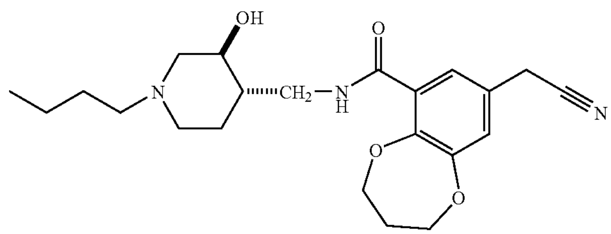 | (trans); mp. 123° C. |
| 184 | B.8 | 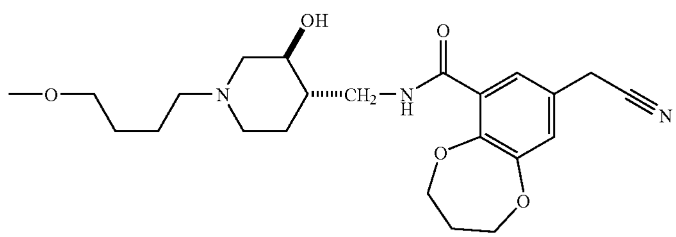 | (trans); mp. 85° C. |
| 185 | B.5 | 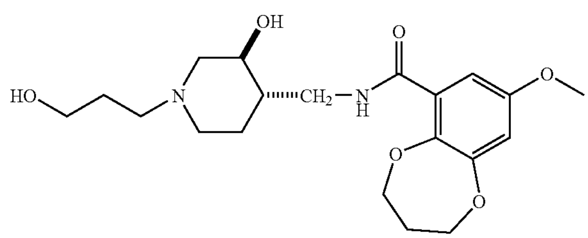 | (trans); mp. 108° C. |
| 186 | B.8 | 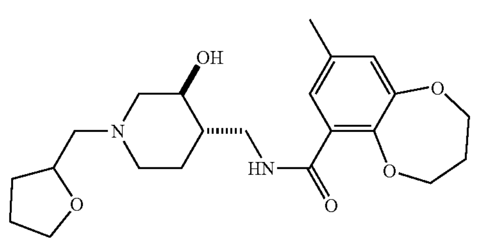 | (trans); ethanedioate (1:1); mp. 154° C. |
| 187 | B.5 | 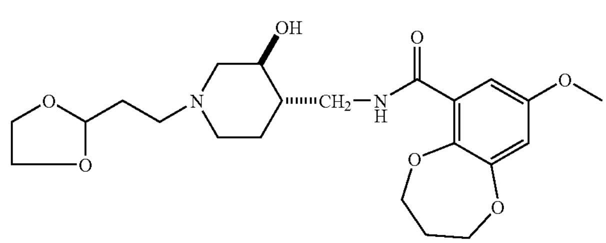 | (trans); mp. 125° C. |

TABLE F-1-continued

| Co. No. | Ex. No. | Structure | Physical data |
|---|---|---|---|
| 188 | B.1 | 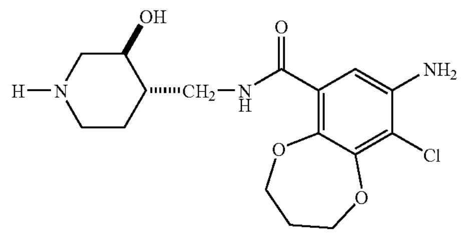 | (trans) |
| 189 | B.5 | 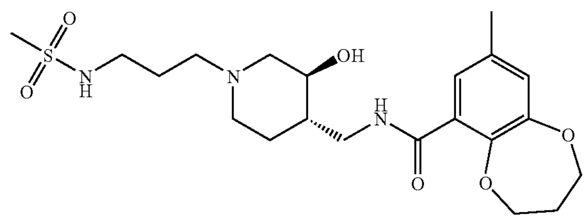 | (3S-trans); mp. 125° C.; $[\alpha]^{20,D} = -9.51°$ (c = 21.56 mg/5 ml in methanol) |
| 190 | B.1 | 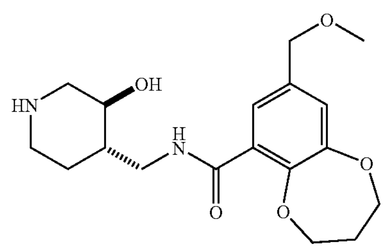 | (trans); ethanedioate (1:1); mp. 160° C. |
| 191 | B.7 | 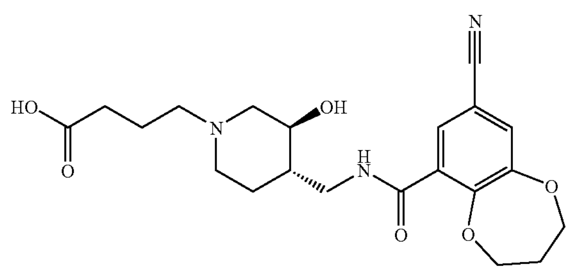 | (3S-trans); |
| 192 | B.7 | 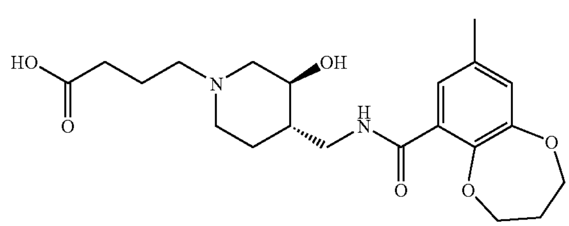 | (3S-trans); mp. 234° C.; $[\alpha]^{20,D} = -16.66°$ (c = 22.51 mg/5 ml in methanol) |
| 193 | B.15 | 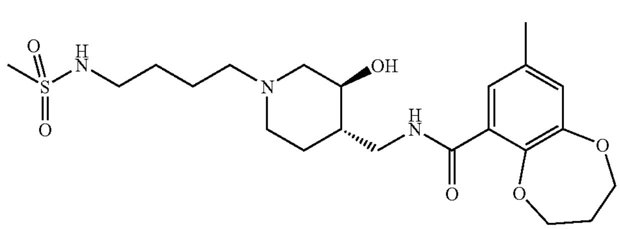 | (3S-trans); mp. 134° C.; $[\alpha]^{20,D} = -9.83°$ (c = 23.40 mg/5 ml in methanol) |

TABLE F-1-continued

| Co. No. | Ex. No. | Structure | Physical data |
|---|---|---|---|
| 194 | B.5 | 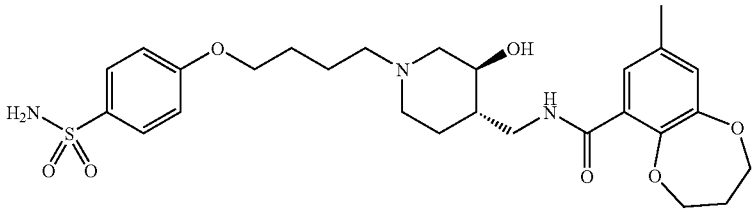 | (3S-trans); ethanedioate (1:1) 2-propanol (2:1); mp. >80° C.; $[\alpha]^{20,D} = -9.37°$ (c = 22.41 mg/5 ml in methanol) |
| 195 | B.6 | 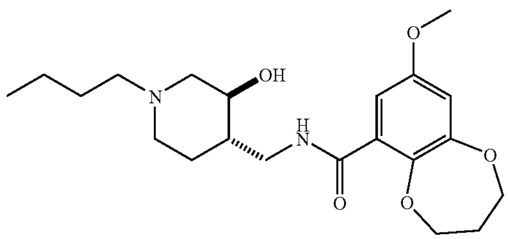 | (trans); ethanedioate (1:1); mp. 172° C. |
| 196 | B.5 | 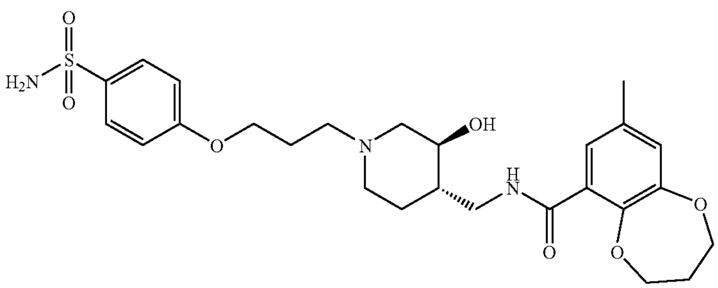 | (3S-trans); mp. 118° C.; $[\alpha]^{20,D} = -7.94°$ (c = 9.82 mg/2 ml in $CH_3OH$) |
| 197 | B.16 | 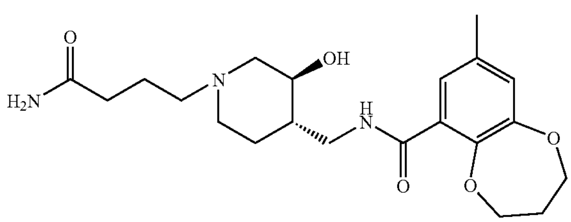 | (3S-trans); mp. 136° C.; $[\alpha]^{20,D} = -11.52°$ (c = 10.42 mg/5 ml in $CH_3OH$) |
| 198 | B.5 | 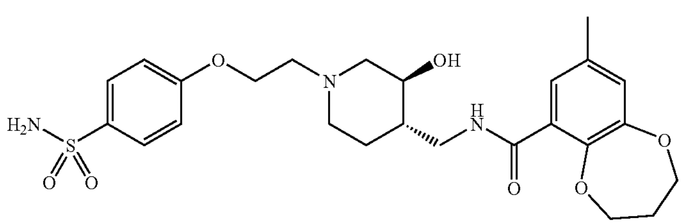 | (3S-trans); (E)-2-butenedioate (3:2) 2-propanolate (1:1); mp. >70° C.; $[\alpha]^{20,D} = -7.96°$ (c = 21.99 mg/5 ml in methanol) |
| 199 | B.12 | 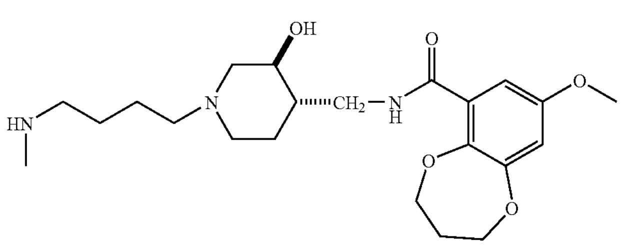 | (trans); ethanoldioate (1:1); mp. 146° C. |

TABLE F-1-continued

| Co. No. | Ex. No. | Structure | Physical data |
|---|---|---|---|
| 200 | B.5 | 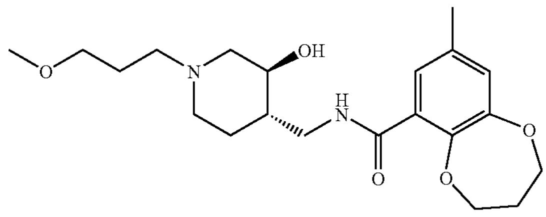 | (3S-trans); mp. 108° C.; $[\alpha]^{20,D} = -10.70°$ (c = 10.28 mg/2 ml in methanol) |
| 201 | B.5 | 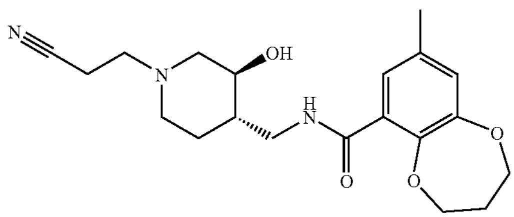 | (3S-trans); mp. 84-86° C.; $[\alpha]^{20,D} = -10.03°$ (c = 24.93 mg/5 ml in methanol) |
| 202 | B.5 | 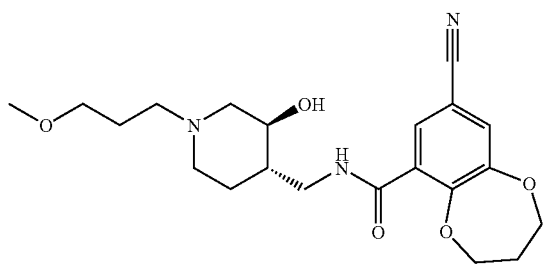 | (3S-trans); mp. 108° C., $[\alpha^{20,D} = -8.70°$ (c = 25.86 mg/5 ml in methanol) |
| 203 | B.1 | 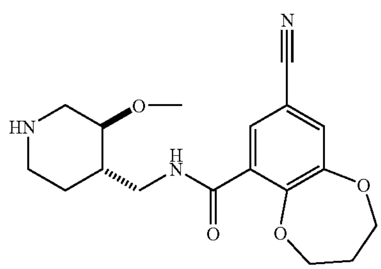 | (trans); ethanedioate (1:1); mp. 192.3-200.4° C. |
| 204 | B.1 | 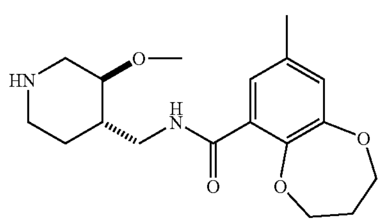 | (trans); ethanedioate (1:1); mp. 145° C. |
| 205 | B.5 | 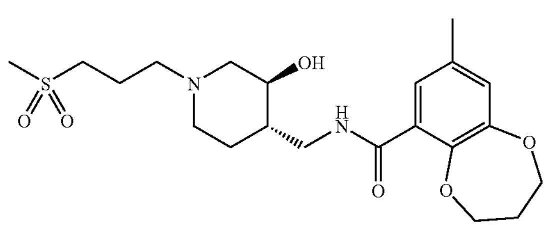 | (3S-trans); mp. 122° C.; $[\alpha]^{20,D} = -8.97°$ (c = 23.42 mg/5 ml in methanol) |

TABLE F-1-continued

| Co. No. | Ex. No. | Structure | Physical data |
|---|---|---|---|
| 206 | B.5 | 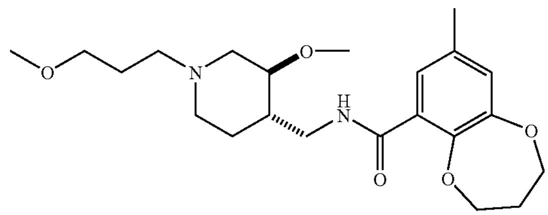 | (trans); ethanedioate (1:1); mp. 101.0-129.3° C. |
| 207 | B.5 | 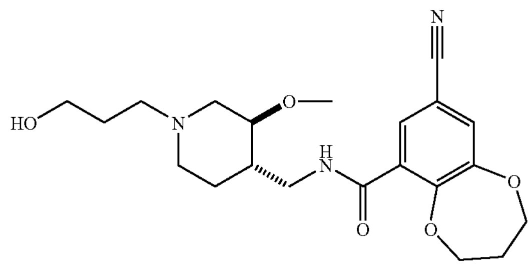 | (trans); mp. 128.2-135.1° C. |
| 208 | B.5 | 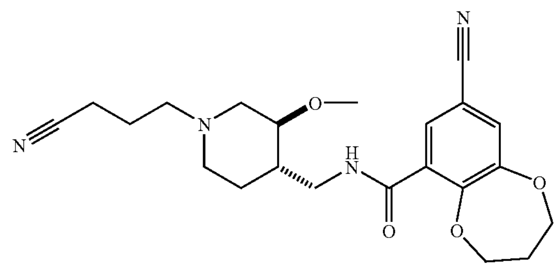 | (trans); ethanedioate (1:1); mp. 175.3-186.2° C. |
| 209 | B.6 | 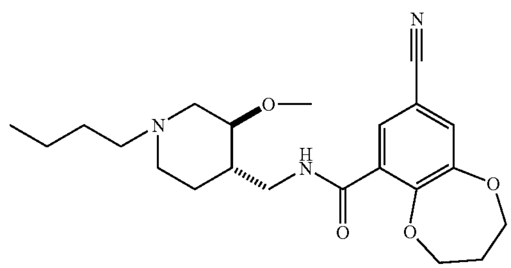 | (trans); ethanedioate (1:1); mp. 168.4-191.9° C. |
| 210 | B.5 | 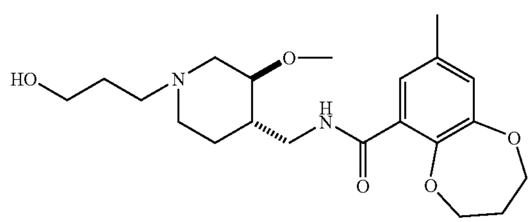 | (trans); ethanedioate (1:1); mp. 134.6-139.7° C. |
| 211 | B.5 | 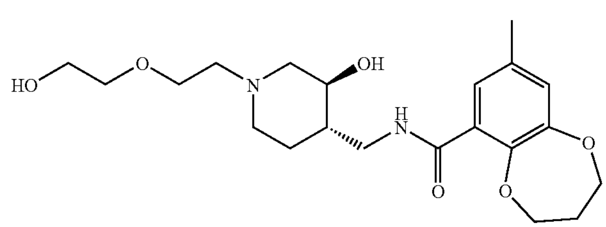 | (3S-trans); mp. 79° C.; $[\alpha]^{20,D} = -10.54°$ (c = 24.19 mg/5 ml in methanol) |

TABLE F-1-continued

| Co. No. | Ex. No. | Structure | Physical data |
|---|---|---|---|
| 212 | B.5 | 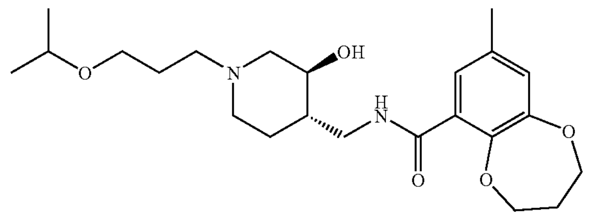 | (3S-trans); (E)-2-butenedioate (1:1); mp. 150° C.; $[\alpha]^{20,D} = -10.59°$ (c = 22.67 mg/5 ml in methanol) |
| 213 | B.5 | 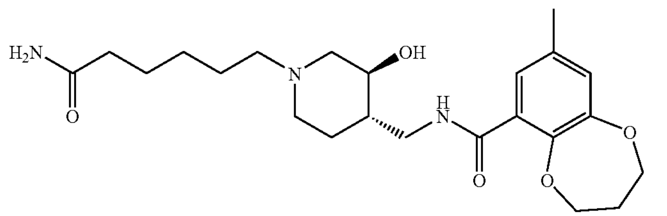 | (3S-trans); mp. >113° C.; $[\alpha]^{20,D} = -10.57°$ (c = 23.66 mg/5 ml in methanol) |
| 214 | B.5 | 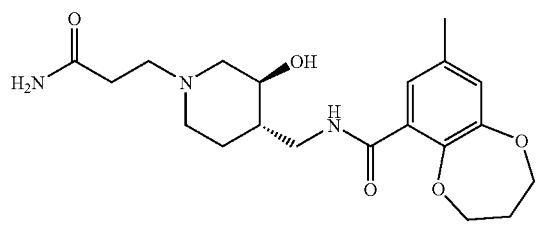 | (3S-trans); mp. 160° C.; $[\alpha]^{20,D} = -11.60°$ (c = 22.85 mg/5 ml in methanol) |
| 215 | B.5 | 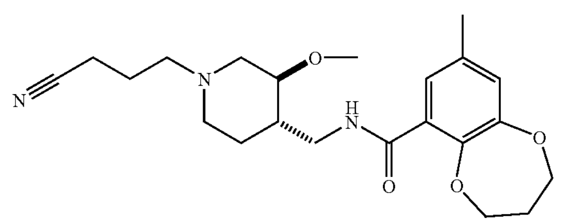 | (trans); ethanedioate (1:1); mp. 90.5-141.5° C. |
| 216 | B.4 | 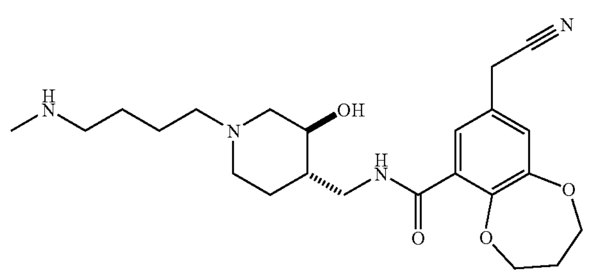 | (trans) |
| 217 | B.5 | 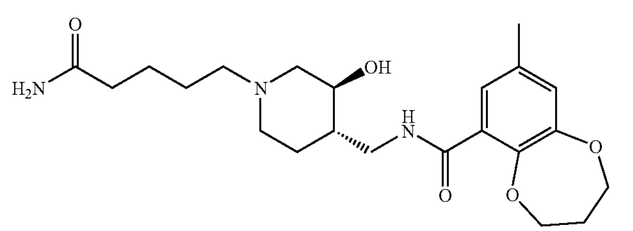 | (3S-trans); mp. 155° C.; $[\alpha]^{20,D} = -10.13°$ (c = 24.69 mg/5 ml in methanol) |

TABLE F-1-continued

| Co. No. | Ex. No. | Structure | Physical data |
|---|---|---|---|
| 218 | B.5 | 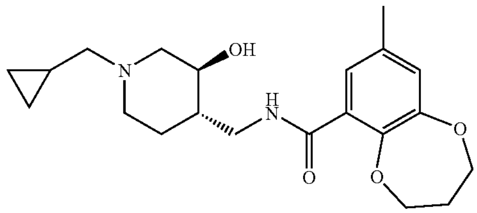 | (3S-trans); mp. 91° C.; $[\alpha]^{20,D} = -13.40°$ (c = 23.50 mg/5 ml in methanol) |
| 219 | B.5 | 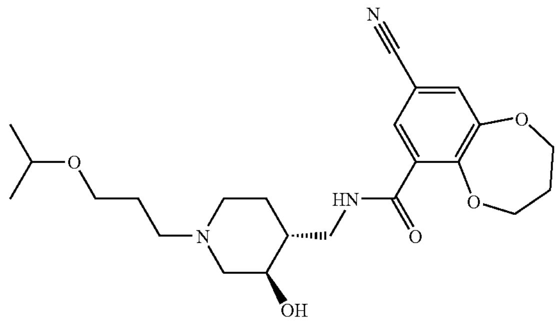 | (3S-trans); ethanedioate (1:1); mp. 149.4-156.4° C. |
| 220 | B.5 | 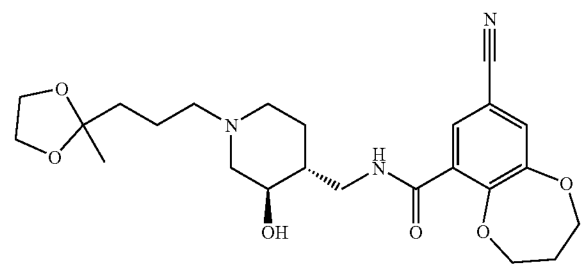 | (3S-trans); ethanedioate (1:1); mp. 128.2-132.1° C. |
| 221 | B.5 | 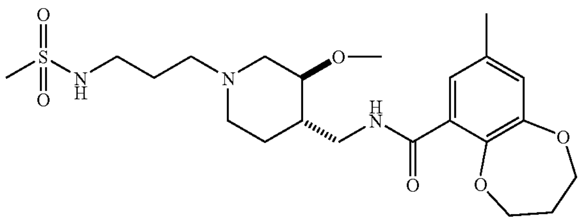 | (trans); ethanedioate (1:1); mp. 110.2-121.2° C. |
| 222 | B.6 | 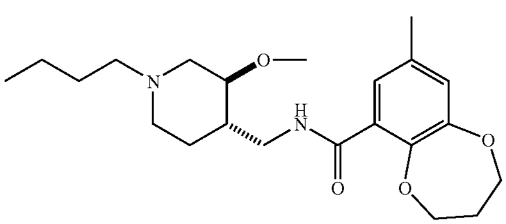 | (trans); ethanedioate (1:1); mp. 160.0-184.3° C. |
| 223 | B.9 | 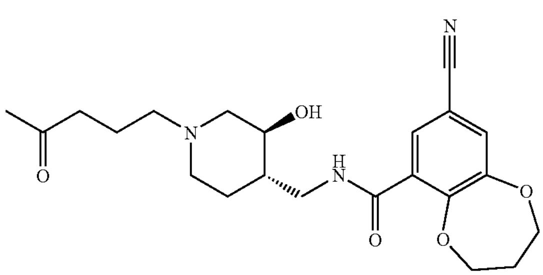 | (3S-trans); ethanedioate (1:1); mp. 152° C. |

TABLE F-1-continued

| Co. No. | Ex. No. | Structure | Physical data |
|---|---|---|---|
| 224 | B.5 | 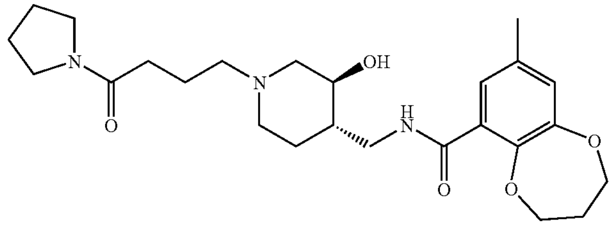 | (3S-trans); ethanedioate (1:1); mp. 159° C. |
| 225 | B.5 | 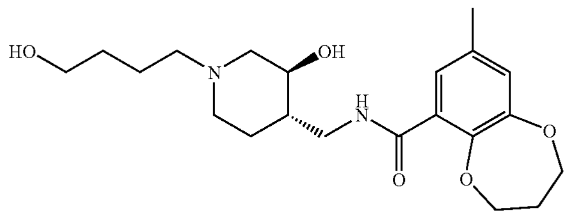 | (3S-trans); ethanedioate (1:1); mp. >65° C. |
| 226 | B.5 | 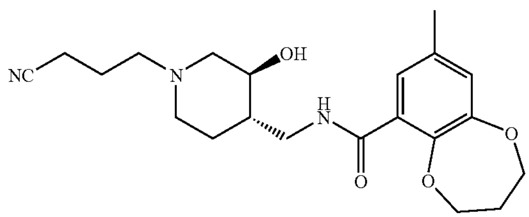 | (3S-trans); |
| 227 | B.5 | 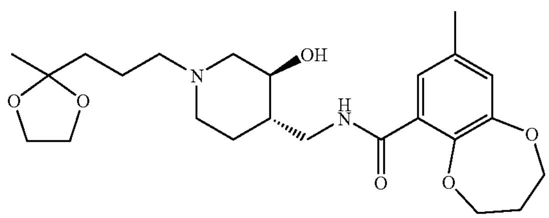 | (3S-trans); ethanedioate (1:1); mp. 160° C. |
| 228 | B.5 | 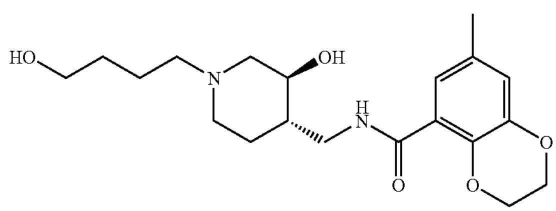 | (3S-trans); $[\alpha]^{20,D} = -14.73°$ (c = 10.18 mg/2 ml in methanol) |
| 229 | B.9 | 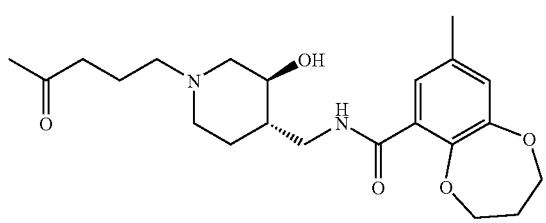 | (3S-trans); ethanedioate (1:1); $[\alpha]^{20,D} = -11.49°$ (c = 23.94 mg/5 ml in methanol) |
| 230 | B.11 | 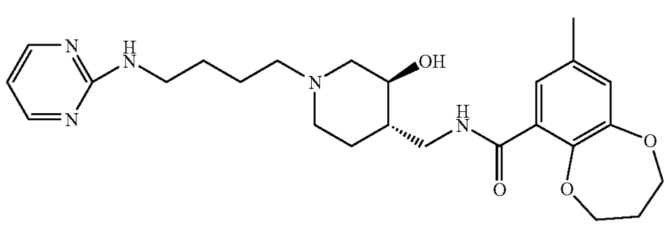 | (3S-trans); ethanedioate (1:1) $H_2O$ (1:1); mp. >94° C. |

TABLE F-1-continued

| Co. No. | Ex. No. | Structure | Physical data |
|---|---|---|---|
| 231 | B.11 | 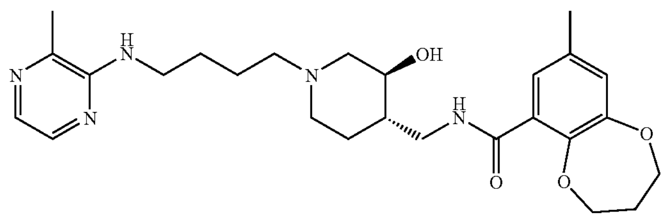 | (3S-trans); ethanedioate (1:1) H$_2$O (1:1); mp. >90° C. |
| 232 | B.5 | 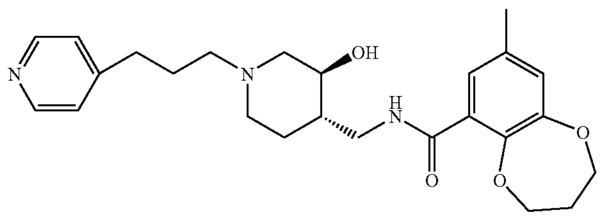 | (3S-trans); mp. 150° C. |
| 233 | B.5 | 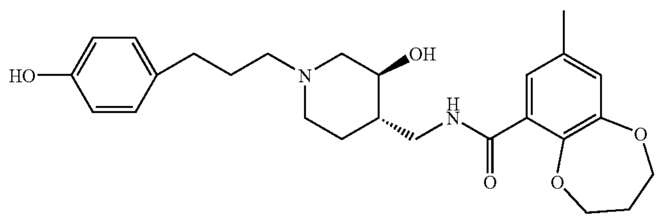 | (3S-trans); mp. 156° C. |
| 234 | B.5 | 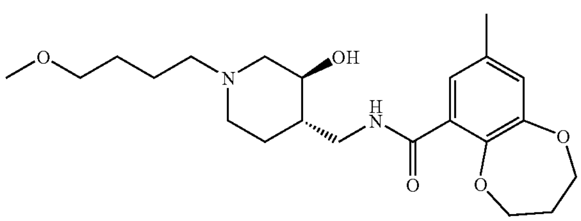 | (3S-trans); ethanedioate (1:1); $[\alpha]^{20,D} = -10.69°$ (c = 30.87 mg/5 ml in methanol) |
| 235 | B.5 | 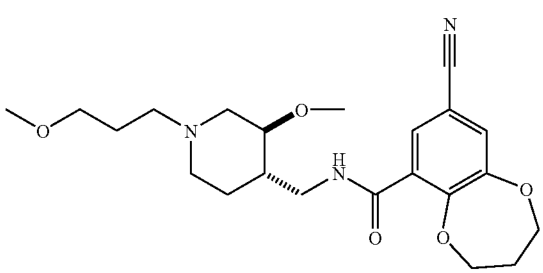 | (trans); ethanedioate (1:1) |
| 236 | B.5 | 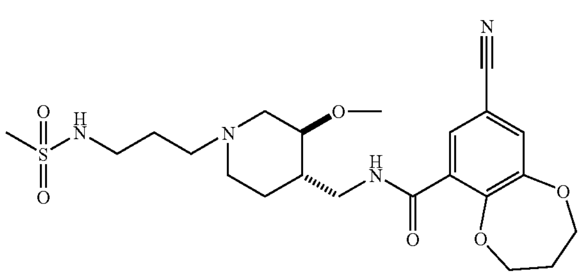 | (trans) |

TABLE F-1-continued

| Co. No. | Ex. No. | Structure | Physical data |
|---|---|---|---|
| 237 | B.5 | 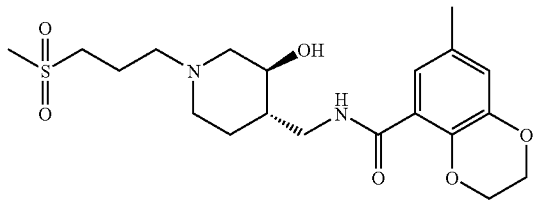 | (3S-trans); ethanedioate (1:1); mp. 90° C. |
| 238 | B.17 | 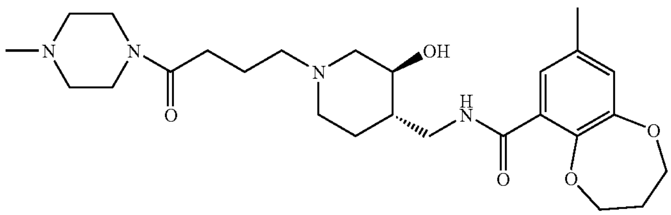 | (3S-trans); ethanedioate (3:2); mp. 112° C. |
| 239 | B.5 | 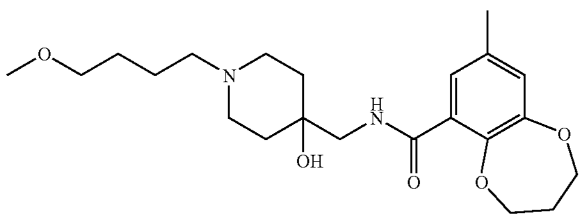 | ethanedioate (1:1); mp. 135° C. |
| 240 | B.5 | 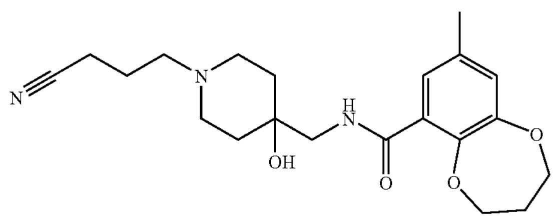 | ethanedioate (1:1); mp. 100° C. |
| 241 | B.5 | 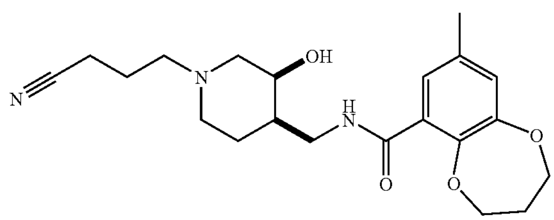 | (cis); ethanedioate (1:1); mp. 192° C. |
| 242 | B.6 | 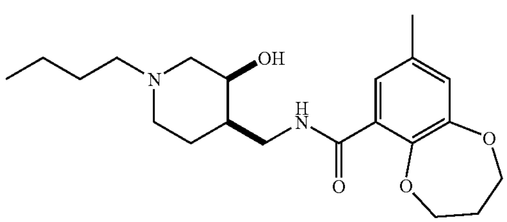 | (cis); ethanedioate (1:1) |
| 243 | B.5 | 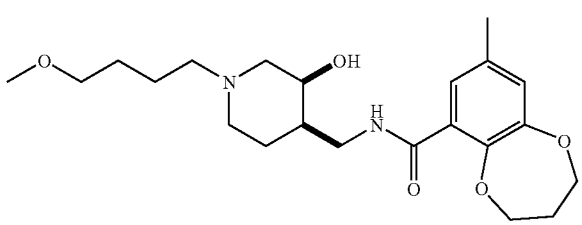 | (cis); ethanedioate (1:1) |

TABLE F-1-continued

| Co. No. | Ex. No. | Structure | Physical data |
|---|---|---|---|
| 244 | B.16 | 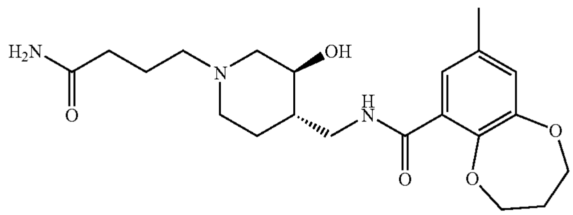 | (3S-trans); mp. 110° C. |
| 245 | B.6 | 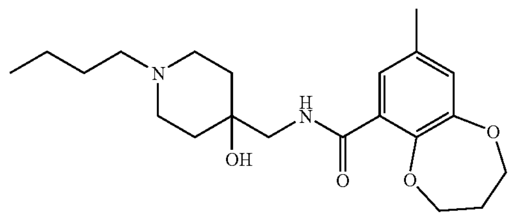 | ethanedioate (1:1); mp. 142° C. |
| 246 | B.5 | 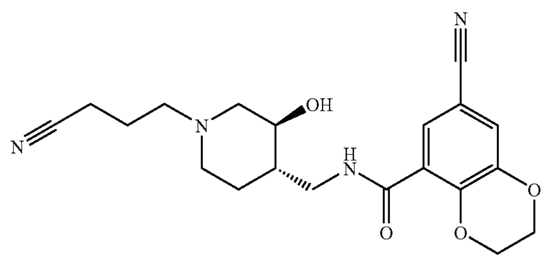 | (3S-trans); mp. 70° C. |
| 247 | B.5 | 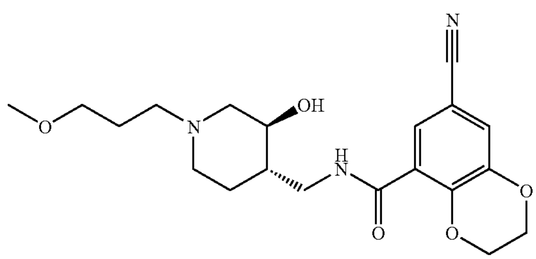 | (3S-trans); ethanedioate (1:1); mp. 140° C. |
| 248 | B.5 | 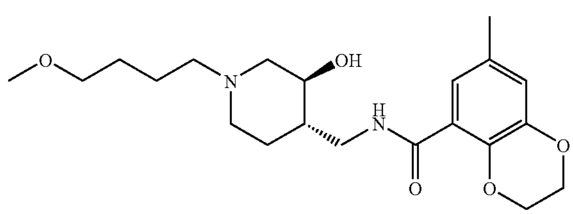 | (3S-trans); ethanedioate (1:1); mp. 70° C. |
| 249 | B.18 | 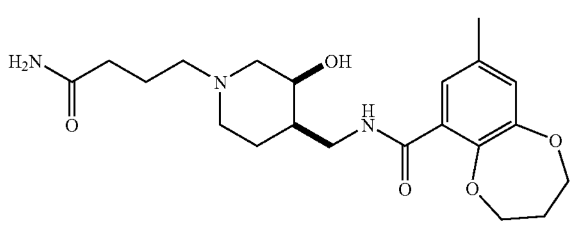 | (cis); |

TABLE F-1-continued

| Co. No. | Ex. No. | Structure | Physical data |
|---|---|---|---|
| 250 | B.5 | 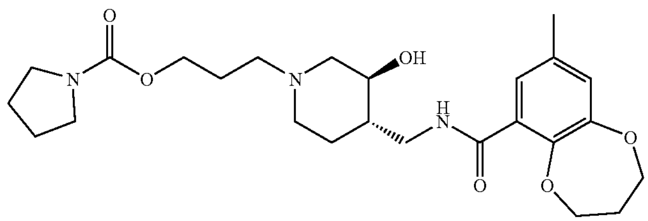 | (3S-trans); |
| 251 | B.5 | 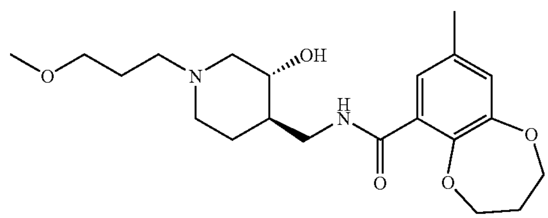 | (3R-trans); mp. 110° C. |
| 252 | B.16 | 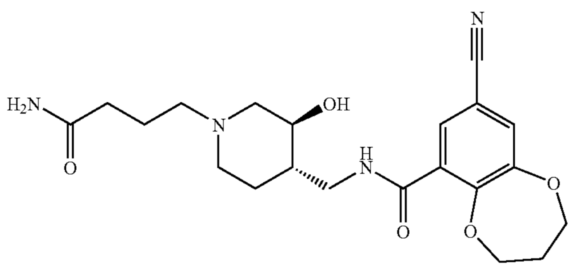 | (3S-trans) |
| 253 | B.18 | 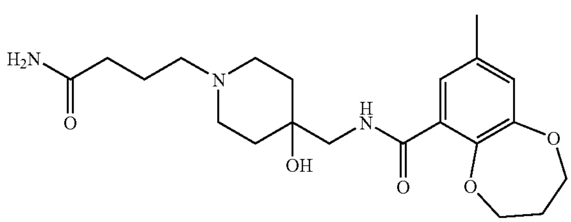 | mp. 80° C. |
| 254 | B.1 | 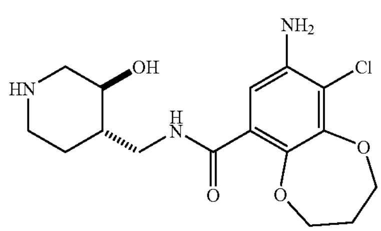 | (trans); HCl (2:1) |
| 255 | B.1 | 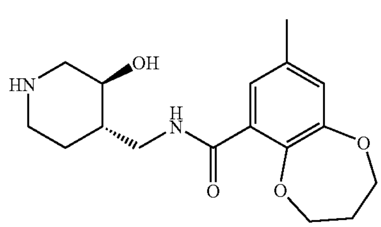 | (3S-trans); |

TABLE F-1-continued

| Co. No. | Ex. No. | Structure | Physical data |
|---|---|---|---|
| 256 | B.1 | 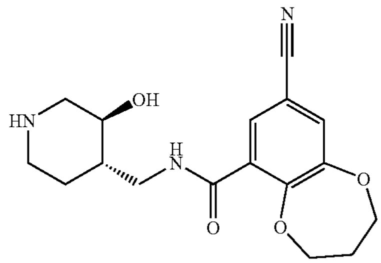 | (3S-trans); |
| 257 | B.1 | 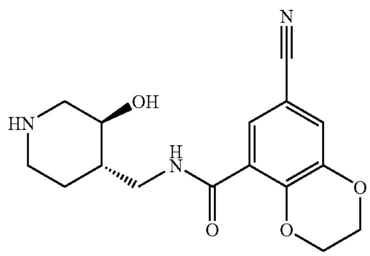 | (3S-trans); |
| 258 | B.1 | 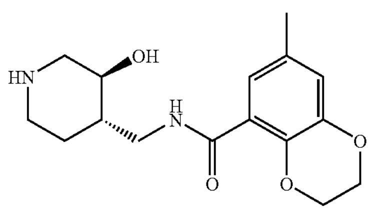 | (3S-trans); |
| 259 | B.1 | 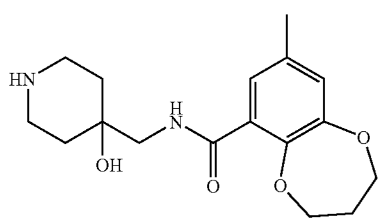 | HCl (2:1) |
| 260 | B.1 | 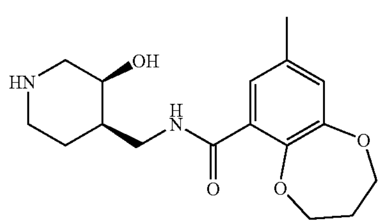 | (cis); |

TABLE F-1-continued

| Co. No. | Ex. No. | Structure | Physical data |
|---|---|---|---|
| 261 | B.1 | 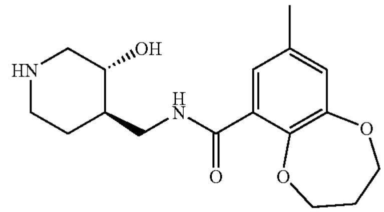 | (3R-trans); HCl |
| 262 | B.7 | 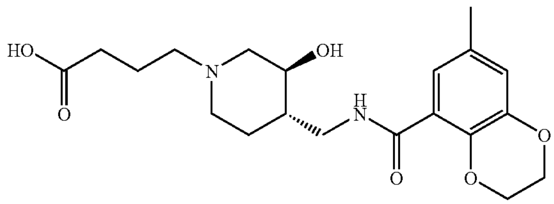 | (3S-trans); |

Pharmacological Examples

Example C.1

5HT$_4$ Antagonism h5-HT$_{4b}$-HEK 293 clone 9 cells were cultured in 150 mm Petri dishes and washed twice with cold PBS. The cells were then scraped from the plates and suspended in 50 mM Tris-HCl buffer, pH 7.4 and harvested by centrifugation at 23,500 rpm for 10 minutes. The pellet was resuspended in 5 mM Tris-HCl, pH 7.4 and homogenized with an Ultra Turrax homogenizer. The membranes were collected by centrifugation at 30,000 rpm for 20 min, resuspended in 50 mM Tris-HCl pH 7.4 and stored at −80° C. For the experiment, assay mixtures (0.5 ml) contained 50 μl of the tritiated ligand (5-HT$_4$ antagonist [$^3$H]GR113808 0.1 nM) and 0.4 ml membrane preparation (15 μg protein/ml). 50 μl of 10% DMSO was added for total binding. 50 μl of 1 μM of (+)-trans-(1-butyl-3-hydroxy-4-piperidinyl)methyl 8-amino-7-chloro-2,3-dihydro-1,4-benzodioxin-5-carboxylate (a proprietary 5HT$_4$ agonist of Janssen Pharmaceutica) was added for determination of non-specific binding.

The [$^3$H]GR113808 assay buffer was 50 mM HEPES-NaOH, pH 7.4. The mixtures were incubated for 30 min at 25° C. The incubation was terminated by filtration over a Unifilter 96 GF/B presoaked in 0.1% polyethylenimine, followed by six washing steps with 50 mM HEPES-NaOH, pH 7.4.

Ligand concentration binding isotherms (rectangular hyperbola) were calculated by nonlinear regression analysis and the pIC$_{50}$ data for all tested compounds are listed below in Table C.1.

TABLE C.1

5HT$_4$ antagonistic data

| Co. No. | pIC$_{50}$ |
|---|---|
| 1 | 7.31 |
| 2 | 6.28 |

TABLE C.1-continued

5HT$_4$ antagonistic data

| Co. No. | pIC$_{50}$ |
|---|---|
| 3 | 7.42 |
| 4 | 7.16 |
| 5 | 7.19 |
| 6 | 7.24 |
| 7 | 7.75 |
| 8 | 6.43 |
| 9 | 7.79 |
| 10 | 8.22 |
| 11 | 8.24 |
| 12 | 7.38 |
| 13 | 6.15 |
| 14 | 7.78 |
| 15 | 7.52 |
| 16 | 6.21 |
| 17 | 7.59 |
| 18 | 6.71 |
| 19 | 7.76 |
| 20 | 7.28 |
| 21 | 7.2 |
| 22 | 7.75 |
| 23 | 7.72 |
| 25 | 6.86 |
| 26 | 7.72 |
| 27 | 5.58 |
| 28 | 7.81 |
| 29 | 7.96 |
| 30 | 7.5 |
| 31 | 8.48 |
| 32 | 7.2 |
| 33 | 6.73 |
| 34 | 7.5 |
| 35 | 7.35 |
| 36 | 7.67 |
| 37 | 7.44 |
| 38 | 6.54 |
| 39 | 5.91 |
| 40 | 8.16 |
| 41 | 7.81 |
| 42 | 7.73 |
| 43 | 7.88 |
| 44 | 7.64 |
| 45 | 6.87 |

TABLE C.1-continued

5HT$_4$ antagonistic data

| Co. No. | pIC$_{50}$ |
|---|---|
| 46 | 8.08 |
| 47 | 7.5 |
| 48 | 7.48 |
| 49 | 7.59 |
| 50 | 7.3 |
| 51 | 7.84 |
| 52 | 7.83 |
| 53 | 7.7 |
| 54 | 7.83 |
| 55 | 7.19 |
| 56 | 7.75 |
| 58 | 7.85 |
| 59 | 7.29 |
| 60 | 7.09 |
| 61 | 7.84 |
| 62 | 7.09 |
| 63 | 7.16 |
| 64 | 7.81 |
| 65 | 8.45 |
| 66 | 6.55 |
| 67 | 6.32 |
| 68 | 7.52 |
| 69 | 6.31 |
| 70 | 7.05 |
| 71 | 7.93 |
| 72 | 7.08 |
| 73 | 7.26 |
| 74 | 6.67 |
| 75 | 7.51 |
| 76 | 7.64 |
| 77 | 7.16 |
| 78 | 8.03 |
| 79 | 7.4 |
| 80 | 8.12 |
| 81 | 5.94 |
| 82 | 5.21 |
| 83 | 7.83 |
| 84 | 7.03 |
| 85 | 8.2 |
| 86 | 6.88 |
| 86 | 6.88 |
| 87 | 7.89 |
| 88 | 6.59 |
| 89 | 7.51 |
| 90 | 7.46 |
| 91 | 6.64 |
| 92 | 7.92 |
| 93 | 7.77 |
| 94 | 7.46 |
| 95 | 7.44 |
| 96 | 8.21 |
| 97 | 7.8 |
| 98 | 7.83 |
| 99 | 7.14 |
| 100 | 7.78 |
| 101 | 7.3 |
| 102 | 6.92 |
| 103 | 7.64 |
| 104 | 7.47 |
| 105 | 6.36 |
| 106 | 6.44 |
| 107 | 8.26 |
| 108 | 7.59 |
| 109 | 7.44 |
| 110 | 7.72 |
| 111 | 7.7 |
| 112 | 7.88 |
| 113 | 6.9 |
| 114 | 8.08 |
| 115 | 7.79 |
| 116 | 7.79 |
| 117 | 8.81 |
| 118 | 7.22 |
| 119 | 8.05 |
| 120 | 7.36 |
| 121 | 6.15 |
| 122 | 7.49 |
| 123 | 7.36 |
| 124 | 7.57 |
| 125 | 7.79 |
| 126 | 7.74 |
| 127 | 7.77 |
| 128 | 7.78 |
| 129 | 7.79 |
| 130 | 7.26 |
| 131 | 6.87 |
| 132 | 7.04 |
| 133 | 6.27 |
| 134 | 7.02 |
| 135 | 7.03 |
| 136 | 7.09 |
| 137 | 7.56 |
| 138 | 7.09 |
| 139 | 7.4 |
| 140 | 7.03 |
| 141 | 7.36 |
| 142 | 5.94 |
| 143 | 7.21 |
| 144 | 6.95 |
| 145 | 7.2 |
| 146 | 7.46 |
| 147 | 7.36 |
| 148 | 7 |
| 149 | 5.45 |
| 150 | 6.92 |
| 151 | 7.05 |
| 152 | 7.62 |
| 153 | 7.86 |
| 154 | 5.5 |
| 155 | 7.26 |
| 156 | 7.33 |
| 157 | 7.09 |
| 158 | 7.99 |
| 159 | 8.3 |
| 160 | 7.7 |
| 161 | 7.07 |
| 162 | 8.51 |
| 163 | 8.64 |
| 164 | 9 |
| 165 | 7.8 |
| 166 | 8.37 |
| 167 | 5.62 |
| 168 | 8.7 |
| 169 | 7.49 |
| 170 | 7.79 |
| 171 | 8.79 |
| 172 | 6.97 |
| 173 | 8.52 |
| 174 | 6.93 |
| 175 | 6.91 |
| 176 | 7.79 |
| 177 | 6.965 |
| 178 | 5.85 |
| 179 | 7.2 |
| 180 | 7.36 |
| 181 | 8.07 |
| 182 | 7 |
| 183 | 8.46 |
| 184 | 7.7 |
| 185 | 7.71 |
| 186 | 8.3 |
| 187 | 7.94 |
| 188 | 6.08 |
| 189 | 8.73 |
| 190 | 6.57 |

TABLE C.1-continued

5HT$_4$ antagonistic data

| Co. No. | pIC$_{50}$ |
|---|---|
| 192 | 7.51 |
| 193 | 8.773 |
| 194 | 9.23 |
| 195 | 8.44 |
| 196 | 9.37 |
| 197 | 8.65 |
| 198 | 8.92 |
| 199 | 7.91 |
| 200 | 9.02 |
| 201 | 7.84 |
| 202 | 8.36 |
| 203 | 5.87 |
| 204 | 7.08 |
| 205 | 8.56 |
| 206 | 8.5 |
| 207 | 7.43 |
| 208 | 8.25 |
| 209 | 7.75 |
| 210 | 8.28 |
| 211 | 8.53 |
| 212 | 9.09 |
| 213 | 8.58 |
| 214 | 8.63 |
| 215 | 8.3 |
| 216 | 7.35 |
| 217 | 8.83 |
| 218 | 9.11 |
| 219 | 8.73 |
| 220 | 8.6 |
| 221 | 8.51 |
| 222 | 8.88 |
| 223 | 8.43 |
| 224 | 8.75 |
| 225 | 9.12 |
| 227 | 9.3 |
| 228 | 9.4 |
| 229 | 9.26 |
| 230 | 9.3 |
| 231 | 9.11 |
| 232 | 9.4 |
| 233 | 9.45 |
| 234 | 9.31 |
| 235 | 7.43 |
| 236 | 7.32 |
| 237 | 8.84 |
| 238 | 9.07 |
| 239 | 7.72 |
| 240 | 7.34 |
| 241 | 7.71 |
| 242 | 9.1 |
| 243 | 8.03 |
| 244 | 9.76 |
| 245 | 8.67 |
| 246 | 7.9 |
| 247 | 8.4 |
| 248 | 9.65 |
| 249 | 7.43 |
| 250 | 9.12 |
| 251 | 7.51 |
| 252 | 8.37 |
| 253 | 7.5 |

Example C.2

"Metabolic Stability"

Sub-cellular tissue preparations were made according to Gorrod et al. (Xenobiotica 5:453-462, 1975) by centrifugal separation after mechanical homogenization of tissue. Liver tissue was rinsed in ice-cold 0.1 M Tris-HCl (pH 7.4) buffer to wash excess blood. Tissue was then blotted dry, weighed and chopped coarsely using surgical scissors. The tissue pieces were homogenized in 3 volumes of ice-cold 0.1 M phosphate buffer (pH 7.4).

Tissue homogenates were centrifuged at 9000×g for 20 minutes at 4° C. The resulting supernatant was stored at −80° C. and is designated 'S9'.

The S9 fraction can be further centrifuged at 100.000×g for 60 minutes (4° C.). The resulting supernatant was carefully aspirated, aliquoted and designated 'cytosol'. The pellet was re-suspended in 0.1 M phosphate buffer (pH 7.4) in a final volume of 1 ml per 0.5 g original tissue weight and designated 'microsomes'.

All sub-cellular fractions were aliquoted, immediately frozen in liquid nitrogen and stored at −80° C. until use.

For the samples to be tested, the incubation mixture contained PBS (0.1M), compound (5 μM), microsomes (1 mg/ml) and a NADPH-generating system (0.8 mM glucose-6-phosphate, 0.8 mM magnesium chloride and 0.8 Units of glucose-6-phosphate dehydrogenase). Control samples contained the same material but the microsomes were replaced by heat inactivated (10 minutes at 95 degrees Celsius) microsomes. Recovery of the compounds in the control samples was always 100%.

The mixtures were preincubated for 5 minutes at 37 degrees Celsius. The reaction was started at time point zero (t=0) by addition of 0.8 mM NADP and the samples were incubated for 60 minutes (t=60). The reaction was terminated by the addition of 2 volumes of DMSO. Then the samples were centrifuged for 10 minutes at 900×g and the supernatants were stored at room temperature for no longer as 24 hours before analysis. All incubations were performed in duplo. Analysis of the supernatants was performed with LC-MS analysis. Elution of the samples was performed on a Xterra MS C18 (50×4.6 mm, 5 μm, Waters, US). An Alliance 2790 (Supplier: Waters, US) HPLC system was used. Elution was with buffer A (25 mM ammoniumacetate (pH 5.2) in H$_2$O/acetonitrile (95/5)), solvent B being acetonitrile and solvent C methanol at a flow rate of 2.4 ml/min. The gradient employed was increasing the organic phase concentration from 0% over 50% B and 50% C in 5 min up to 100% B in 1 minute in a linear fashion and organic phase concentration was kept stationary for an additional 1.5 minutes. Total injection volume of the samples was 25 μl.

A Quatro triple quadrupole mass spectrometer fitted with and ESP source was used as detector. The source and the desolvation temperature were set at 120 and 350° C. respectively and nitrogen was used as nebuliser and drying gas. Data were acquired in positive scan mode (single ion reaction). Cone voltage was set at 10 V and the dwell time was 1 second.

Metabolic stability was expressed as % metabolism of the compound after 60 minutes (equation given as example) of incubation in the presence of active microsomes (E(act))

$$\left( \% \text{ metabolism} = 100\% - \left( \left( \frac{\text{Total Ion Current }(TIC)\text{ of }E(\text{act})\text{ at }t=60}{TIC\text{ of }E(\text{act})\text{ at }t=0} \right) \times 100 \right) \right).$$

TABLE C.2

% metabolised compound of the present invention (left column) compared analogous structures of WO-00/37461 (right column)

| Comparative structures of present invention | % | Comparative structures of WO-00/37461 | % |
|---|---|---|---|
| Co. No. 246; (3S-trans) | 7 | Co. No. 74; (trans) | 50.5 |
| Co. No. 247; (3S-trans) | 12 | Co. No. 67; (trans) | 30 |
| Co. No. 228; (3S-trans) | 6 | Co. No. 68; (trans) | 10 |

TABLE C.2-continued

% metabolised compound of the present invention (left column) compared analogous structures of WO-00/37461 (right column)

| Comparative structures of present invention | % | Comparative structures of WO-00/37461 | % |
|---|---|---|---|
| Co. No. 159; (trans) | 22 | Co. No. 119; (trans) | 68 |
| Co. No. 183; (trans) | 10 | Co. No. 119; (trans) | 68 |
| Co. No. 87; (trans) | 4 | Co. No. 120; (trans) | 25 |

TABLE C.2-continued

% metabolised compound of the present invention (left column) compared analogous structures of WO-00/37461 (right column)

| Comparative structures of present invention | % | Comparative structures of WO-00/37461 | % |
|---|---|---|---|
| Co. No. 158; (trans) | 5 | Co. No. 120; (trans) | 25 |
| Co. No. 162; (trans) | 9 | Co. No. 120; (trans) | 25 |
| Co. No. 177; (trans) | 4 | Co. No. 120; (trans) | 25 |

TABLE C.2-continued

% metabolised compound of the present invention (left column) compared analogous structures of WO-00/37461 (right column)

| Comparative structures of present invention | % | Comparative structures of WO-00/37461 | % |
|---|---|---|---|
| Co. No. 184; (trans) | 12 | Co. No. 120; (trans) | 25 |
| Co. No. 200; (3S-trans) | 15 | Co. No. 120; (trans) | 25 |
| Co. No. 202; (3S-trans) | 8 | Co. No. 120; (trans) | 25 |

TABLE C.2-continued

% metabolised compound of the present invention (left column) compared analogous structures of WO-00/37461 (right column)

| Comparative structures of present invention | % | Comparative structures of WO-00/37461 | % |
|---|---|---|---|
| Co. No. 125; (trans) | 6 | Co. No. 122; (trans) | 79 |
| Co. No. 186; (trans) | 0 | Co. No. 122; (trans) | 79 |
| Co. No. 227; (3S-trans) | 24 | Co. No. 124; (trans) | 49.5 |

TABLE C.2-continued

% metabolised compound of the present invention (left column) compared analogous structures of WO-00/37461 (right column)

| Comparative structures of present invention | % | Comparative structures of WO-00/37461 | % |
|---|---|---|---|
| Co. No. 229; (3S-trans) | 12 | Co. No. 121; (trans) | 30 |
| Co. No. 211; (3S-trans) | 13 | Co. No. 128; (trans) | 26 |
| Co. No. 163; (trans) | 11 | Co. No. 143; (trans) | 63 |

TABLE C.2-continued

% metabolised compound of the present invention (left column) compared analogous structures of WO-00/37461 (right column)

| Comparative structures of present invention | % | Comparative structures of WO-00/37461 | % |
|---|---|---|---|
| Co. No. 187; (trans) | 18 | Co. No. 143; (trans) | 63 |
| Co. No. 165; (trans) | 1 | Co. No. 144; (trans) | 11 |
| Co. No. 168; (trans) | 4 | Co. No. 144; (trans) | 11 |

TABLE C.2-continued
% metabolised compound of the present invention (left column) compared analogous structures of WO-00/37461 (right column)
| Comparative structures of present invention | % | Comparative structures of WO-00/37461 | % |
|---|---|---|---|
| 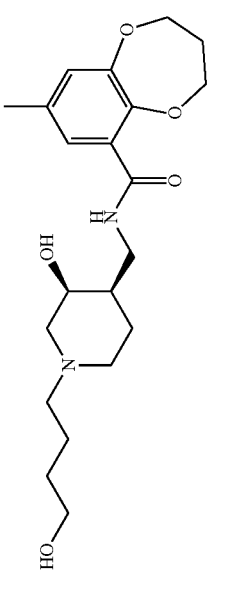 Co. No. 185; (trans) | 3 | 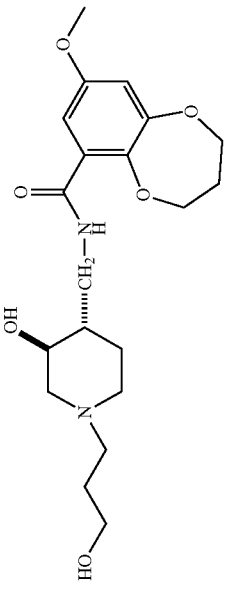 Co. No. 144; (trans) | 11 |
| 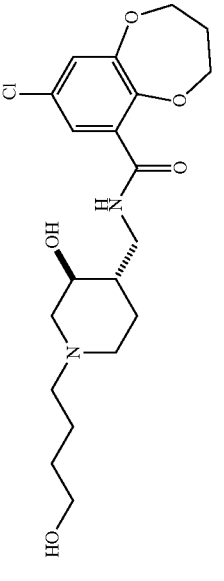 Co. No. 225; (3S-trans) | 14 | 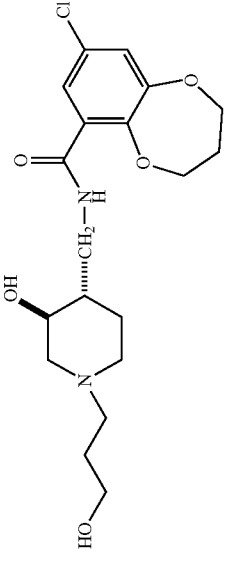 Co. No. 160; (trans) | 23 |

The invention claimed is:
1. A compound of formula (I)

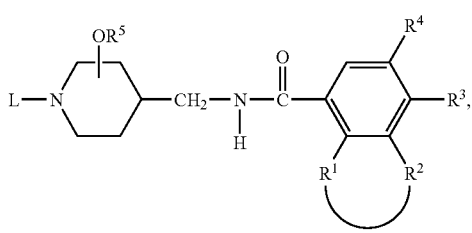

a stereochemically isomeric form thereof, an N-oxide form thereof, or a pharmaceutically acceptable acid or base addition salt thereof, wherein
—R$^1$—R$^2$— is a bivalent radical of formula —O—CH$_2$—CH$_2$—O— (a-3), —O—CH$_2$—CH$_2$—CH$_2$—O— (a-5), wherein in said bivalent radicals optionally one or two hydrogen atoms on the same or a different carbon atom may be replaced by C$_{1-6}$alkyl or hydroxy,
R$^3$ is hydrogen, halo, C$_{1-4}$alkyl;
R$^4$ is C$_{1-6}$alkyl; C$_{1-6}$alkyl substituted with cyano, or C$_{1-6}$alkyloxy; C$_{1-6}$alkyloxy; cyano; amino or mono or di(C$_{1-6}$alkyl)amino;
R$^5$ is hydrogen or C$_{1-6}$alkyl, and the —OR$^5$ radical is situated at the 3- or 4-position of the piperidine moiety;
L is hydrogen, or L is a radical of formula -Alk-R$^6$ (b-1), -Alk-X—R$^7$ (b-2), -Alk-Y—C(=O)—R$^9$ (b-3), or -Alk-Z-C(=O)—NR$^{11}$R$^{12}$ (b-4), wherein each Alk is C$_{1-12}$alkanediyl; and
R$^6$ is hydrogen; hydroxy; cyano; C$_{3-6}$cycloalkyl; C$_{1-6}$alkylsulfonylamino; aryl or Het;
R$^7$ is C$_{1-6}$alkyl; C$_{1-6}$alkyl substituted with hydroxy; C$_{3-6}$cycloalkyl; aryl or Het;
X is O, S, SO$_2$ or NR$^8$; said R$^8$ being hydrogen or C$_{1-6}$alkyl;
R$^9$ is C$_{1-6}$alkyl or hydroxy;
Y is a direct bond;
Z is a direct bond or O;
R$^{11}$ and R$^{12}$ each independently are hydrogen, or C$_{1-6}$alkyl, or R$^{11}$ and R$^{12}$ combined with the nitrogen atom bearing R$^{11}$ and R$^{12}$ may form a pyrrolidinyl, or piperazinyl substituted with C$_{1-6}$alkyl;
aryl represents unsubstituted phenyl or phenyl substituted with 1, 2 or 3 substituents each independently selected from halo, hydroxy, C$_{1-6}$alkyl, C$_{1-6}$alkyloxy, and aminosulfonyl; and
Het is tetrahydrofuranyl; tetrahydrofuranyl substituted with C$_{1-6}$alkyl;
dioxolanyl; dioxolanyl substituted with C$_{1-6}$alkyl;
pyridinyl; pyridinyl substituted with one or two substituents each independently selected from halo, hydroxy, C$_{1-6}$alkyl;
pyrimidinyl; pyrimidinyl substituted with one or two substituents each independently selected from halo, hydroxy, or C$_{1-6}$alkyl;
pyridazinyl; pyridazinyl substituted with one or two substituents each independently selected from hydroxy, C$_{1-6}$alkyloxy, C$_{1-6}$alkyl or halo;
pyrazinyl; pyrazinyl substituted with one or two substituents each independently selected from hydroxy, C$_{1-6}$alkyloxy, C$_{1-6}$alkyl or halo.

2. The compound as claimed in claim 1 wherein the —OR$^5$ radical is situated at the 3-position of the piperidine moiety having the trans configuration.

3. The compound as claimed in claim 2 wherein the absolute configuration of said piperidine moiety is (3S, 4S).

4. The compound as claimed in claim 1 wherein —R$^1$—R$^2$— is a radical of formula (a-5); R$^3$ is hydrogen; R$^4$ is methyl; and R$^5$ is hydrogen.

5. The compound as claimed in claim 4 wherein L is a radical of formula (b-2) wherein X is O, Alk is C$_{1-4}$alkanediyl and R$^7$ is C$_{1-6}$alkyl.

6. A compound as claimed in claim 1, wherein the compound is (3S)-trans-8-methyl-3,4-dihydro-2H-benzo[b][1,4]dioxepine-6-carboxylic acid [3-hydroxy-1-(3-methoxy-propyl)-piperidin-4-ylmethyl]-amide or a pharmaceutically acceptable acid addition salt thereof.

7. A pharmaceutical composition comprising a pharmaceutically acceptable cater and a therapeutically active amount of a compound according to claim 1.

8. A method for treating hypermotility, irritable bowel syndrome, constipation or diarrhea predominant IDS, pain and non-pain predominant IBS and bowel hypersensitivity comprising administering to a patient in need thereof an effective amount of a compound according to claim 1.

9. A process for preparing a compound of formula (I) wherein
a) an intermediate of formula (II) is reacted with an carboxylic acid derivative of formula (III) or a reactive functional derivative thereof;

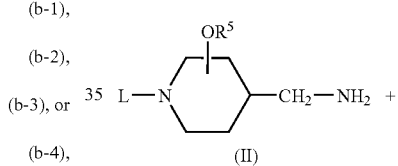

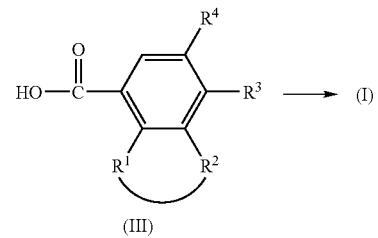

b) an intermediate of formula (IV) is N-alkylated with a compound of formula (I-a), defined as a compound of formula (I) wherein L represents hydrogen, in a reaction-inert solvent and, optionally in the presence of a suitable base, thereby yielding compounds of formula (I-b), defined as compounds of formula (I) wherein L is other than hydrogen;

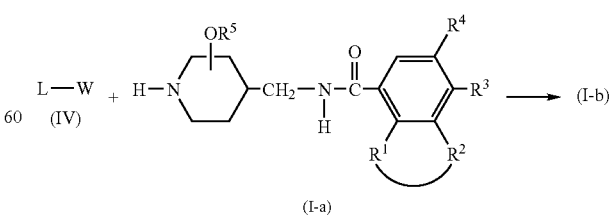

c) an appropriate ketone or aldehyde intermediate of formula L'=O (V), said L'=O being a compound of formula L-H, wherein two geminal hydrogen atoms in the $C_{1-12}$alkanediyl moiety are replaced by =O, is reacted with a compound of formula (I-a), thereby yielding compounds of formula (I-b);

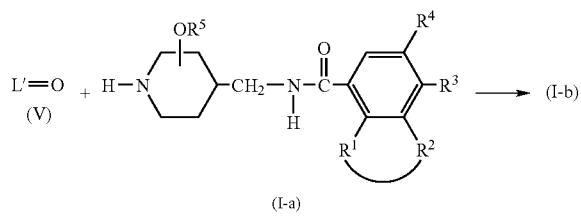

wherein in the above reaction schemes the radicals —$R^1$—$R^2$—, $R^3$, $R^4$, $R^5$ and L are as defined in claim 1 and W is an appropriate leaving group;

d) or, compounds of formula (I) are converted into each other following art-known transformation reactions; or if desired; a compound of formula (I) is converted into a pharmaceutically acceptable acid addition salt, or conversely, an acid addition salt of a compound of formula (I) is converted into a free base form with alkali; and, if desired, preparing stereochemically isomeric forms thereof.

* * * * *

UNITED STATES PATENT AND TRADEMARK OFFICE
CERTIFICATE OF CORRECTION

PATENT NO. : 7,638,535 B2 Page 1 of 1
APPLICATION NO. : 10/560479
DATED : December 29, 2009
INVENTOR(S) : Jean-Paul René Marie André Bosmans et al.

It is certified that error appears in the above-identified patent and that said Letters Patent is hereby corrected as shown below:

Column 2,
Line 62, delete "$C_1$alkyl" and insert -- $C_{1-6}$alkyl --.

Column 5,
Line 66, delete "formula (M)" and insert -- formula (III). --.

Column 33,
Line 46, delete "(c=23.16 mg/S" and insert -- (c=23.16 mg/5 --.

Column 56,
Line 13, delete "($CH_3OHINH_3$)" and insert -- ($CH_3OH/NH_3$) --.

Column 134,
In row 199, delete "(trans); ethanoldioate (1:1); mp. 146°C." and insert -- (trans); ethanedioate (1:1); mp. 146°C. --.

Column 178,
Line 20, delete "cater" and insert -- carrier --.

Signed and Sealed this

Thirteenth Day of April, 2010

David J. Kappos
*Director of the United States Patent and Trademark Office*

UNITED STATES PATENT AND TRADEMARK OFFICE
CERTIFICATE OF CORRECTION

PATENT NO.         : 7,638,535 B2                                           Page 1 of 1
APPLICATION NO. : 10/560479
DATED              : December 29, 2009
INVENTOR(S)        : Bosmans et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 881 days.

Signed and Sealed this

Ninth Day of November, 2010

David J. Kappos
*Director of the United States Patent and Trademark Office*